United States Patent
Anémian et al.

(10) Patent No.: US 10,714,691 B2
(45) Date of Patent: *Jul. 14, 2020

(54) FORMULATIONS FOR THE PRODUCTION OF ELECTRONIC DEVICES

(71) Applicant: Merck Patent GmbH, Darmstadt (DE)

(72) Inventors: Rémi Manouk Anémian, Seoul (KR); Susanne Heun, Bad Soden (DE); Thomas Eberle, Landau (DE); Philipp Stoessel, Frankfurt am Main (DE)

(73) Assignee: Merck Patent GmbH (DE)

( * ) Notice: Subject to any disclaimer, the term of this patent is extended or adjusted under 35 U.S.C. 154(b) by 395 days.

This patent is subject to a terminal disclaimer.

(21) Appl. No.: 15/402,750

(22) Filed: Jan. 10, 2017

(65) Prior Publication Data

US 2017/0125676 A1 May 4, 2017

Related U.S. Application Data

(63) Continuation of application No. 13/395,542, filed as application No. PCT/EP2010/005648 on Sep. 15, 2010, now Pat. No. 9,666,806.

(30) Foreign Application Priority Data

Sep. 16, 2009 (DE) .......................... 10 2009 041 414
Nov. 17, 2009 (DE) .......................... 10 2009 053 644
(Continued)

(51) Int. Cl.
*H01B 1/20* (2006.01)
*H01L 51/00* (2006.01)
(Continued)

(52) U.S. Cl.
CPC ............ *H01L 51/005* (2013.01); *C07C 15/38* (2013.01); *C07C 49/784* (2013.01);
(Continued)

(58) Field of Classification Search
CPC ... H01B 1/20; C07F 5/02; C07F 15/00; C07C 49/215; C07C 13/48; H01L 21/31; C07D 405/04; C07D 251/24; C09K 11/02
See application file for complete search history.

(56) References Cited

U.S. PATENT DOCUMENTS 8,314,549 B2 11/2012 Burn et al.
2005/0249970 A1 11/2005 Suzuri et al.
(Continued)

FOREIGN PATENT DOCUMENTS

CN 1492904 A 4/2004
CN 101177608 A 5/2008
(Continued)

OTHER PUBLICATIONS

Miller et al., Synethsis and Characterization of a Series of Monodispers 1,3,5-Phenylene-Based Hydrocarbon Dendrimers Including C276H186 and Their Fluorinated Analogues, J. Am. Chem. Soc. 1992, 114, 1018-1025.*

(Continued)

*Primary Examiner* — Anthony J Frost
(74) *Attorney, Agent, or Firm* — Faegre Drinker Biddle & Reath LLP

(57) ABSTRACT

The present invention relates to a formula, comprising at least one solvent, and at least one functional composition of the general formula (I), wherein A is a functional structural element, B is a solvent-providing structural element, and k is an integer in the range of 1 to 20. The molecular weight of the functional composition is at least 550 g/mol, and the solvent-providing structural element B corresponds to the general formula ((L-I). Ar1, Ar2 JeWeUs, independently of each other, signify an aryl or heteroaryl group, which can be substituted with one or several discretionary residues R.

(Continued)

Each X is, independently of one another, N or CR2, preferably CH. R1, R2, independently of one another, is hydrogen, a linear alkyl, alkoxy, or thioalkoxy group with 1 to 40 C atoms, or a branched or cyclic alkyl, alkoxy, or thioalkoxy group with 3 to 40 C atoms, or a silyl group, or a substituted keto group with 1 to 40 C atoms, an alkoxycarbonyl group with 2 to 40 C atoms, an aryloxycarbonyl group with 7 to 40 C atoms, a cyano group (—CN), a carbamoyl group (—C(=O)NH2), a haloformyl group (—C(=O)—X, wherein X signifies a halogen atom), a formyl group (—C(=O)—H), an isocyano group, an isocyanate group, a thiocyanate group or a thioisocyanate group, a hydroxy group, a nitro group, a CF3 group, C1, Br, F, a cross-linkable group, or a substituted or non-substituted aromatic or heteroaromatic ring system with 5 to 60 ring atoms, or an aryloxy or heteroaryloxy group with 5 to 60 ring atoms, or a combination of these systems, wherein one or several of groups R1 and/or R2 can form a monocyclic or polycyclic, aliphatic or aromatic ring system with one another and/or with the ring to which group R1 is bound, and I is 0, 1, 2, 3 or 4, wherein the dashed linkage indicates the linkage to the functional structure element A. The present invention further relates to preferred compositions of the formula (I) and electronic devices containing said compositions.

20 Claims, 1 Drawing Sheet

(30) Foreign Application Priority Data

Nov. 17, 2009 (DE) .................. 10 2009 053 645
Jun. 15, 2010 (EP) .................... 10006208

(51) Int. Cl.

| | |
|---|---|
| C07C 15/38 | (2006.01) |
| C07C 49/784 | (2006.01) |
| C07D 251/24 | (2006.01) |
| C07D 403/04 | (2006.01) |
| C07F 15/00 | (2006.01) |
| C09K 11/02 | (2006.01) |
| C09K 11/06 | (2006.01) |
| H01L 51/05 | (2006.01) |
| H01L 51/42 | (2006.01) |
| H01L 51/50 | (2006.01) |

(52) U.S. Cl.
CPC ......... *C07D 251/24* (2013.01); *C07D 403/04* (2013.01); *C07F 15/0033* (2013.01); *C09K 11/02* (2013.01); *C09K 11/06* (2013.01); *H01L 51/0054* (2013.01); *H01L 51/0056* (2013.01); *H01L 51/0058* (2013.01); *H01L 51/0067* (2013.01); *H01L 51/0072* (2013.01); *H01L 51/0085* (2013.01); *B32B 2457/20* (2013.01); *C07C 2603/24* (2017.05); *C07C 2603/42* (2017.05); *C09K 2211/1007* (2013.01); *C09K 2211/1011* (2013.01); *C09K 2211/1029* (2013.01); *C09K 2211/1059* (2013.01); *C09K 2211/185* (2013.01); *H01L 51/0003* (2013.01); *H01L 51/0052* (2013.01); *H01L 51/0508* (2013.01); *H01L 51/42* (2013.01); *H01L 51/5012* (2013.01); *H01L 51/5016* (2013.01); *H01L 51/5048* (2013.01); *H01L 51/5056* (2013.01); *H01L 51/5072* (2013.01); *H01L 51/5088* (2013.01); *H01L 51/5092* (2013.01); *H01L 51/5096* (2013.01); *Y02E 10/549* (2013.01); *Y10T 428/10* (2015.01); *Y10T 428/1036* (2015.01)

(56) References Cited

U.S. PATENT DOCUMENTS

| | | | |
|---|---|---|---|
| 2006/0014046 A1* | 1/2006 | Wang | ............... C07C 15/28 428/690 |
| 2006/0127696 A1 | 6/2006 | Stossel et al. | |
| 2007/0009760 A1 | 1/2007 | Inoue et al. | |
| 2007/0013296 A1 | 1/2007 | Kubota et al. | |
| 2008/0009627 A1 | 1/2008 | Tsuboyama et al. | |
| 2008/0088230 A1 | 4/2008 | Suzuri et al. | |
| 2008/0113101 A1 | 5/2008 | Inoue et al. | |
| 2009/0140637 A1 | 6/2009 | Hosokawa et al. | |
| 2009/0191426 A2 | 7/2009 | Yabe et al. | |
| 2010/0013377 A1 | 1/2010 | Male et al. | |
| 2011/0095282 A1 | 4/2011 | Pflumm et al. | |
| 2011/0140043 A1 | 6/2011 | Stoessel et al. | |
| 2012/0068170 A1 | 3/2012 | Pflumm et al. | |

FOREIGN PATENT DOCUMENTS

| | | | |
|---|---|---|---|
| DE | 10238903 A1 | | 3/2004 |
| JP | 2007126443 A | * | 5/2007 |
| JP | 2008127316 A | | 6/2008 |
| JP | 2010185047 A | | 8/2010 |
| KR | 20080028425 A | | 3/2008 |
| KR | 20080061370 A | | 7/2008 |
| KR | 20090047547 A | | 5/2009 |
| WO | WO-2004/020504 A1 | | 3/2004 |
| WO | WO-2004095889 A1 | | 11/2004 |
| WO | WO-2005033118 A1 | | 4/2005 |
| WO | WO-2006/097717 A1 | | 9/2006 |
| WO | WO-2006/129107 A1 | | 12/2006 |
| WO | WO-2007007463 A1 | | 1/2007 |
| WO | WO-2009021107 A1 | | 2/2009 |
| WO | WO-2010/006680 A1 | | 1/2010 |
| WO | WO-2011032626 A1 | | 3/2011 |

OTHER PUBLICATIONS

Chinese Office Action for Chinese Application No. 201080041111.7 dated Jan. 4, 2016.
European Examination procedure for application No. 10757570.6, dated Feb. 27, 2015.
European Examination procedure for application No. 10757570.6, dated Nov. 13, 2013.
Kimura et al. "Energy transfer within ruthenium-cored rigid metal-lodendrimers", Tetrahedron Letters 41 (2000) pp. 6809-6813.
Kimura, M., "Energy transfer within ruthenium-cored rigid metal-lodendrimers", Tetrahedron Letters, 2000, vol. 41, pp. 6809-6813.
International Search Report for PCT/EP2010/005648 dated Dec. 15, 2010.
International Preliminary Report on Patentability for PCT/EP2010/005648 dated Mar. 20, 2012.
Miller et. al. Synthesis and Characterization of a Series of Monodispers 1, 3, 5-Phenylene-Based Hydrocarbon Dendrimers including C276H186 and Their Fluorinated Analogues, J. Am. Chem. Soc. 1992, 114, p. 1018-1025.
International Preliminary Report on Patentability (in German) for PCT/EP2010/005648 dated Mar. 20, 2012.
International Search Report (English translation) for PCT/EP2010/005648 dated Dec. 15, 2010.
Written Opinon of the International Searching Authority (English translation) for PCT/EP2010/005648 dated Dec. 15, 2010.

* cited by examiner

| | | |
|---|---|---|
| 3 nm / 100 nm | Cathode | Ba/Al |
| 80 nm | EML | Matrix + emitter |
| 20 nm | HIL | HIL-012 |
| 80 nm | Buffer layer | PEDOT |
| | ITO | |

FORMULATIONS FOR THE PRODUCTION OF ELECTRONIC DEVICES

CROSS-REFERENCE TO RELATED APPLICATIONS

This application is a continuation application of U.S. application Ser. No. 13/395,542 filed Mar. 12, 2012 which is incorporated by reference in its entirety. U.S. application Ser. No. 13/395,542 is a national stage application (under 35 U.S.C. § 371) of PCT/EP2010/005648, filed Sep. 15, 2010, which claims benefit of German application 10 2009 041 414.2, filed Sep. 16, 2009; German application 10 2009 053 644.2, filed Nov. 17, 2009; German application 10 2009 053 645.0, filed Nov. 17, 2009; PCT/EP2010/002683, filed May 3, 2010; and European application 10006208.2, filed Jun. 15, 2010.

The present invention relates to formulations and organic compounds for the production of electronic devices. The present invention furthermore relates to electronic devices and to processes for the production thereof.

Electronic devices which comprise organic, organometallic and/or polymeric semiconductors are increasing in importance; they are employed in many commercial products for cost reasons and owing to their performance. Examples which may be mentioned here are organic-based charge-transport materials (for example triarylamine-based hole transporters) in photocopiers, organic or polymeric light-emitting diodes (OLEDs or PLEDs) in display devices, or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may achieve major importance in the future.

Irrespective of the particular application, many of these electronic devices have the following general layer structure, which can be adapted for the particular application:
(1) substrate,
(2) electrode, frequently metallic or inorganic, but also made from organic or polymeric conductive materials,
(3) charge-injection layer(s) or interlayer(s), for example for compensation of electrode unevenness ("planarisation layer"), frequently made from a conductive, doped polymer,
(4) organic semiconductors,
(5) optionally further charge-transport, charge-injection or charge-blocking layers,
(6) counterelectrode, materials as mentioned under (2),
(7) encapsulation.

The above arrangement represents the general structure of an organic electronic device, where various layers can be combined, resulting in the simplest case in an arrangement comprising two electrodes, between which an organic layer is located. In this case, the organic layer fulfils all functions, including the emission of light in the case of OLEDs. A system of this type is described, for example, in WO 90/13148 A1 based on poly-(p-phenylenes).

However, a problem which arises in a "three-layer system" of this type is the lack of control of charge separation or the lack of a way of optimising the properties of the individual constituents in different layers, as is achieved in a simple manner by a multilayered structure, for example, in the case of SMOLEDs ("small-molecule OLEDs").

A small-molecule OLED often comprises one or more organic hole-injection layers, hole-transport layers, emission layers, electron-transport layers and/or electron-injection layers and an anode and a cathode, where the entire system is usually located on a glass substrate. The advantage of a multilayered structure of this type consists in that the various functions of charge injection, charge transport and emission can be distributed over the various layers and the properties of the respective layers can thus be modified separately. This modification enables the performance of the electronic devices to be considerably improved.

A disadvantage of electronic devices which are based on the small molecules described above, i.e. non-polymeric compounds, is the production thereof. Non-polymeric compounds are usually converted into electronic devices by evaporation techniques. This represents a major cost disadvantage, in particular for large-area devices, since a multi-step vacuum process in various chambers is very expensive and must be controlled very precisely. Less expensive and established coating methods from solution, such as, for example, ink-jet printing, airbrush methods, roll-to-roll processes, etc., would be a major advantage here. However, the above-described devices comprising small molecules generally cannot be produced in this way owing to the low solubility of the non-polymeric compounds in the usual solvents. Although the solubility of these compounds can be improved by modification, the electronic devices obtained exhibit, however, reduced performance and lifetime compared with the devices obtained by gas-phase deposition.

Thus, for example, WO 2009/021107 A1 and WO 2010/006680 A1 describe organic compounds which are suitable for the production of electronic devices, where these compounds can be processed both by gas-phase deposition and from solution. However, the electronic devices obtained by gas-phase deposition have a more favourable property profile.

Known electronic devices have a usable property profile. However, there is an ongoing necessity to improve the properties of these devices. These properties include, in particular, the lifetime of the electronic devices. A further problem is, in particular, the energy efficiency with which an electronic device achieves the specified object. In the case of organic light-emitting diodes, which may be based both on low-molecular-weight compounds and also on polymeric materials, the light yield, in particular, should be high, meaning that as little electrical power as possible has to be consumed in order to achieve a certain light flux. Furthermore, the lowest possible voltage should also be necessary in order to achieve a pre-specified luminous density.

A further object can be regarded as the provision of electronic devices having excellent performance as inexpensively as possible and in constant quality.

Furthermore, the electronic devices should be capable of being employed or adapted for many purposes. In particular, the performance of the electronic devices should be retained over a broad temperature range.

SUMMARY OF THE INVENTION

Surprisingly, it has been found that these and further objects, which are not mentioned explicitly, but can readily be derived or inferred from the connections discussed in the introduction herein, are achieved by formulations having all features of patent claim 1. Advantageous modifications of the formulations according to the invention are protected in the claims which are dependent on claim 1.

The present invention accordingly relates to a formulation comprising at least one solvent and at least one functional compound of the general formula (I)

$$A\text{---}[B]_k \qquad (I)$$

where
A is a functional structural element,
B is a solubility-promoting structural element and
k is an integer in the range from 1 to 20,
which is characterised in that
the molecular weight of the functional compound is at least 550 g/mol and the solubility-promoting structural element B conforms to the general formula (L-I)

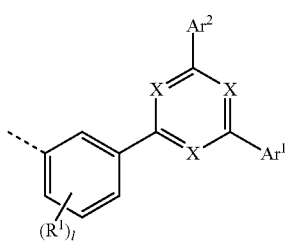
(L-I)

where
$Ar^1$, $Ar^2$ are each, independently of one another, an aryl or heteroaryl group, which may be substituted by one or more radicals R of any desired type,
X is in each case, independently of one another, N or $CR^2$, preferably CH,
$R^1$, $R^2$ are each, independently of one another, hydrogen, a straight-chain alkyl, alkoxy or thioalkoxy group having 1 to 40 C atoms or a branched or cyclic alkyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—X, in which X represents a halogen atom), a formyl group (—C(=O)—H), an isocyano group, an isocyanate group, a thiocyanate group or a thioisocyanate group, a hydroxyl group, a nitro group, a $CF_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$ and/or $R^2$ may form a mono- or polycyclic, aliphatic or aromatic ring system with one another and/or with the ring to which the group $R^1$ is bonded; and
l is 0, 1, 2, 3 or 4;
where the dashed bond indicates the bond to the functional structural element.

The present invention furthermore relates to a functional compound of the general formula (I)

(I)

where
A is a functional structural element,
B is a solubility-promoting structural element and
k is an integer in the range from 1 to 20,
which is characterised in that
the molecular weight of the functional compound is at least 550 g/mol and the solubility-promoting structural element B conforms to the formula (L-I)

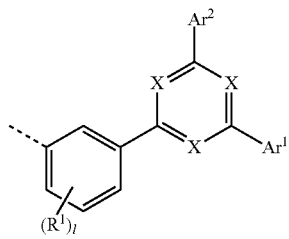
(L-I)

where
$Ar^1$, $Ar^2$ are each, independently of one another, an aryl or heteroaryl group, which may be substituted by one or more radicals R of any desired type,
X is in each case, independently of one another, N or $CR^2$, preferably CH,
$R^1$, $R^2$ are each, independently of one another, hydrogen, a straight-chain alkyl, alkoxy or thioalkoxy group having 1 to 40 C atoms or a branched or cyclic alkyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—X, in which X represents a halogen atom), a formyl group (—C(=O)—H), an isocyano group, an isocyanate group, a thiocyanate group or a thioisocyanate group, a hydroxyl group, a nitro group, a $CF_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$ and/or $R^2$ may form a mono- or polycyclic, aliphatic or aromatic ring system with one another and/or with the ring to which the group $R^1$ is bonded; and
l is 0, 1, 2, 3 or 4;
where the dashed bond indicates the bond to the functional structural element;
with the exception of compounds of the general formula (A-I)

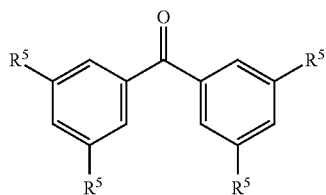
(A-I)

where the following applies to the symbols used:
$R^5$ is on each occurrence, identically or differently, hydrogen or an aromatic or heteroaromatic ring system having 5 to 60 aromatic ring atoms, which may be substituted by one or more radicals $R^6$, or an $N(Ar)_2$, $Si(Ar)_3$, C(=O)Ar, OAr, ArSO$_2$, P(Ar)$_2$, P(O)(Ar)$_2$ or B(Ar)$_2$ group;
$R^6$ is on each occurrence, identically or differently, H, D, F, Cl, Br, I, CHO, $N(Ar)_2$, C(=O)Ar, P(=O)(Ar)$_2$, S(=O)Ar, S(=O)$_2$Ar, $CR^7$=$CR^7$Ar, CN, NO$_2$, Si($R^8$)$_3$, B(OR$^8$)$_2$, B($R^8$)$_2$, B(N($R^8$)$_2$)$_2$, OSO$_2R^8$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^8$, where one or more non-adjacent $CH_2$ groups may be replaced by $R^8C=CR^8$, $C\equiv C$, $Si(R^8)_2$, $Ge(R^8)_2$, $Sn(R^8)_2$, $C=O$, $C=S$, $C=Se$, $C=NR^8$, $P(=O)(R^8)$, SO, $SO_2$, $NR^8$, O, S or $CONR^8$ and where one or more H atoms may be replaced by F, Cl, Br, I, ON or $NO_2$, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which may be substituted by one or more radicals $R^8$, or a combination of these systems;

$R^7$ is on each occurrence, identically or differently, H, D, F or a linear alkyl group having 1 to 20 C atoms or a branched or cyclic alkyl group having 3 to 20 C atoms; a plurality of radicals $R^7$ here may form a ring system with one another;

$R^8$ is on each occurrence, identically or differently, H, D or an aliphatic, aromatic and/or heteroaromatic hydrocarbon radical having 1 to 20 C atoms, in which, in addition, H atoms may be replaced by F; and Ar is on each occurrence, identically or differently, an aromatic or heteroaromatic ring system having 5 to 30 aromatic ring atoms, which may be substituted by one or more non-aromatic radicals $R^6$; two radicals Ar here which are bonded to the same nitrogen, phosphorus or boron atom may also be linked to one another by a single bond or a bridge selected from $B(R^8)$, $C(R^8)_2$, $Si(R^8)_2$, $C=O$, $C=NR^8$, $C=C(R^8)_2$, O, S, S=O, $SO_2$, $N(R^8)$, $P(R^8)$ and $P(=O)R^8$.

A BRIEF DESCRIPTION OF THE FIGURE

FIG. 1 illustrates a device configuration according to the invention.

A DETAILED DESCRIPTION OF THE INVENTION

A formulation according to the invention comprises at least one organic solvent. Suitable and preferred solvents are aliphatic, cycloaliphatic or aromatic hydrocarbons, amines, thiols, amides, nitriles, esters, ethers, polyethers, alcohols, diols and/or polyols.

The solvent preferably comprises at least one aromatic or heteroaromatic compound. The solvent particularly preferably comprises at least one aromatic hydrocarbon and/or halogenated aromatic compound, which particularly preferably contain(s) at least one alkyl group and/or cycloalkyl group having 1 to 8 carbon atoms, preferably having 1 to 6 carbon atoms. These include, in particular, toluene, dimethylbenzene (xylenes), trimethyl-benzenes, methylnaphthalenes, tetralin, cyclopentylbenzene and cyclohexylbenzene.

In accordance with a further embodiment of the present invention, use may be made of aromatic or heteroaromatic compounds which contain heteroatoms in the side group, in particular esters, ethers, nitriles and/or amides. The preferred compounds in this class include aromatic alkoxy compounds, such as, for example, 3-methylanisole, 2-isopropylanisole, 5-methoxy-indane, 2-ethoxynaphthalene, and aromatic esters, such as, for example, butyl benzoate and ethyl benzoate. Also suitable are heteroaromatic solvents containing an O, N or S atom in the aromatic ring, such as, for example, 2-methylindole and 6-methylquinoline.

The solvents employed can furthermore be heterocyclic compounds, such as, for example, 1-cyclohexyl-2-pyrrolidinone (N-cyclohexyl-pyrrolidinone).

Furthermore, alcohols represent a suitable class of solvents. The preferred alcohols include, in particular, alkyl-cyclohexanols, in particular methylated alicyclic alcohols (3- or 4-methylcyclohexanol or 2,5-dimethylcyclohexanol), naphthols, for example decahydro-2-naphthol or 1,2,3,4-tetrahydro-1-naphthol, terpenoids, such as, for example, α-terpineol, menthol or carveol, nonylphenol, 1-indanol and 2-indanol.

In addition, the solvents employed can be cycloalkanes, such as, for example, decalin.

The solvents can be employed individually or as a mixture of two, three or more compounds.

The preferred solvents include, inter alia, toluene, anisole, xylenes, methyl benzoate, dimethylanisoles, mesitylenes, tetralin, veratrol, tetrahydrofuran and chlorobenzene, and mixtures thereof. Particular preference is given to the use of aromatic solvents, in particular aromatic hydrocarbons. A formulation according to the invention can preferably comprise at least 50% by weight, particularly preferably at least 80% by weight and very particularly preferably at least 90% by weight, of aromatic solvent.

Surprising advantages can be achieved, in particular, by solvents whose Hansen solubility parameters are preferably in the following ranges:

$H_d$ (dispersion contribution) in the range from 17.0 to 23.2 $MPa^{0.5}$, particularly preferably in the range from 18.5 to 21.0 $MPa^{0.5}$;

$H_p$ (polar contribution) in the range from 0.2 to 12.5 $MPa^{0.5}$, particularly preferably in the range from 2.0 to 6.0 $MPa^{0.5}$, and $H_h$ (hydrogen bonding contribution) in the range from 0.9 to 14.2 $MPa^{0.5}$, particularly preferably in the range from 2.0 to 6.0 $MPa^{0.5}$. The Hansen solubility parameters can be determined using the "Hansen Solubility Parameters in Practice (HSPiP)" computer program ($2^{nd}$ Edition), provided by Hansen and Abbot et al.

Preferred functional compounds of the formula (I) may contain two, three or more of the solubility-promoting structural elements B. Accordingly, the index k in formula (I) can be an integer greater than or equal to 2, particularly preferably greater than or equal to 3.

Surprising advantages can be achieved, in particular, using functional compounds of the general formula (I) having a relatively high molecular weight. Thus, preferred functional compounds of the general formula (I) are distinguished by a molecular weight of at least 800 g/mol, particularly preferably at least 900 g/mol and very particularly preferably at least 950 g/mol.

Furthermore, preferred functional compounds of the formula (I) can have a molecular weight of at most 10000 g/mol, particularly preferably at most 5000 g/mol and very particularly preferably at most 3000 g/mol.

Of particular interest are furthermore functional compounds which are distinguished by a high glass-transition temperature. In this connection, particular preference is given to functional compounds of the general formula (I) which have a glass-transition temperature of at least 70° C., particularly preferably at least 100° C., very particularly preferably at least 125° C. and especially preferably at least 150° C., determined in accordance with DIN 51005.

The functional structural element A of the functional compound of the formula (I) is not subject to any particular limitation, and consequently the present invention is suitable for converting known substances which are employed in electronic devices in order to achieve functional properties into a soluble form without thereby modifying the original electronic properties of the known substances in an unacceptable manner.

These are, inter alia, those as disclosed and extensively listed in WO 02/077060 A1 and in WO 2005/014689 A2. These are considered to be part of the present invention by way of reference. The functional structural elements A can originate, for example, from the following classes:

Group 1: units which are able to generate hole-injection and/or hole-transport properties;
Group 2: units which are able to generate electron-injection and/or electron-transport properties;
Group 3: units which have light-emitting properties;
Group 4: units which can serve as host materials or co-host materials;
Group 5: units which improve the transfer from the so-called singlet state to the triplet state.

Structural elements from group 1 which have hole-injection and/or hole-transport properties are, for example, triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives and further O—, S— or N— containing heterocycles having a high HOMO (HOMO=highest occupied molecular orbital).

As structural elements from group 1 which have hole-injection and/or hole-transport properties, particular mention may be made of phenylenediamine derivatives (U.S. Pat. No. 3,615,404), arylamine derivatives (U.S. Pat. No. 3,567,450), amino-substituted chalcone derivatives (U.S. Pat. No. 3,526,501), styrylanthracene derivatives (JP-A-56-46234), polycyclic aromatic compounds (EP 1009041), polyarylalkane derivatives (U.S. Pat. No. 3,615,402), fluorenone derivatives (JP-A-54-110837), hydrazone derivatives (U.S. Pat. No. 3,717,462), acylhydrazones, stilbene derivatives (JP-A-61-210363), silazane derivatives (U.S. Pat. No. 4,950,950), polysilanes (JP-A-2-204996), aniline copolymers (JP-A-2-282263), thiophene oligomers (JP Heisei 1 (1989) 211399), polythiophenes, poly(N-vinylcarbazole) (PVK), polypyrroles, polyanilines and other electrically conducting macromolecules, porphyrin compounds (JP-A-63-2956965, U.S. Pat. No. 4,720,432), aromatic dimethylidene-type compounds, carbazole compounds, such as, for example, CDBP, CBP, mCP, aromatic tertiary amine and styrylamine compounds (U.S. Pat. No. 4,127,412), such as, for example, triphenylamines of the benzidine type, triphenylamines of the styrylamine type and triphenylamines of the diamine type. It is also possible to use arylamine dendrimers (JP Heisei 8 (1996) 193191), monomeric triarylamines (U.S. Pat. No. 3,180,730), triarylamines containing one or more vinyl radicals and/or at least one functional group containing active hydrogen (U.S. Pat. Nos. 3,567,450 and 3,658,520), or tetraaryldiamines (the two tertiary amine units are connected via an aryl group). More triarylamino groups may also be present in the molecule. Phthalocyanine derivatives, naphthalocyanine derivatives, butadiene derivatives and quinoline derivatives, such as, for example, dipyrazino[2,3-f:2',3'-h]quinoxalinehexacarbonitrile, are also suitable.

Preference is given to aromatic tertiary amines containing at least two tertiary amine units (US 2008/0102311 A1, U.S. Pat. Nos. 4,720,432 and 5,061,569), such as, for example, NPD (α-NPD=4,4'-bis[N-(1-naphthyl)-N-phenylamino]biphenyl) (U.S. Pat. No. 5,061,569), TPD 232 (=N,N'-bis-(N,N'-diphenyl-4-aminophenyl)-N,N-diphenyl-4,4'-diamino-1,1'-biphenyl) or MTDATA (MTDATA or m-MTDATA=4,4',4"-tris[3-methylphenyl)phenylamino]-triphenylamine)(JP-A-4-308688), TBDB (=N,N,N',N'-tetra(4-biphenyl)-diaminobiphenylene), TAPC (=1,1-bis(4-di-p-tolylaminophenyl)cyclohexane), TAPPP (=1,1-bis(4-di-p-tolylaminophenyl)-3-phenylpropane), BDTAPVB (=1,4-bis[2-[4-[N,N-di(p-tolyl)amino]phenyl]vinyl]benzene), TTB (=N,N,N',N'-tetra-p-tolyl-4,4'-diaminobiphenyl), TPD (=4,4'-bis[N-3-methylphenyl]-N-phenylamino)biphenyl), N,N,N',N'-tetraphenyl-4,4'''-diamino-1,1',4',1'',4'',1'''-quaterphenyl, likewise tertiary amines containing carbazole units, such as, for example, TCTA (=4-(9H-carbazol-9-yl)-N,N-bis[4-(9H-carbazol-9-yl)phenyl]phenylamine). Preference is likewise given to hexaazatriphenylene compounds in accordance with US 2007/0092755 A1 and phthalocyanine derivatives (for example H₂Pc, CuPc (=copper phthalocyanine), CoPc, NiPc, ZnPc, PdPc, FePc, MnPc, ClAlPc, ClGaPc, ClInPc, ClSnPc, Cl₂SiPc, (HO)AlPc, (HO)GaPc, VOPc, TiOPc, MoOPc, GaPc-O-GaPc).

TPD 232

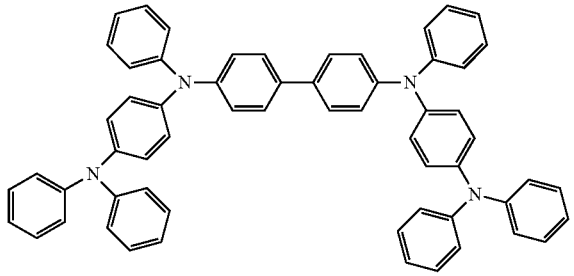

Particular preference is given to the following triarylamine compounds, which may also be substituted:

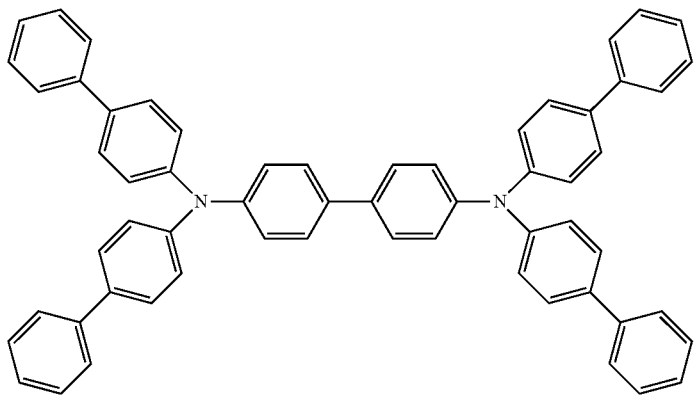

TBDB: EP 1162193 B1 and EP 650955 B1

-continued
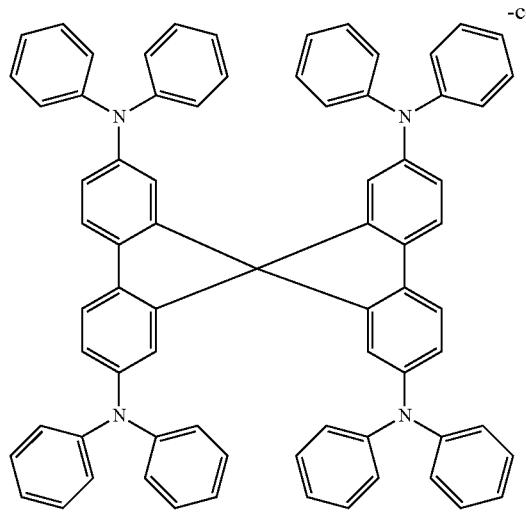
Synth. Metals 1997, 91(1-3), 209 and DE 19646119 A1
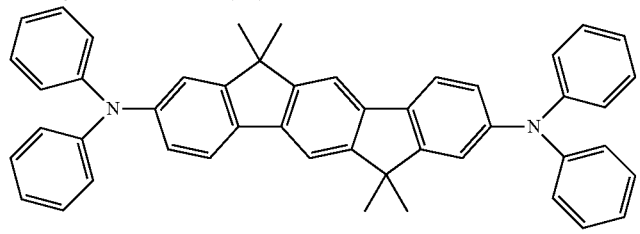
WO 2006 122630 A1 and EP 1860097 A1
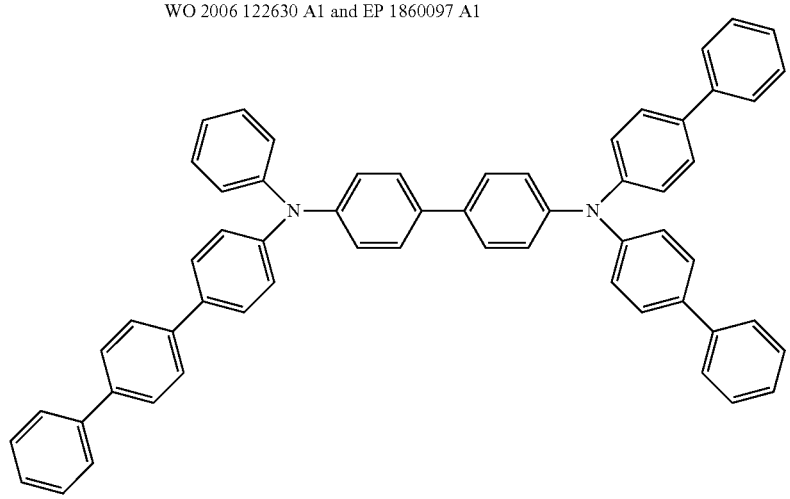
EP 1834945 A1
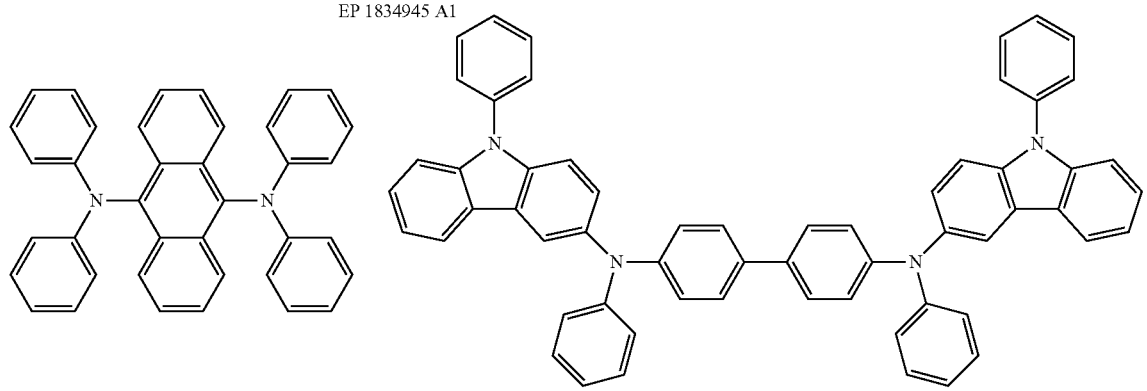
JP 08053397 A and US 6251531 B1    EP 1661888

-continued
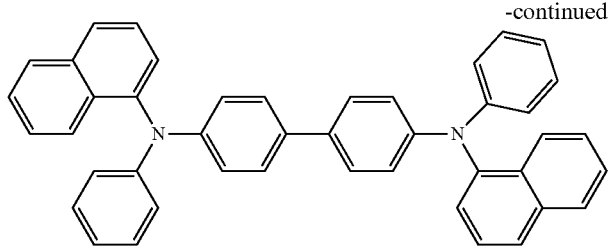
NPB = alpha-NPD
NPB = 4,4'-bis[N-(1-naphthyl)-N-phenylamino]biphenyl
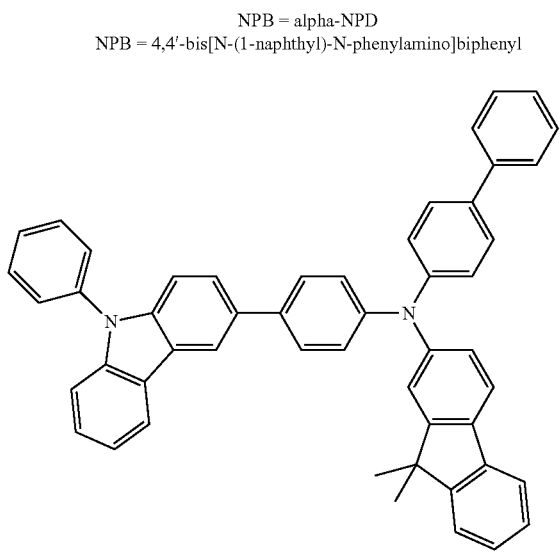
US 2005/0221124, WO 09/041635
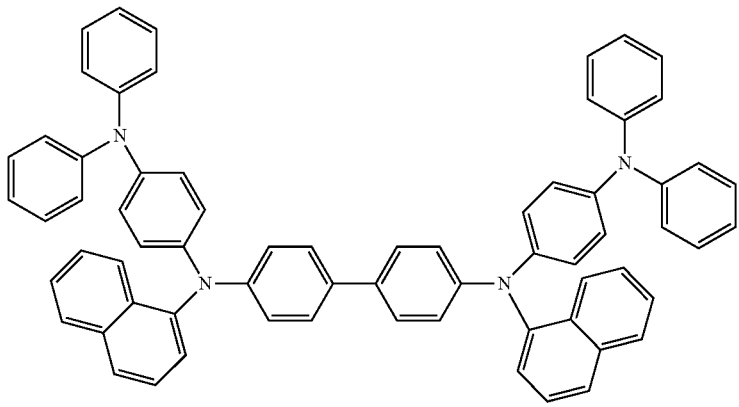
US 7399537 B2, US 2006 0061265 A1
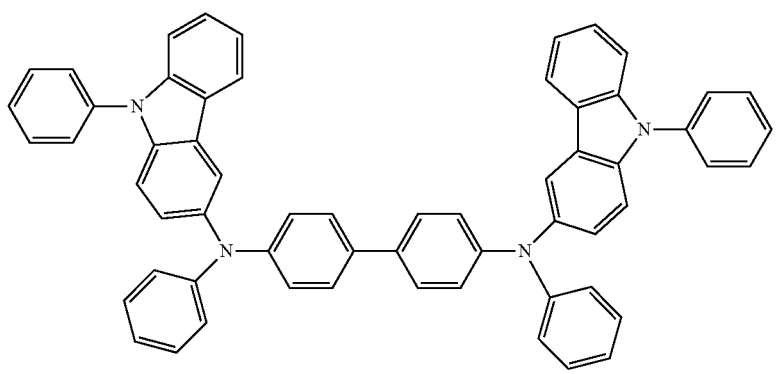
EP 1661888 B1

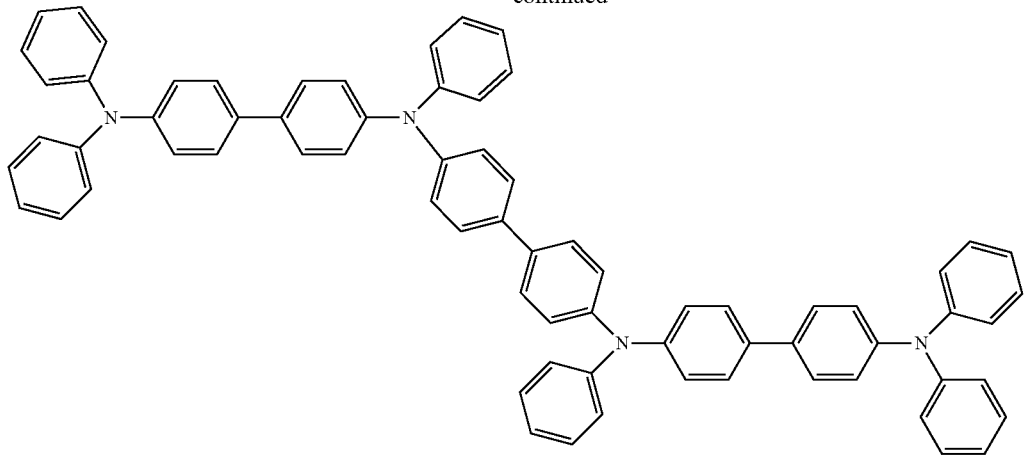

JP 08292586 A

Further structural elements which can be employed as hole-injection materials are described in EP 0891121 A1 and EP 1029909 A1, injection layers in general in US 2004/0174116 A1.

These arylamines and heterocycles which are generally employed as structural elements from group 1 preferably result in an HOMO in the polymer of greater than −5.8 eV (vs. vacuum level), particularly preferably greater than −5.5 eV.

Structural elements from group 2 which have electron-injection and/or electron-transport properties are, for example, pyridine, pyrimidine, pyridazine, pyrazine, oxadiazole, quinoline, quinoxaline, anthracene, benzanthracene, pyrene, perylene, benzimidazole, triazine, ketone, phosphine oxide and phenazine derivatives, but also triarylboranes and further O—, S— or N— containing heterocycles having a low LUMO (LUMO=lowest unoccupied molecular orbital).

Particularly suitable structural elements for electron-transporting and electron-injecting layers are metal chelates of 8-hydroxyquinoline (for example LIQ, AlQ$_3$, GaQ$_3$, MgQ$_2$, ZnQ$_2$, InQ$_3$, ZrQ$_4$). BAlQ, Ga oxinoid complexes, 4-azaphenanthren-5-ol-Be complexes (U.S. Pat. No. 5,529,853 A),

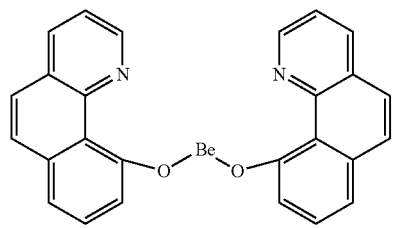

butadiene derivatives (U.S. Pat. No. 4,356,429), heterocyclic optical brighteners (U.S. Pat. No. 4,539,507), benzimidazole derivatives (US 2007/0273272 A1), such as, for example, TPBI (U.S. Pat. No. 5,766,779),

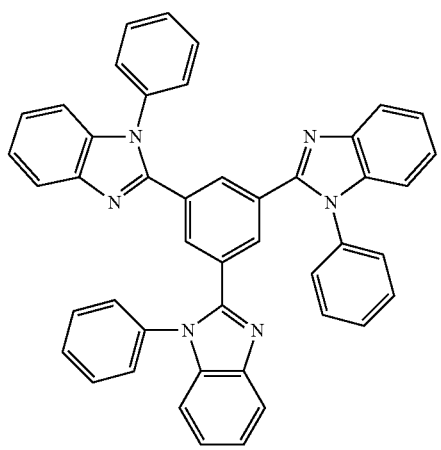

TPBI 2,2′,2″-(1,3,5-benzenetriyl)tris(1-phenyl-1H-benzimidazole)

1,3,5-triazines, for example spirobifluorenyltriazine derivatives (for example in accordance with DE 102008064200), pyrenes, anthracenes, tetracenes, fluorenes, spirofluorenes, dendrimers, tetracenes (for example rubrene derivatives), 1,10-phenanthroline derivatives (JP 2003-115387, JP 2004-311184, JP-2001-267080, WO 2002/043449), silacyclopentadiene derivatives (EP 1480280, EP 1478032, EP 1469533), borane derivatives, such as, for example, triarylborane derivatives containing Si,

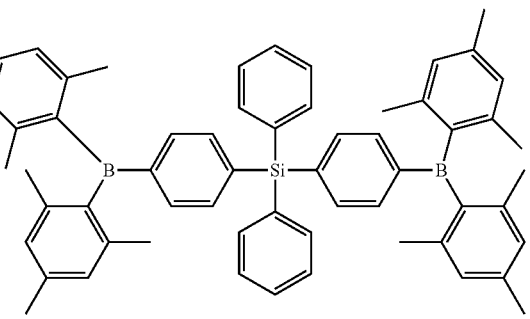

US 2007/0087219 A1 pyridine derivatives (JP 2004-200162), phenanthrolines, especially 1,10-phenanthroline derivatives, such as, for example, BCP and Bphen, also several phenanthrolines connected via biphenyl or other aromatic groups (US-2007-0252517 A1) or phenanthrolines connected to anthracene (US 2007-0122656 A1).

imidazoles or oxadiazoles. Examples of the use of five-membered rings containing N, such as, for example, oxazoles, thiazoles, oxadiazoles, thiadiazoles, triazoles, inter alia, see US 2008/0102311 A1. Preferred compounds are the following:

triazoles, for example

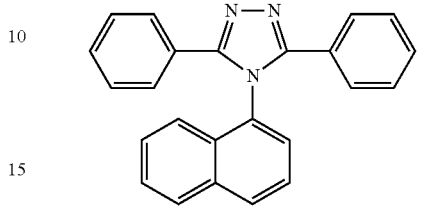

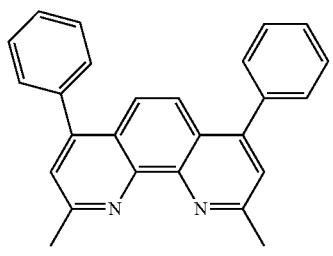

Bathocuproin

Y. A. Levin, M. S. Skorobogatova, Khimiya Geterotsiklicheskikh Soedinenii 1967 (2), 339-341

1,3,4-oxadiazoles, for example

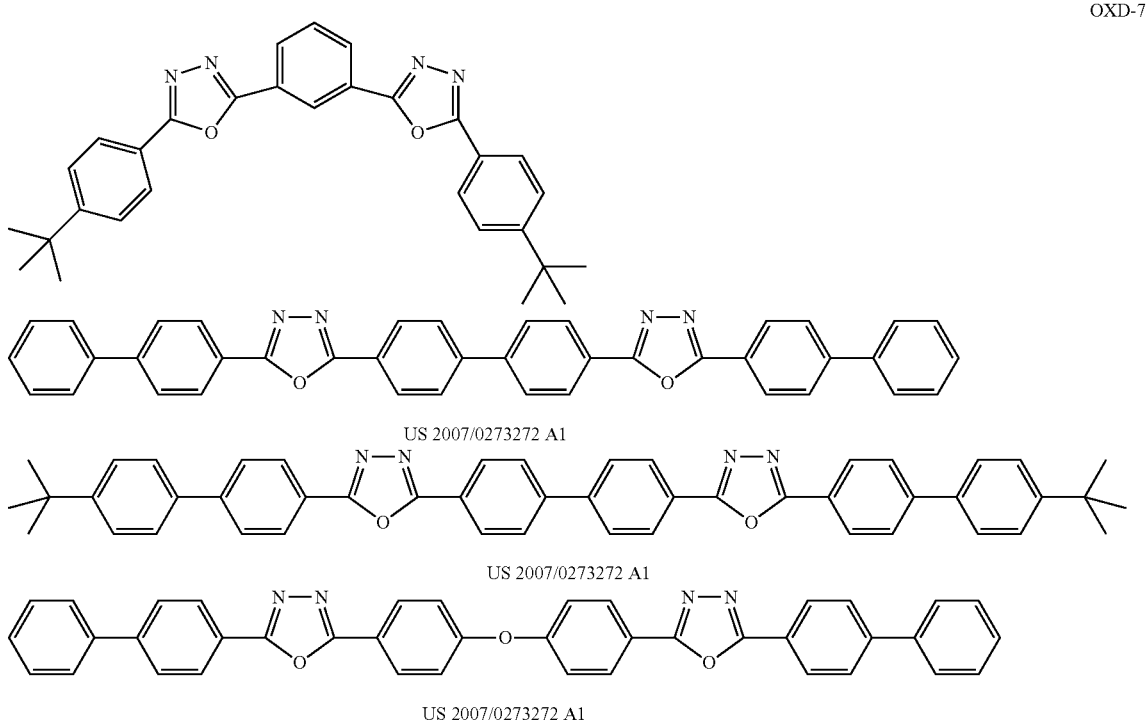

OXD-7

US 2007/0273272 A1

US 2007/0273272 A1

US 2007/0273272 A1

-continued

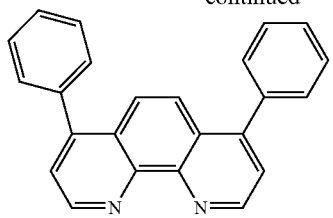

Bphen

Likewise suitable are heterocyclic organic compounds, such as, for example, thiopyran dioxides, oxazoles, triazoles, It is also possible to employ organic compounds, such as derivatives of fluorenone, fluorenylidenemethane, perylenetetracarbonic acid, anthraquinonedimethane, diphenoquinone, anthrone and anthraquinonediethylenediamine.

Preference is given to 2,9,10-substituted anthracenes (with 1- or 2-naphthyl and 4- or 3-biphenyl) or molecules which contain two anthracene units (US2008/0193796 A1). Also very advantageous is the connection of 9,10-substituted anthracene units to benzimidazole derivatives.

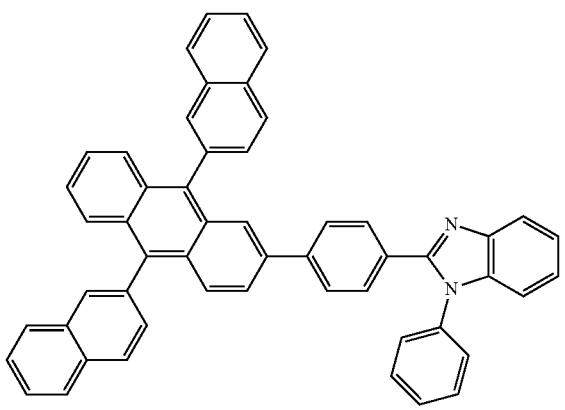

US 6878469 B2

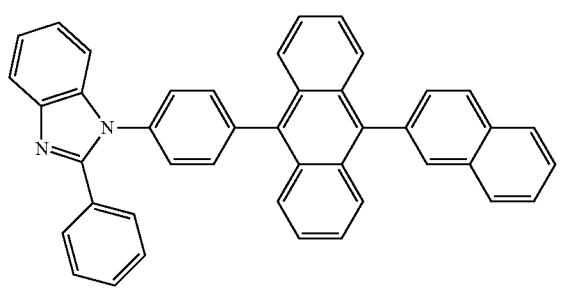

US 2006 147747 A

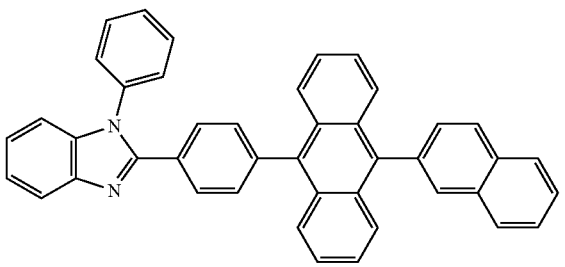

EP 1551206 A1

The structural elements from group 2 in a compound of the formula (I) to be employed in accordance with the invention preferably result in an LUMO of less than −2.5 eV (vs. vacuum level), particularly preferably less than −2.7 eV.

Structural elements from group 3 are those which are able to emit light. These include, inter alia, compounds containing stilbene, stilbenamine, styrylamine, coumarine, rubrene, rhodamine, thiazole, thiadiazole, cyanine, thiophene, paraphenylene, perylene, phthalocyanine, porphyrin, ketone, quinoline, imine, anthracene and/or pyrene structures. Particular preference is given to compounds which are able to emit light from the triplet state with high efficiency, even at room temperature, i.e. exhibit electrophosphorescence instead of electrofluorescence, which frequently causes an increase in the energy efficiency. Suitable for this purpose are firstly compounds which contain heavy atoms having an atomic number of greater than 36. Preference is given to compounds which contain d- or f-transition metals which satisfy the above-mentioned condition. Particular preference is given here to corresponding structural elements which contain elements from groups 8 to 10 (Ru, Os, Rh, Ir, Pd, Pt). Suitable functional structural elements A for the compounds of the formula (I) here are, for example, various complexes, as described, for example, in WO 02/068435 A1, WO 02/081488 A1, EP 1239526 A2 and WO 04/026886 A2.

Preferred structural elements which can serve as fluorescent emitters are described by way of example below. Preferred structural elements from group 3 are selected from the class of the monostyrylamines, the distyrylamines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or an aromatic amine in the sense of the present invention is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 2,6- or 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Further preferred structural elements from group 3 are selected from indenofluorenamines or indenofluorenediamines, for example in accordance with WO 06/122630, benzoindenofluorenamines or benzoindenofluorenediamines, for example in accordance with WO 08/006449, and dibenzoindenofluorenamines or dibenzoindenofluorenediamines, for example in accordance with WO 07/140847.

Examples of structural elements from group 3 from the class of the styrylamines are substituted or unsubstituted tristilbenamines or the dopants described in WO 06/000388, WO 06/058737, WO 06/000389, WO 07/065549 and WO 07/115610. Distyrylbenzene and distyrylbiphenyl derivatives are described in U.S. Pat. No. 5,121,029. Further styrylamines can be found in US 2007/0122656 A1.

Particularly preferred styrylamine structural elements from group 3 are:
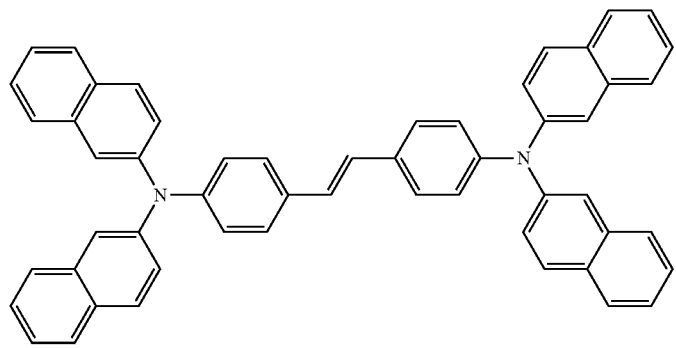
US 7250532 B2
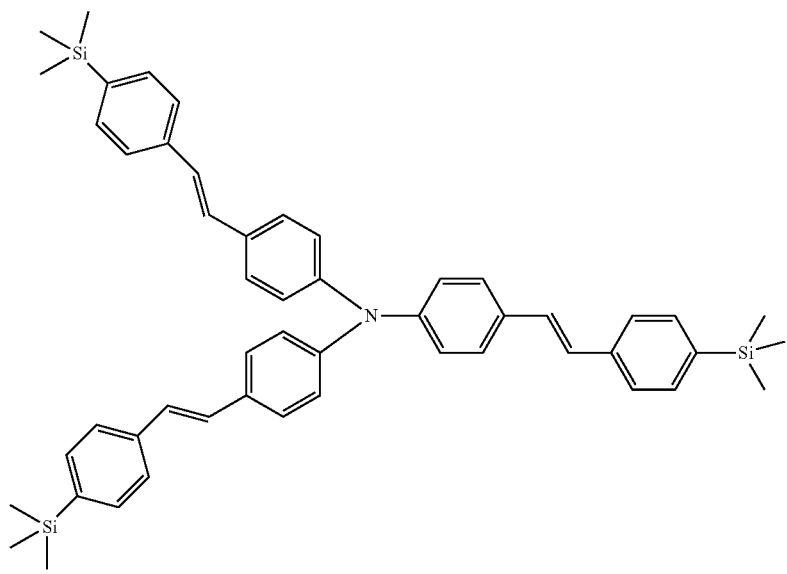
DE 10 2005 058557 A1
Particularly preferred triarylamine structural elements from group 3 are:
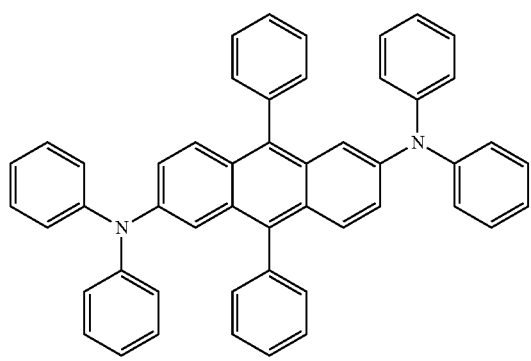
CN 1583691 A
-continued
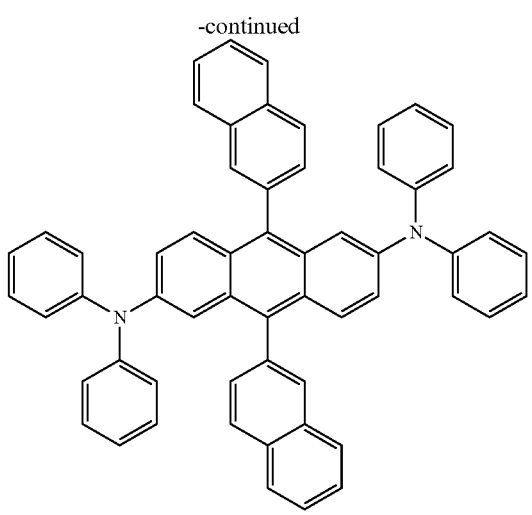
CN 1583691 A

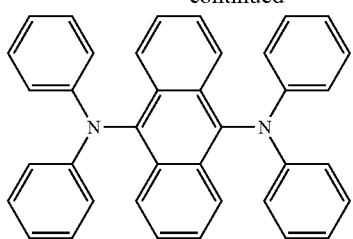
JP 08/053397 A and US 6251531 B1, derivatives in
EP 1957606 A1 and US 2008/0113101 A1.
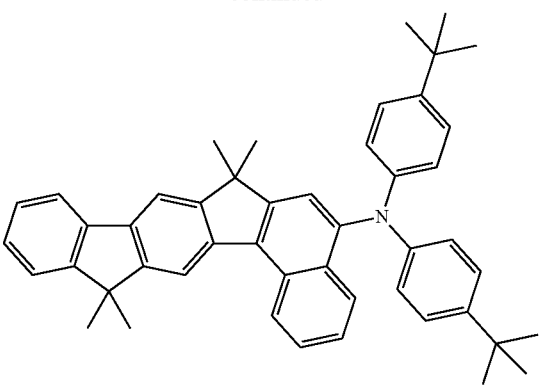
WO 08/006449
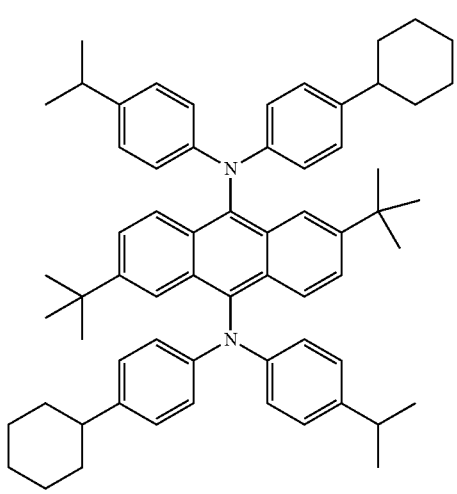
EP 1957606 A1
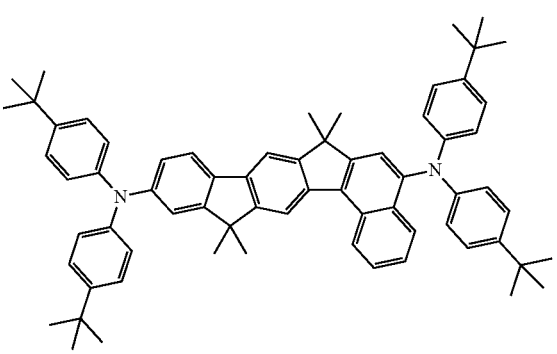
WO 08/006449
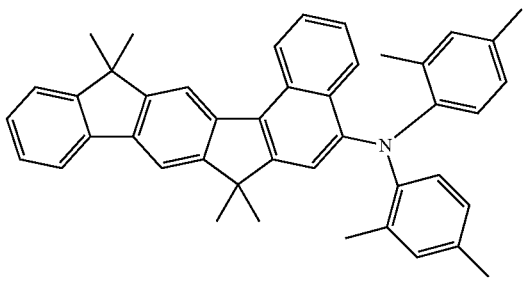
WO 08/006449
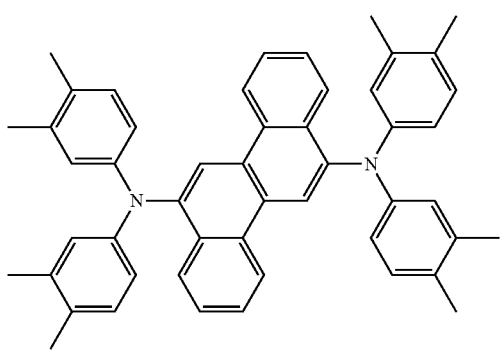
US 2006/210830 A
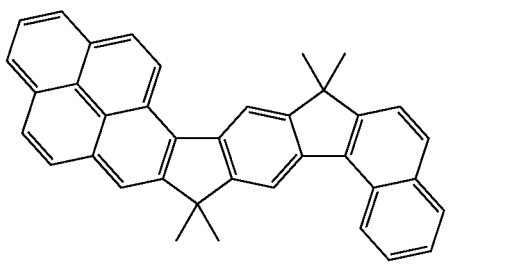
DE 102008035413
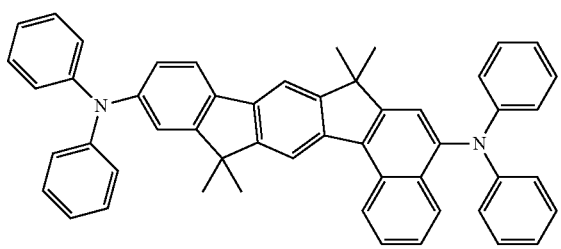
WO 08/006449
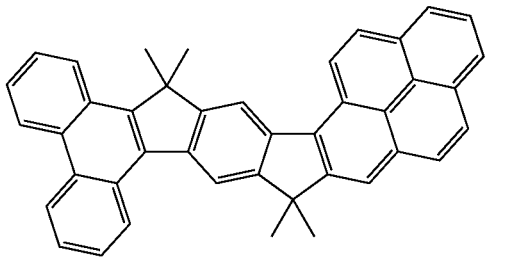
DE 102008035413

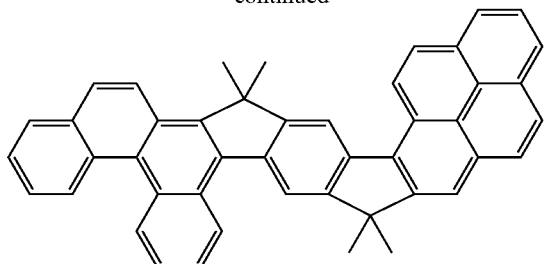

DE 102008035413

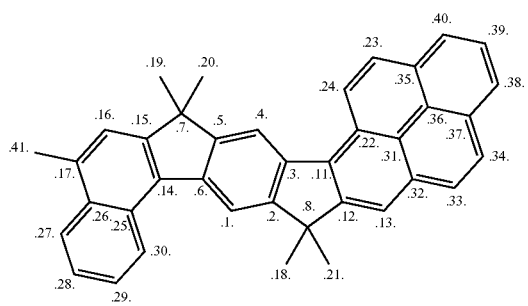

DE 102008035413

Further preferred structural elements from group 3 are selected from derivatives of naphthalene, anthracene, tetracene, benzanthracene, benzophenanthrene (DE 10 2009 005746), fluorene, fluoranthene, perk flanthene, indenoperylene, phenanthrene, perylene (US 2007/0252517 A1), pyrene, chrysene, decacyclene, coronene, tetraphenylcyclopentadiene, pentaphenylcyclopentadiene, fluorene, spirofluorene, rubrene, coumarine (U.S. Pat. Nos. 4,769,292, 6,020,078, US 2007/0252517 A1), pyran, oxazole, benzoxazole, benzothiazole, benzimidazole, pyrazine, cinnamic acid esters, diketopyrrolopyrrole, acridone and quinacridone (US 2007/0252517 A1).

Of the anthracene compounds, particular preference is given to 9,10-substituted anthracenes, such as, for example, 9,10-diphenylanthracene and 9,10-bis(phenylethynyl)anthracene. 1,4-Bis(9'-ethynylanthracenyl)benzene is also a preferred dopant.

Preference is likewise given to derivatives of rubrene, coumarine, rhodamine, quinacridone, such as, for example, DMQA (=N,N'-dimethylquinacridone), dicyanomethylenepyran, such as, for example, DCM (=4-(dicyano-ethylene)-6-(4-dimethylaminostyryl-2-methyl)-4H-pyran), thiopyran, polymethine, pyrylium and thiapyrylium salts, periflanthene and indenoperylene.

Blue fluorescent emitters are preferably polyaromatic compounds, such as, for example, 9,10-di(2-naphthylanthracene) and other anthracene derivatives, derivatives of tetracene, xanthene, perylene, such as, for example, 2,5,8,11-tetra-t-butylperylene, phenylene, for example 4,4'-bis(9-ethyl-3-carbazovinylene)-1,1'-biphenyl, fluorene, fluoranthene, arylpyrenes (US 2006/0222886 A1), arylenevinylenes (U.S. Pat. Nos. 5,121,029, 5,130,603), bis(azinyl)imine-boron compounds (US 2007/0092753 A1), bis(azinyl)methene compounds and carbostyryl compounds.

Further preferred blue fluorescent emitters are described in C. H. Chen et al.: "Recent developments in organic electroluminescent materials" Macromol. Symp. 125, (1997) 1-48 and "Recent progress of molecular organic electroluminescent materials and devices" Mat. Sci. and Eng. R, 39 (2002), 143-222.

Further preferred blue-fluorescent emitters are the hydrocarbons disclosed in DE 102008035413.

Preferred structural elements from group 3 which can serve as phosphorescent emitters are depicted by way of example below.

Examples of phosphorescent emitters are revealed by WO 00/70655, WO 01/41512, WO 02/02714, WO 02/15645, EP 1191613, EP 1191612, EP 1191614 and WO 05/033244. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

Phosphorescent metal complexes preferably contain Ir, Ru, Pd, Pt, Os or Re.

Preferred ligands are 2-phenylpyridine derivatives, 7,8-benzoquinoline derivatives, 2-(2-thienyl)pyridine derivatives, 2-(1-naphthyl)pyridine derivatives, 1-phenylisoquinoline derivatives, 3-phenylisoquinoline derivatives or 2-phenylquinoline derivatives. All these compounds may be substituted, for example by fluoro, cyano and/or trifluoromethyl substituents for blue. Auxiliary ligands are preferably acetylacetonate or picolinic acid.

Particularly suitable are complexes of Pt or Pd with tetradentate ligands,

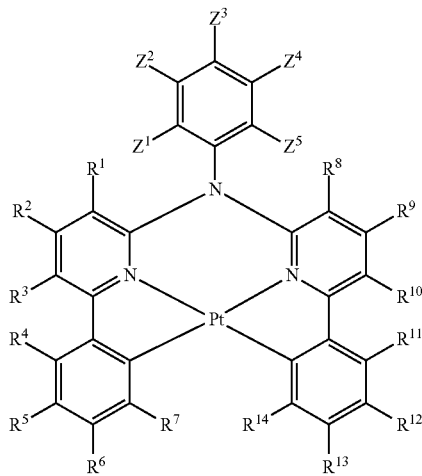

(US 2007/0087219 A1, where, for disclosure purposes, reference is made to this specification for an explanation of the substituents and indices in the above formula), Pt-porphyrin complexes having an enlarged ring system (US 2009/0061681 A1) and Ir complexes, for example 2,3,7,8,12,13,17,18-octaethyl-21H, 23H-porphyrin-Pt(II), tetraphenyl-Pt(II) tetrabenzoporphyrin (US 2009/0061681 A1), cis-bis(2-phenylpyridinato-N,C$^{2'}$)Pt(II), cis-bis(2-(2'-thienyl)pyridinato-N,C$^{3'}$)Pt(II), cis-bis(2-(2'-thienyl)quinolinato-N,C$^{5'}$)Pt(II), (2-(4,6-difluorophenyl)pyridinato-N,C$^{2'}$)Pt(II) (acetylacetonate), or tris(2-phenylpyridinato-N,C$^{2'}$)Ir(III) (=Ir(ppy)$_3$, green), bis(2-phenylpyridinato-N,C$^2$)Ir(III) (acetylacetonate) (=Ir(ppy)$_2$ acetylacetonate, green, US 2001/0053462 A1, Baldo, Thompson et al. Nature 403, (2000), 750-753), bis(1-phenylisoquinolinato-N,C$^{2'}$)(2-phenylpyridinato-N,C$^{2'}$)iridium(III), bis(2-phenylpyridinato-N, C$^{2'}$)(1-phenylisoquinolinato-N,C$^{2'}$)iridium(III), bis(2-(2'-benzothienyl)pyridinato-N,C$^{3'}$)iridium(III) (acetylacetonate), bis(2-(4',6'-difluorophenyl)pyridinato-N,C$^{2'}$)iridium(III) (piccolinate) (FIrpic, blue), bis(2-(4',6'-difluorophenyl)pyridinato-N,C$^{2'}$)Ir(III) (tetrakis(1-pyrazolyl) borate), tris(2-(biphenyl-3-yl)-4-tert-butylpyridine)iridium (III), (ppz)$_2$Ir(5phdpym) (US 2009/0061681 A1), (45ooppz)$_2$Ir(5phdpym) (US 2009/0061681 A1), derivatives of 2-phenylpyridine-Ir complexes, such as, for example, PQIr (=iridium(III) bis(2-phenylquinolyl-N,C$^{2'}$)acetylacetonate), tris(2-phenylisoquinolinato-N,C)Ir(III) (red), bis(2-(2'-benzo[4,5-a]thienyl)pyridinato-N,C$^3$)Ir (acetylacetonate) ([Btp$_2$Ir(acac)], red, Adachi et al. Appl. Phys. Lett. 78 (2001), 1622-1624).

Likewise suitable are complexes of trivalent lanthanides, such as, for example, Tb$^{3+}$ and Eu$^{3+}$ (J, Kido et al. Appl. Phys. Lett. 65 (1994), 2124, Kido et al. Chem. Lett. 657, 1990, US 2007/0252517 A1), or phosphorescent complexes of Pt(II), Ir(I), Rh(I) with maleonitriledithiolate (Johnson et al., JACS 105, 1983, 1795), Re(I) tricarbonyl-diimine complexes (Wrighton, JACS 96, 1974, 998, inter alia), Os(II) complexes with cyano ligands and bipyridyl or phenanthroline ligands (Ma et al., Synth. Metals 94, 1998, 245).

Further phosphorescent emitters having tridentate ligands are described in U.S. Pat. No. 6,824,895 and U.S. Ser. No. 10/729,238. Red-emitting phosphorescent complexes are found in U.S. Pat. Nos. 6,835,469 and 6,830,828.

Particularly preferred structural elements which are used as phosphorescent dopants are:

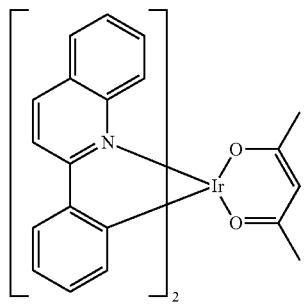

US 2001/0053462 A1 and Inorg. Chem., 2001, 40(7), 1704-1711, JACS 2001, 123(18), 4304-4312.

Derivatives are described in U.S. Pat. No. 7,378,162 B2, U.S. Pat. No. 6,835,469 B2 and JP 2003/253145 A.

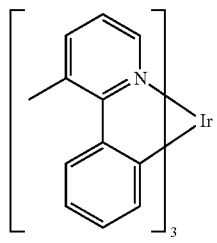

US 7238437 B2

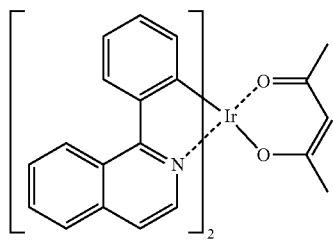

US 2009/008607 A1

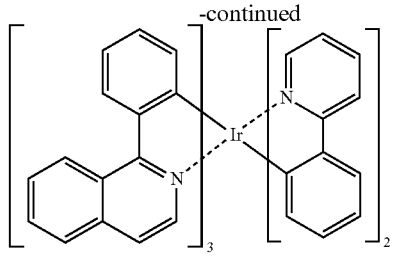

US 2009/008607 A1

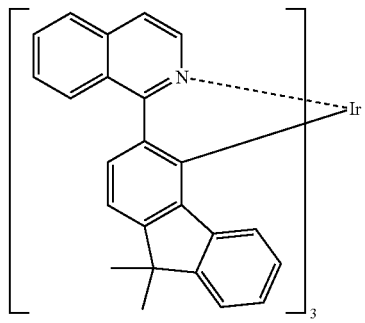

EP 1348711

Structural elements from group 4 which are employed as host materials, in particular together with emitting compounds, include materials from various classes of substance.

Preferred structural elements from group 4 which are employed, in particular, together with fluorescent dopants are selected from the classes of the oligoarylenes (for example 2,2',7,7'-tetraphenylspirobifluorene in accordance with EP 676461 or dinaphthylanthracene), in particular the oligoarylenes containing condensed aromatic groups, such as, for example, anthracene, benzanthracene, benzophenanthrene (DE 10 2009 005746, WO 09/069566), phenanthrene, tetracene, coronene, chrysene, fluorene, spirofluorene, perylene, phthaloperylene, naphthaloperylene, decacyclene, rubrene, the oligoarylenevinylenes (for example DPVBi=4, 4'-bis(2,2-diphenylethenyl)-1,1'-biphenyl or spiro-DPVBi in accordance with EP 676461), the polypodal metal complexes (for example in accordance with WO 04/081017), in particular metal complexes of 8-hydroxyquinoline, for example AlQ$_3$ (=aluminium(III) tris(8-hydroxyquinoline)) or bis(2-methyl-8-quinolinolato)-4-(phenylphenolinolato) aluminium, also with imidazole chelate (US 2007/0092753 A1) and the quinoline-metal complexes, aminoquinoline-metal complexes, benzoquinoline-metal complexes, the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145239).

Particularly preferred structural elements from group 4 are selected from the classes of the oligoarylenes, comprising anthracene, benzanthracene and/or pyrene, or atropisomers of these compounds. An oligoarylene in the sense of the present invention is intended to be taken to mean a compound in which at least three aryl or arylene groups are bonded to one another.

Preferred host materials are selected, in particular, from compounds of the formula (H-1),

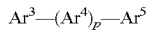 (H-1)

where Ar³, Ar⁴, Ar⁵ are on each occurrence, identically or differently, an aryl or heteroaryl group having 5 to 30 aromatic ring atoms, which may be substituted by one or more radicals R¹, and R¹ has the same meaning as described above, and p represents an integer in the range from 1 to 5; the sum of the π electrons in Ar³, Ar⁴ and Ar⁵ is at least 30 if p=1 and at least 36 if p=2 and at least 42 if p=3.

In the compounds of the formula (H-1), the group Ar⁴ particularly preferably stands for anthracene, which may be substituted by one or more radicals R¹, and the groups Ar³ and Ar⁵ are bonded in the 9- and 10-position. Very particularly preferably, at least one of the groups Ar³ and/or Ar⁵ is a condensed aryl group selected from 1- or 2-naphthyl, 2-, 3- or 9-phenanthrenyl or 2-, 3-, 4-, 5-, 6- or 7-benzanthracenyl, each of which may be substituted by one or more radicals R¹. Anthracene-based compounds are described in US 2007/0092753 A1 and US 2007/0252517 A1, for example 2-(4-methylphenyl)-9,10-di-(2-naphthyl)anthracene, 9-(2-naphthyl)-10-(1,1'-biphenyl)anthracene and 9,10-bis[4-(2,2-diphenylethenyl)phenyl]anthracene, 9,10-diphenylanthracene, 9,10-bis(phenylethynyl)anthracene and 1,4-bis(9-ethynylanthracenyl)benzene. Preference is also given to compounds containing two anthracene units (US 2008/0193796 A1), for example 10,10'-bis[1,1',4',1"]terphenyl-2-yl-9,9'-bisanthracenyl.

Further preferred compounds are derivatives of arylamine, styrylamine, fluorescein, diphenylbutadiene, tetraphenylbutadiene, cyclopentadienes, tetraphenylcyclopentadiene, pentaphenylcyclopentadiene, coumarine, oxadiazole, bisbenzoxazoline, oxazole, pyridine, pyrazine, imine, benzothiazole, benzoxazole, benzimidazole (US 2007/0092753 A1), for example 2,2',2"-(1,3,5-phenylene)tris[1-phenyl-1H-benzimidazole], aldazine, stilbene, styrylarylene derivatives, for example 9,10-bis[4-(2,2-diphenylethenyl)phenyl] anthracene, and distyrylarylene derivatives (U.S. Pat. No. 5,121,029), diphenylethylene, vinylanthracene, diaminocarbazole, pyran, thiopyran, diketopyrrolopyrrole, polymethine, cinnamic acid esters and fluorescent dyes.

Particular preference is given to derivatives of arylamine and styrylamine, for example TNB (=4,4'-bis[N-(1-naphthyl)-N-(2-naphthyl)amino]biphenyl). Metal-oxinoid complexes, such as LiQ or AlQ₃, can be used as co-hosts.

Preferred compounds with oligoarylene as matrix:

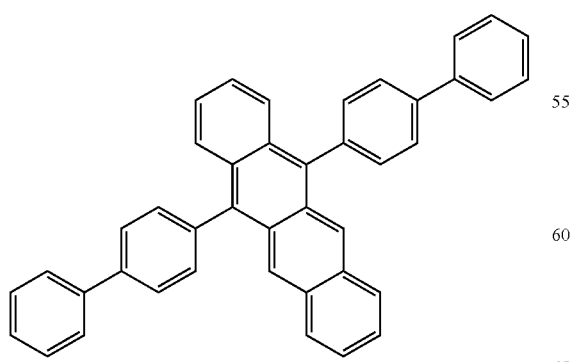

US 2003/0027016 A1

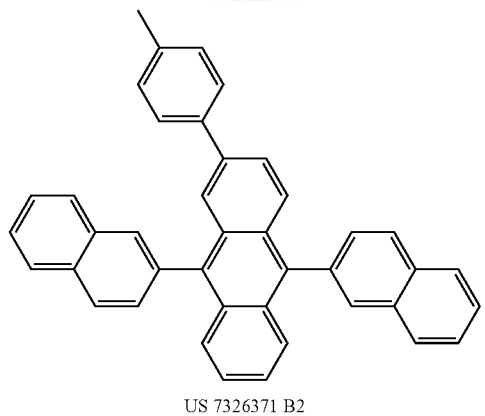

US 7326371 B2

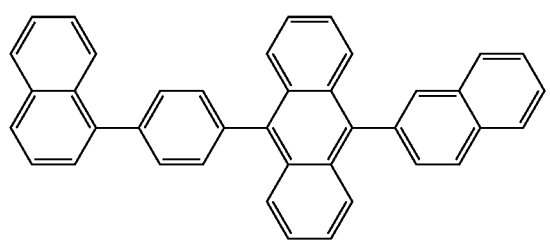

US 2006/043858 A

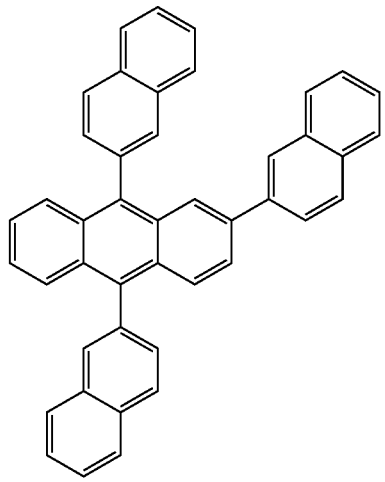

US 7326371 B2

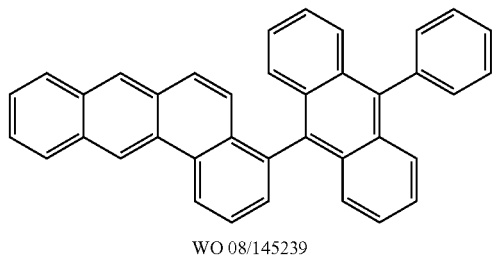

WO 08/145239

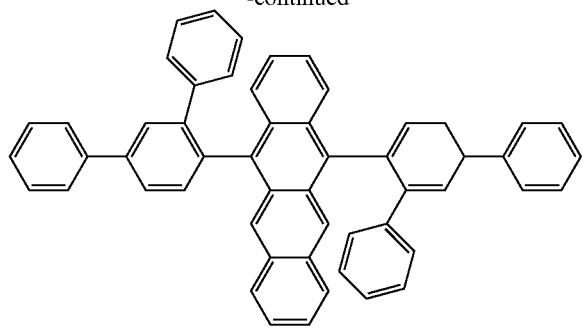

US 2003/0027016 A1

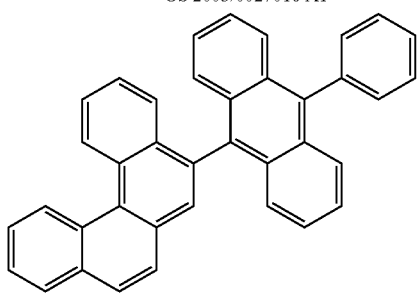

DE 102009005746

Furthermore, structural elements from group 4 include materials which are employed together with phosphorescent emitters. These structural elements include CBP (N,N-bis-carbazolylbiphenyl), carbazole derivatives (for example in accordance with WO 05/039246, US 2005/0069729, JP 2004/288381, EP 1205527 or WO 08/086851), azacarbazoles (for example in accordance with EP 1617710, EP 1617711, EP 1731584, JP 2005/347160), ketones (for example in accordance with WO 04/093207 or in accordance with DE 102008033943), phosphine oxides, sulfoxides and sulfones (for example in accordance with WO 05/003253), oligophenylenes, aromatic amines (for example in accordance with US 2005/0069729), bipolar matrix materials (for example in accordance with WO 07/137725), silanes (for example in accordance with WO 05/111172), 9,9-diarylfluorene derivatives (for example in accordance with DE 102008017591), azaboroles or boronic esters (for example in accordance with WO 06/117052), triazine derivatives (for example in accordance with DE 102008036982), indolocarbazole derivatives (for example in accordance with WO 07/063754 or WO 08/056746), indenocarbazole derivatives (for example in accordance with DE 102009023155 and DE 102009031021), diazaphosphole derivatives (for example in accordance with DE 102009022858), triazole derivatives, oxazoles and oxazole derivatives, imidazole derivatives, polyarylalkane derivatives, pyrazoline derivatives, pyrazolone derivatives, distyrylpyrazine derivatives, thiopyran dioxide derivatives, phenylenediamine derivatives, tertiary aromatic amines, styrylamines, amino-substituted chalcone derivatives, indoles, hydrazone derivatives, stilbene derivatives, silazane derivatives, aromatic dimethylidene compounds, carbodiimide derivatives, metal complexes of 8-hydroxyquinoline derivatives, such as, for example, AlQ$_3$, which may also contain triarylaminophenol ligands (US 2007/0134514 A1), metal complex/polysilane compounds, and thiophene, benzothiophene and dibenzothiophene derivatives.

Examples of preferred carbazole structural elements are mCP (=1,3-N,N-dicarbazolylbenzene (=9,9'-(1,3-phenylene)bis-9H-carbazole)), CDBP (=9,9'-(2,2'-dimethyl[1,1'-biphenyl]-4,4'-diyl)bis-9H-carbazole), 1,3-bis(N,N'-dicarbazolyl)benzene (=1,3-bis(carbazol-9-yl)benzene) PVK (polyvinylcarbazole), 3,5-di(9H-carbazol-9-yl)biphenyl, and the compounds depicted below.

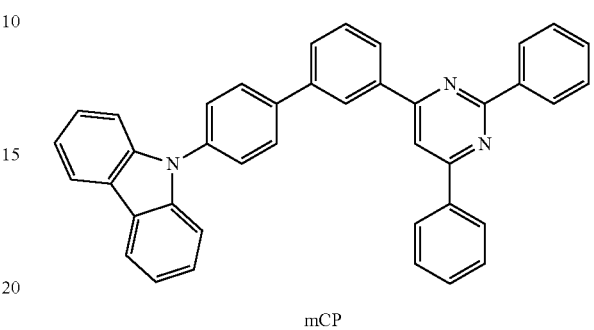

mCP

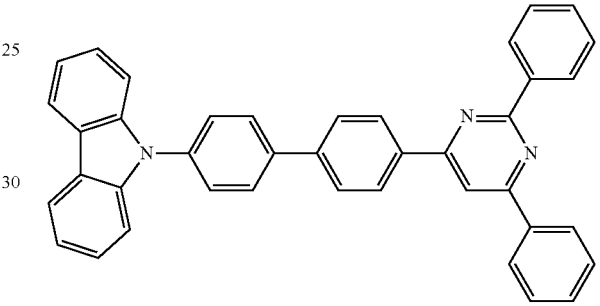

US 2005/0249976 A1

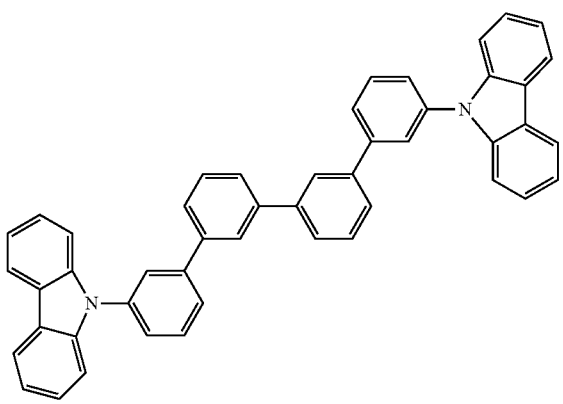

CMTTP

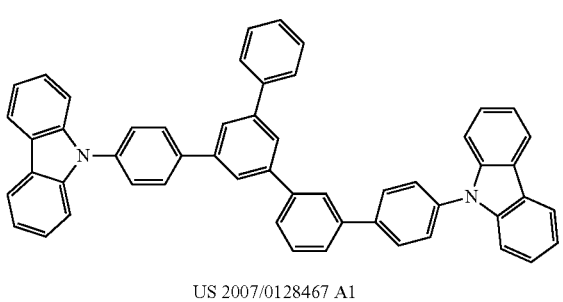

US 2007/0128467 A1

-continued
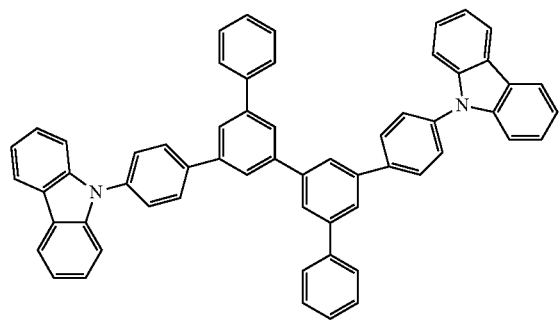
US 2007/0128467 A1
Preferred Si tetraaryl compounds are, for example, (US 2004/0209115, US 2004/0209116)
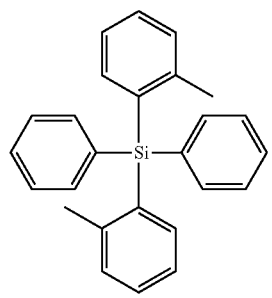
UGH1
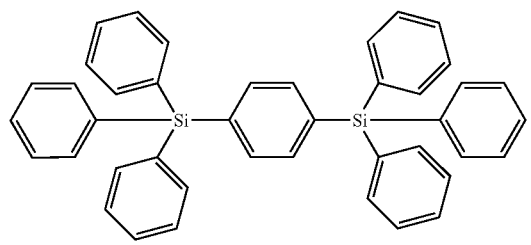
UGH2
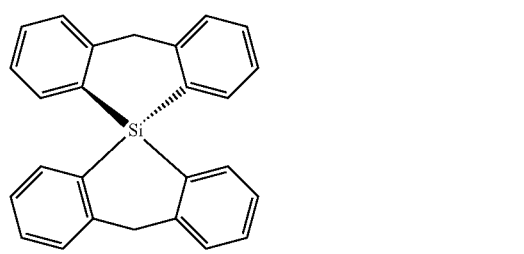
UGH4
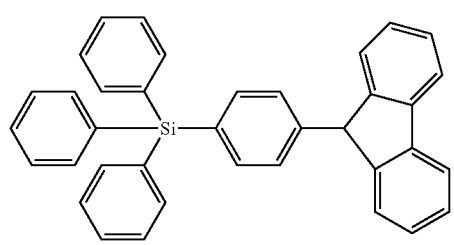
TPSi-F
Triphenyl-[4-(9-phenyl-9H-fluoren-9-yl)phenyl]silane
-continued
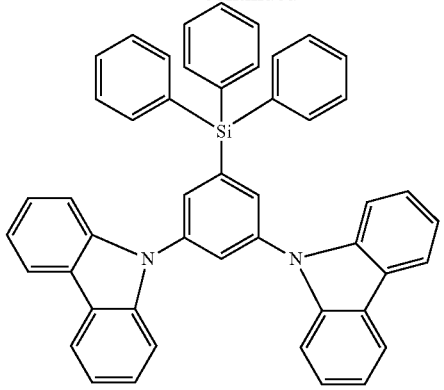
SimCP
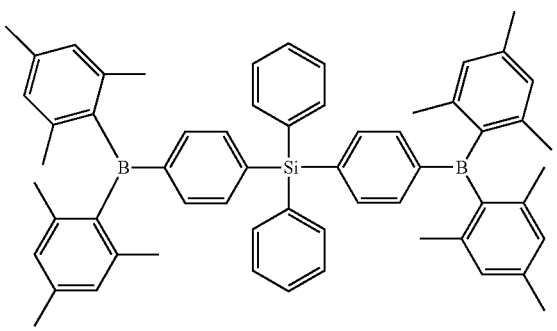
US 2007/0087219 A1
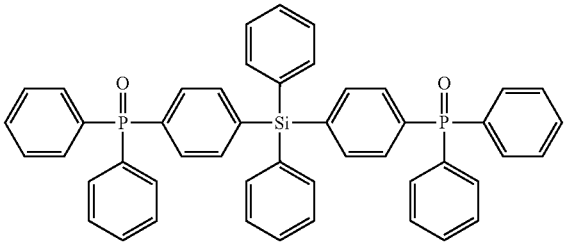
US 2007/0087219 A1
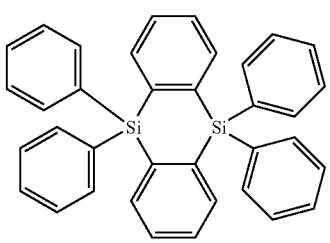
H. Gilman, E. A. Zuech, Chemistry & Industry (London, United Kingdom), 1960, 120.
Particularly preferred structural elements from group 4 for the preparation of the matrix for phosphorescent dopants are:

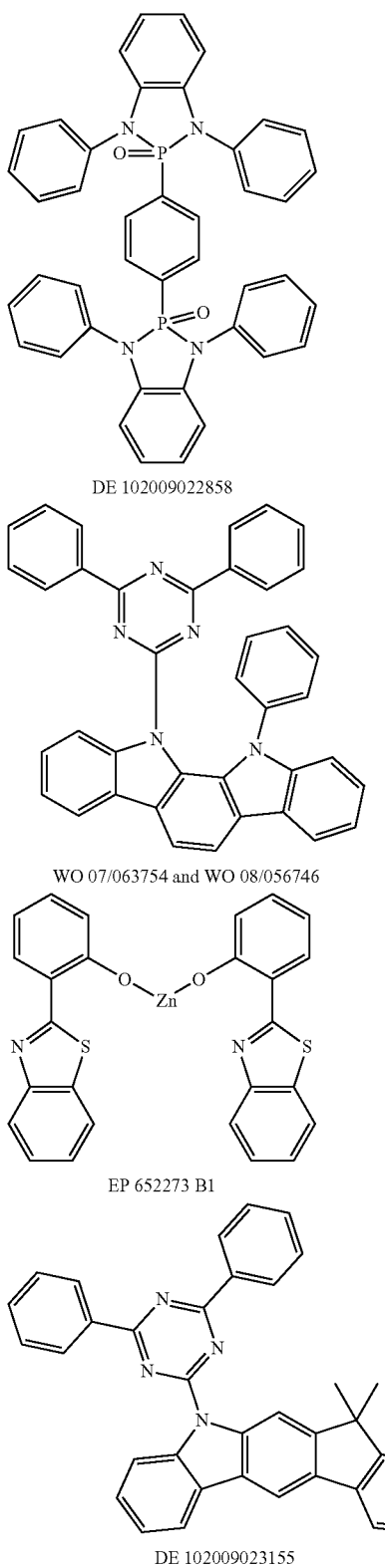

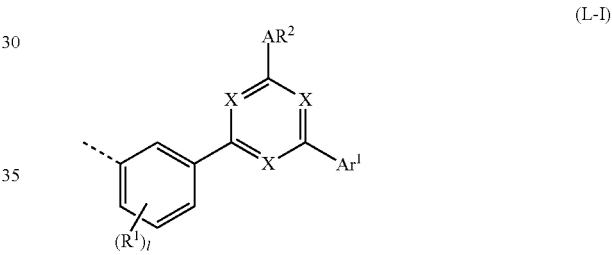

Structural elements from group 5 are those which improve the transfer from the singlet state to the triplet state and which, employed in support of the functional structural elements from group 3, improve the phosphorescence properties of these structural elements. Suitable for this purpose are, in particular, carbazole and bridged carbazole dimer units, as described, for example, in WO 04/070772 A2 and WO 04/113468 A1. Also suitable for this purpose are ketones, phosphine oxides, sulfoxides, sulfones, silane derivatives and similar compounds, as described, for example, in WO 05/040302 A1.

The publications cited above for the description of the functional structural elements are incorporated into the present application by way of reference for disclosure purposes.

The functional structural elements A described above can preferably be connected to at least one solubility-promoting structural element B via an aromatic and/or heteroaromatic group. The bonding site is generally not important, meaning that one or more bonds to at least one of the solubility-promoting structural elements B described below are present, but are not depicted in the formulae shown above for reasons of clarity. According to a particular aspect, the functional structural elements A described above can be connected to one or more solubility-promoting structural elements B via a carbon atom of an aromatic or heteroaromatic ring system.

Besides at least one functional structural element A, a compound according to the invention contains at least one solubility-promoting structural element B of the formula (L-I)

(L-I)

where $Ar^1$, $Ar^2$ are each, independently of one another, an aryl or heteroaryl group, which may be substituted by one or more radicals R of any desired type, X is in each case, independently of one another, N or $CR^2$, preferably CH, $R^1$, $R^2$ are each, independently of one another, hydrogen, a straight-chain alkyl, alkenyl, alkoxy or thioalkoxy group having 1 or 2 to 40 C atoms respectively or a branched or cyclic alkyl, alkenyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—X, in which X represents a halogen atom), a formyl group (—C(=O)—H), an isocyano group, an isocyanate group, a thiocyanate group or a thioisocyanate group, a hydroxyl group, a nitro group, a $CF_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$ and/or $R^2$ may form a mono- or polycyclic, aliphatic or aromatic ring system with one another and/or with the ring to which the group $R^1$ is bonded; and l is 0, 1, 2, 3 or 4;

where the dashed bond indicates the bond to the functional structural element A.

The solubility-promoting structural element B can preferably conform to the general formula (L-II)

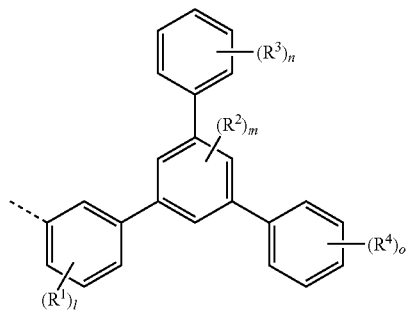
(L-II)

where
R$^1$, R$^2$, R$^3$, R$^4$ are each, independently of one another, hydrogen, a straight-chain alkyl, alkenyl, alkoxy or thioalkoxy group having 1 or 2 to 40 C atoms respectively or a branched or cyclic alkyl, alkenyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a formyl group (—C(=O)—H), a CF$_3$ group, Cl, Br, F, a cross-linkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups R$^1$, R$^2$, R$^3$ and/or R$^4$ may form a mono- or polycyclic, aliphatic or aromatic ring system with one another and/or with the ring to which the group R$^1$ is bonded; and l is 0, 1, 2, 3 or 4,
m is 0, 1, 2 or 3, and
n, o are each, independently of one another, 0, 1, 2, 3, 4 or 5;

where the dashed bond indicates the bond to the functional structural element.

The radicals R$^1$, R$^2$, R$^3$, R$^4$ particularly preferably represent hydrogen (l, m, n and o=0), a straight-chain alkyl or alkoxy group having 1 to 20 C atoms or a branched alkyl or alkoxy group having 3 to 20 C atoms.

The particularly preferred solubility-promoting structural elements B include, inter alia, the structural elements of the following formulae:

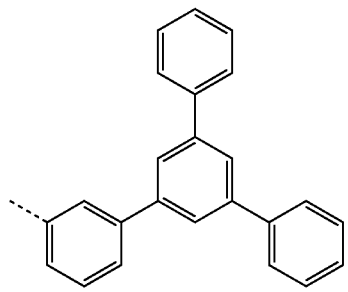
(L-IIa)

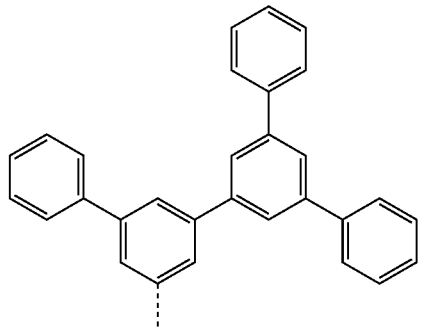
(L-IIb)

where the dashed bond indicates the bond to the functional structural element A.

Very particular preference is given to the following solubility-promoting structural elements B:

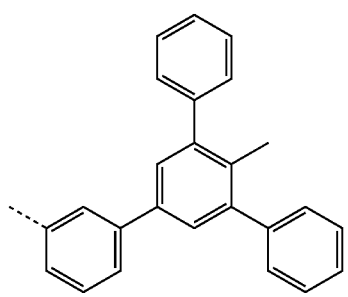
(L-IIa1)

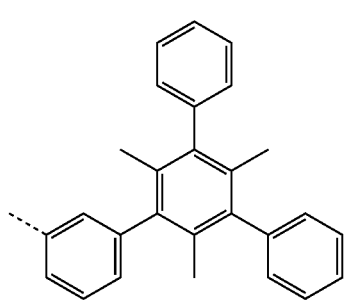
(L-IIa2)

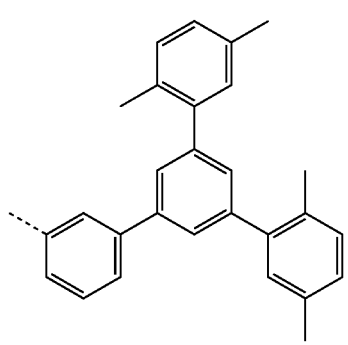
(L-IIa3)

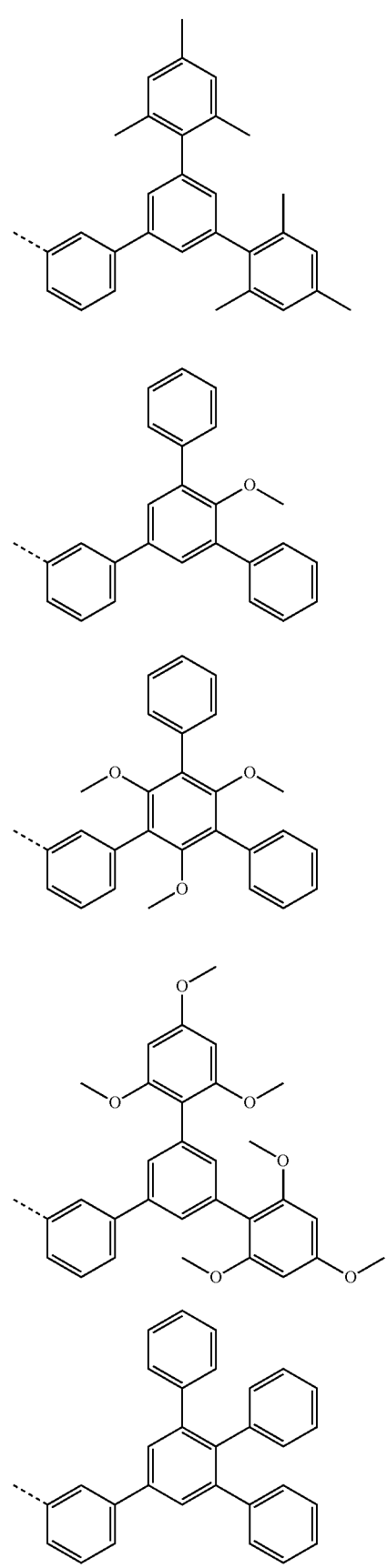
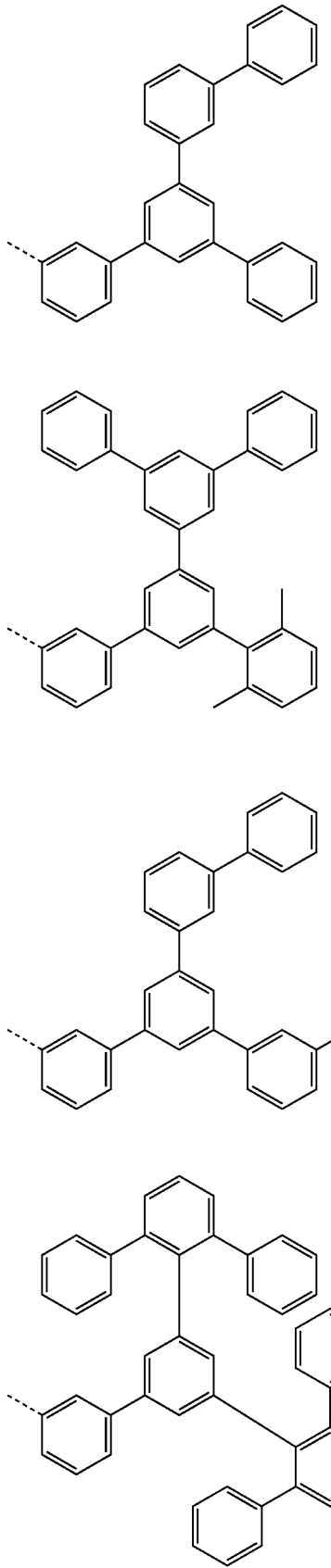

(L-IIb1)

(L-IIb2)

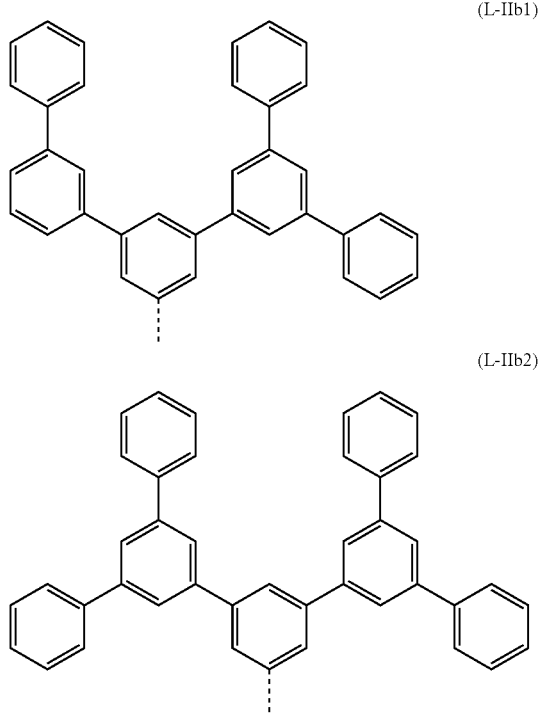

where the dashed bond indicates the bond to the functional structural element A.

An aromatic or heteroaromatic ring system having 5 to 60 ring atoms, which may also in each case be substituted by any desired radicals R and which may be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole, benzanthrene, benzanthracene, rubicene and triphenylene. For the purposes of the present invention, particular preference is given to fluorene, spirobifluorene, indenofluorene, anthracene, phenanthrene, dihydrophenanthrene and carbazole.

An aryl group in the sense of the present invention contains 5 to 60 C atoms; a heteroaryl group in the sense of the present invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, or a condensed aryl or heteroaryl group, for example naphthalene, anthracene, phenanthrene, quinoline, isoquinoline, benzothiophene, benzofuran and indole.

In the structural units of the general formulae (L-I) and (L-II), it is furthermore preferred for $R^1$ and $R^2$, and $R^1$, $R^2$, $R^3$ and $R^4$ respectively to be selected on each occurrence, independently of one another, from F, Cl, Br, I, $N(Ar)_2$, $N(R')_2$, CN, $NO_2$, $Si(R')_3$, $B(OR')_2$, C(=O)Ar, C(=O)R', P(=O)(Ar)_2, P(=O)(R')_2, S(=O)Ar, S(=O)R', $S(=O)_2$Ar, $S(=O)_2$R', —CR'=CR'Ar, $OSO_2$R', a straight-chain alkyl, alkoxy or thioalkoxy group having 1 to 40 C atoms, preferably 1 to 20 C atoms, or a branched or cyclic alkyl, alkoxy or thioalkoxy group having 3 to 40 C atoms, preferably 3 to 20 C atoms, each of which may be substituted by one or more radicals R', where one or more non-adjacent $CH_2$ groups may be replaced by R'C=CR', C≡C, $Si(R')_2$, $Ge(R')_2$, $Sn(R')_2$, C=O, C=S, C=Se, C=NR', P(=O)(R'), SO, $SO_2$, NR', O, S or CONR' and where one or more H atoms may be replaced by F, Cl, Br, I, CN or $NO_2$, a crosslinkable group or an aromatic or heteroaromatic ring system having 5 to 60 ring atoms, which may in each case be substituted by one or more radicals R', or an aryloxy or heteroaryloxy group having 5 to 60 ring atoms, which may be substituted by one or more radicals R', or a combination of these systems, where two or more substituents R may also form a mono- or polycyclic, aliphatic or aromatic ring system with one another, where R' is in each case, independently of one another, H or an aliphatic or aromatic hydrocarbon radical having 1 to 20 C atoms, and Ar is an aryl or heteroaryl group having 2 to 30 C atoms.

The structural units of the general formulae (L-I) and (L-II) may, as described above, contain one or more crosslinkable groups. "Crosslinkable group" means a functional group which is capable of reacting irreversibly. A crosslinked material, which is insoluble, is thereby formed. The crosslinking can usually be supported by heat or by UV, microwave, X-ray or electron radiation. Little by-product formation occurs during the crosslinking here. In addition, the crosslinkable groups which may be present in the functional compounds crosslink very easily, meaning that smaller amounts of energy are necessary for the crosslinking (for example <200° C. in the case of thermal crosslinking).

Examples of crosslinkable groups are units which contain a double bond, a triple bond, a precursor which is capable of in-situ formation of a double or triple bond, or a heterocyclic addition-polymerisable radical. Crosslinkable groups include, inter alia, vinyl, alkenyl, preferably ethenyl and propenyl, $C_{4-20}$-cycloalkenyl, azide, oxirane, oxetane, di(hydrocarbyl)amino, cyanate ester, hydroxyl, glycidyl ether, $C_{1-10}$-alkyl acrylate, $C_{1-10}$alkyl methacrylate, alkenyloxy, preferably ethenyloxy, perfluoroalkenyloxy, preferably perfluoro-ethenyloxy, alkynyl, preferably ethynyl, maleimide, tri($C_{1-4}$)-alkylsiloxy and tri($C_{1-4}$)-alkylsilyl. Particular preference is given to vinyl and alkenyl.

For the purposes of the present invention, an alkyl group having 1 to 40 C atoms, in which, in addition, individual H atoms or $CH_2$ groups may be substituted by the above-mentioned groups or radicals R, is preferably taken to mean the radicals methyl, ethyl, n-propyl, i-propyl, cyclopropyl, n-butyl, i-butyl, s-butyl, t-butyl, cyclobutyl, 2-methylbutyl, n-pentyl, s-pentyl, cyclopentyl, n-hexyl, cyclohexyl, n-heptyl, cycloheptyl, n-octyl, cyclooctyl, 2-ethyl-hexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl and octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy or 2-methylbutoxy.

According to a particular aspect of the present invention, the weight ratio of structural element A to structural element B in formula (I) is preferably in the range from 2:1 to 1:20 and particularly preferably in the range from 1:1 to 1:3.

The functional compounds of the formula (I) present in the formulations according to the invention can be prepared using known methods, in which starting materials containing reactive groups are reacted. These reactive starting materials contain the above-described structural units of the above formulae and at least in each case one leaving group, such as, for example, bromine, iodine, boronic acid or boronic acid ester.

Suitable reactions for the formation of C—C links are known to the person skilled in the art and are described in the literature. Particularly suitable and preferred coupling reactions, all of which result in C—C links, are SUZUKI, YAMAMOTO, STILLE, HECK, NEGISHI, SONOGASHIRA and HIYAMA coupling reactions.

According to a preferred embodiment of the present invention, compounds of the general formula (A-I)

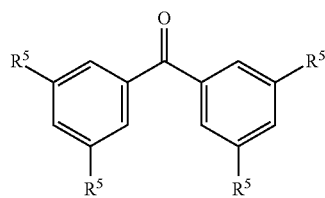

(A-I)

particularly preferably of the formula (A-II)

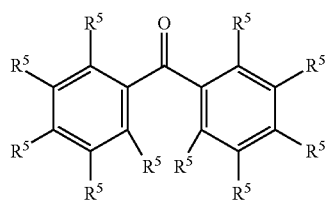

(A-II)

are excluded from the invention, where the following applies to the symbols used;

$R^5$ is on each occurrence, identically or differently, hydrogen or an aromatic or heteroaromatic ring system having 5 to 60 aromatic ring atoms, which may be substituted by one or more radicals $R^6$, or an $N(Ar)_2$, $Si(Ar)_3$, $C(=O)Ar$, $OAr$, $ArSO$, $ArSO_2$, $P(Ar)_2$, $P(O)(Ar)_2$ or $B(Ar)_2$ group;

$R^6$ is on each occurrence, identically or differently, H, D, F, Cl, Br, I, CHO, $N(Ar)_2$, $C(=O)Ar$, $P(=O)(Ar)_2$, $S(=O)Ar$, $S(=O)_2Ar$, $CR^7=CR^7Ar$, CN, $NO_2$, $Si(R^8)_3$, $B(OR^8)_2$, $B(R^8)_2$, $B(N(R^8)_2)_2$, $OSO_2R^8$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^8$, where one or more non-adjacent $CH_2$ groups may be replaced by $R^8C=CR^8$, $C\equiv C$, $Si(R^8)_2$, $Ge(R^8)_2$, $Sn(R^8)_2$, $C=O$, $C=S$, $C=Se$, $C=NR^8$, $P(=O)(R^8)$, SO, $SO_2$, $NR^8$, O, S or $CONR^8$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which may be substituted by one or more radicals $R^8$, or a combination of these systems;

$R^7$ is on each occurrence, identically or differently, H, D, F or a linear alkyl group having 1 to 20 C atoms or a branched or cyclic alkyl group having 3 to 20 C atoms; a plurality of radicals $R^7$ here may form a ring system with one another;

$R^7$ is on each occurrence, identically or differently, H, D or an aliphatic, aromatic and/or heteroaromatic hydrocarbon radical having 1 to 20 C atoms, in which, in addition, H atoms may be replaced by F; and Ar is on each occurrence, identically or differently, an aromatic or heteroaromatic ring system having 5 to 30 aromatic ring atoms, which may be substituted by one or more non-aromatic radicals $R^6$; two radicals Ar here which are bonded to the same nitrogen, phosphorus or boron atom may also be linked to one another by a single bond or a bridge selected from $B(R^8)$, $C(R^8)_2$, $Si(R^8)_2$, $C=O$, $C=NR^8$, $C=C(R^8)_2$, O, S, $S=O$, $SO_2$, $N(R^8)$, $P(R^8)$ and $P(=O)R^8$.

According to a particularly preferred embodiment, compounds of the formula (A-III):

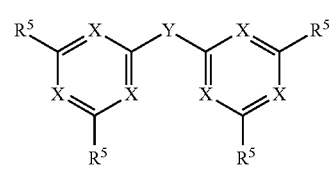

(A-III)

are excluded from the present invention, where the following applies to the symbols used:

Y is $C=O$ or $C(R^7)_2$;

X is on each occurrence, identically or differently, $CR^9$ or N;

$R^5$ has the meaning given above in relation to formula (A-I);

$R^7$ has the meaning given above in relation to formula (A-I);

$R^9$ is on each occurrence, identically or differently, H, D, F, CN, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^7$, where one or more non-adjacent $CH_2$ groups may be replaced by $R^7C=CR^7$, $C\equiv C$, O or S and where one or more H atoms may be replaced by F.

According to a further preferred embodiment of the present invention, functional compounds of the general formula (V-IVa) and/or formula (V-IVb):

formula (V-IVa)

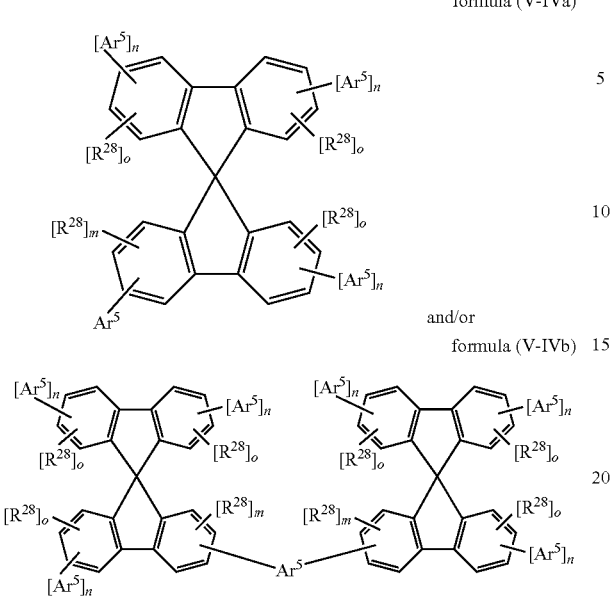

and/or
formula (V-IVb)

are excluded from the present invention, where the following applies to the symbols and indices used:

Ar⁵ is a group of the following formula (V-IVc):

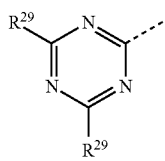

formula (V-IVc)

where the dashed bond indicates the bond to the spirobifluorene;

Ar⁶ is a group of the following formula (V-IVd):

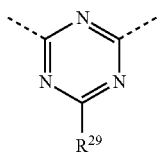

formula (V-IVd)

where the dashed bonds indicate the bonds to the spirobifluorene;

$R^{28}$, $R^{29}$ are on each occurrence, identically or differently, H, D, F, Cl, Br, I, CHO, $N(R^{30})_2$, $N(Ar^7)_2$, $B(Ar^7)_2$, C(=O)$Ar^7$, P(=O)$(Ar^7)_2$, S(=O)$Ar^7$, S(=O)$_2Ar^7$, $CR^{30}$=$CR^{30}Ar^7$, CN, $NO_2$, $Si(R^{30})_3$, $B(OR^{30})_2$, $B(R^{30})_2$, $B(N(R^{30})_2)_2$, $OSO_2R^{30}$, a straight-chain alkyl, alkenyl, alkynyl, alkoxy or thioalkoxy group having 1 or 2 to 40 C atoms respectively or a branched or cyclic alkyl, alkenyl, alkynyl, alkoxy or thioalkoxy group having 3 to 40 C atoms, each of which may be substituted by one or more radicals $R^{30}$, where one or more non-adjacent $CH_2$ groups may be replaced by $R^{30}C$=$CR^{30}$, C≡C, $Si(R^{30})_2$, $Ge(R^{30})_2$, $Sn(R^{30})_2$, C=O, C=S, C=Se, O=$NR^{30}$, P(=O)$(R^{30})$, SO, $SO_2$, $NR^{30}$, O, S or $CONR^{30}$ and where one or more H atoms may be replaced by D, F, Cl, Br, I, CN or $NO_2$, a crosslinkable group or an aromatic or heteroaromatic ring system having 5 to 60 aromatic ring atoms, which may in each case be substituted by one or more radicals $R^{30}$, or an aryloxy or heteroaryloxy group having 5 to 60 aromatic ring atoms, which may be substituted by one or more radicals $R^{30}$, or a combination of these systems; two or more adjacent substituents $R^{28}$ here may also form a mono- or polycyclic, aliphatic or aromatic ring system with one another;

$Ar^7$ is on each occurrence, identically or differently, an aromatic or heteroaromatic ring system having 5 to 30 aromatic ring atoms, which may be substituted by one or more radicals $R^{30}$; two radicals $Ar^7$ here which are bonded to the same nitrogen, phosphorus or boron atom may also be linked to one another by a single bond or a bridge selected from)$B(R^{30})$, $C(R^{30})_2$, $Si(R^{30})_2$, C=O, C=$NR^{30}$, C=$C(R^{30})_2$, O, S, S=O, $SO_2$, $N(R^{30})$, $P(R^{30})$ and P(=O)$R^{30}$;

$R^{30}$ is on each occurrence, identically or differently, H, D or an aliphatic, aromatic and/or heteroaromatic hydrocarbon radical having 1 to 20 C atoms, in which, in addition, H atoms may be replaced by D or F; two or more adjacent substituents $R^{30}$ here may also form a mono- or polycyclic, aliphatic or aromatic ring system with one another;

n is 0 or 1;

m is 0, 1, 2 or 3;

o is 0, 1, 2, 3 or 4 if n=0 in the same ring and is 0, 1, 2 or 3 if n=1 in the same ring.

The particularly preferred functional compounds include compounds of the formulae (V-Ia), (V-Ib), (V-Ic) and (V-Id)

formula V-Ia

formula V-Ib

formula V-Ic

formula V-Id where the following applies to the symbols used:

DCy is, identically or differently on each occurrence, a cyclic group which contains at least one donor atom, preferably nitrogen, carbon in the form of a carbene, or phosphorus, via which the cyclic group is bonded to the metal, and which may in turn carry one or more substituents $R^{10}$; the groups DCy and CCy are connected to one another via a covalent bond;

CCy is, identically or differently on each occurrence, a cyclic group which contains a carbon atom via which the cyclic group is bonded to the metal and which may in turn carry one or more substituents $R^{10}$;

A is, identically or differently on each occurrence, a monoanionic, bidentate-chelating ligand, preferably a diketonate ligand;

$R^{10}$ is on each occurrence, identically or differently, H, D, F, Cl, Br, I, CHO, C(=O)$Ar^3$, P(=O)$(Ar^3)_2$, S(=O)$Ar^3$, S(=O)$_2$Ar$^3$, CR$^{11}$=CR$^{11}$Ar$^3$, CN, NO$_2$, Si(R$^{11}$)$_3$, B(OR$^{11}$)$_2$, B(R$^{11}$)$_2$, B(N(R$^{11}$)$_2$)$_2$, OSO$_2$R$^{11}$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^{11}$, where one or more non-adjacent CH$_2$ groups may be replaced by R$^{11}$C=CR$^{11}$, C≡C, Si(R$^{11}$)$_2$, Ge(R$^{11}$)$_2$, Sn(R$^{11}$)$_2$, C=O, C=S, C=Se, C=NR$^{11}$, P(=O)(R$^{11}$), SO, SO$_2$, NR$^{11}$, O, S or CONR$^{11}$ and where one or more H atoms may be replaced by F, Cl, Br, I, ON or NO$_2$, or an aromatic or heteroaromatic ring system having 5 to 60 aromatic ring atoms, which may in each case be substituted by one or more radicals R$^{11}$, or an aryloxy or heteroaryloxy group having 5 to 60 aromatic ring atoms, which may be substituted by one or more radicals R$^{11}$, or a combination of these systems; two or more adjacent substituents R$^{10}$ here may also form a mono- or polycyclic, aliphatic or aromatic ring system with one another;

Ar$^3$ is on each occurrence, identically or differently, an aromatic or heteroaromatic ring system having 5 to 40 aromatic ring atoms, which may be substituted by one or more radicals R$^{11}$;

R$^{11}$ is on each occurrence, identically or differently, H, D, CN or an aliphatic, aromatic and/or heteroaromatic hydrocarbon radical having 1 to 20 C atoms, in which, in addition, H atoms may be replaced by F; two or more adjacent substituents R$^{11}$ here may also form a mono- or polycyclic, aliphatic or aromatic ring system with one another, where at least one of the said radicals DCy, CCy and/or A contains at least one group of the formulae (L-I) and/or (L-II).

Due to formation of ring systems between a plurality of radicals R$^{10}$, a bridge may also be present between the groups DCy and CCy. Furthermore, due to formation of ring systems between a plurality of radicals R$^{10}$, a bridge may also be present between two or three ligands CCy-DCy or between one or two ligands CCy-DCy and the ligand A, giving a polydentate or polypodal ligand system respectively.

According to a further, particular embodiment of the present invention, soluble functional compounds, in particular polyacenes of the formula (V-II),

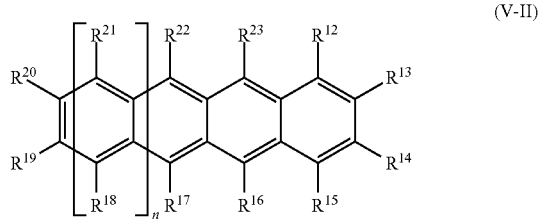
(V-II)

are provided, in which
the radicals R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are each independently hydrogen, a straight-chain alkyl, alkoxy or thioalkoxy group having 1 to 40 C atoms or a branched or cyclic alkyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a cyano group (—ON), a carbamoyl group (—C(=O)NH$_2$), a haloformyl group (—C(=O)—X, in which X represents a halogen atom), a formyl group (—C(=O)—H), an isocyano group, an isocyanate group, a thiocyanate group or a thioisocyanate group, an amino group, a hydroxyl group, a nitro group, a CF$_3$ group, Cl, Br, F, a crosslinkable group or a substituted or unsubstituted, aromatic or heteroaromatic ring system having 5 to 60 ring atoms, or an aryloxy or heteroaryloxy group having 5 to 60 ring atoms, or a combination of these systems, where one or more of the groups R$^{12}$, R$^{13}$, R$^{14}$, R$^{15}$, R$^{16}$, R$^{17}$, R$^{18}$, R$^{19}$, R$^{20}$, R$^{21}$, R$^{22}$ and/or R$^{23}$ may form a mono- or polycyclic, aliphatic or aromatic ring system with one another and/or with the ring to which the respective group is bonded; and in which each pair R$^{12}$ and R$^{13}$, R$^{13}$ and R$^{14}$, R$^{14}$ and R$^{15}$, R$^{18}$ and R$^{19}$, R$^{19}$ and R$^{20}$, R$^{20}$ and R$^{21}$ independently may optionally form a saturated or unsaturated C$_4$-C$_{40}$ ring, which may be interrupted by one or more oxygen and/or sulfur atoms or a group of the formula —N(R$^a$)—, in which R$^a$ represents a hydrogen atom or an optionally substituted hydrocarbon group, where the ring may optionally be substituted; and in which one or more carbon atoms of the polyacene skeleton may optionally be substituted by one or more heteroatoms selected from N, P, As, O, S, Se and Te; and where one or more of the substituents R$^{12}$ to R$^{23}$ which are arranged at adjacent ring positions of the polyacene may together form a further saturated or unsaturated ring, which may be interrupted by one or more oxygen and/or sulfur atoms or a group of the formula —N(R$^a$)—, in which R$^a$ represents a hydrogen atom or an optionally substituted hydrocarbon group, or an aromatic ring system which is bonded to the polyacene; and in which n is 0, 1, 2, 3 or 4, preferably 0, 1 or 2, particularly preferably 0 or 2;

where at least one of the radicals R$^{12}$, R$^{13}$, R$^{14}$, R$^{15}$, R$^{16}$, R$^{17}$, R$^{18}$, R$^{19}$, R$^{20}$, R$^{21}$, R$^{22}$ and/or R$^{23}$ includes at least one group of the formula (L-I) or (L-II).

If n in formula (V-II) is equal to 2, this compound is a pentacene compound. For n=0, the compound may be a "pseudopentacene compound".

According to a further embodiment, the present invention provides functional compounds of the general formulae (V-IIIa) and/or (V-IIIb)

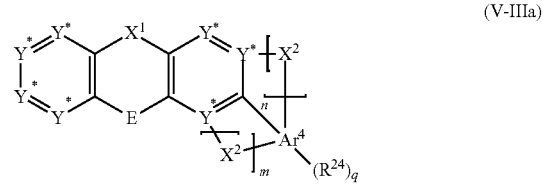
(V-IIIa)

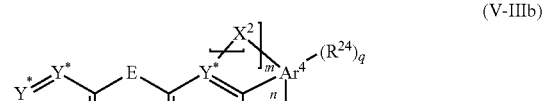
(V-IIIb)

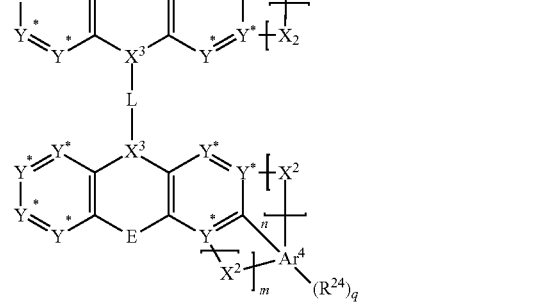

where the following applies to the symbols and indices:
Y* is C if a group X$^2$ is bonded to the group Y or is on each occurrence, identically or differently, CR or N if no group X$^2$ is bonded to the group Y;

E is on each occurrence, identically or differently, a covalent single bond or a divalent bridge selected from $N(R^{25})$, $B(R^{25})$, $C(R^{25})_2$, $O$, $Si(R^{25})_2$, $C=NR^{25}$, $C=C(R^{25})_2$, $S$, $S=O$, $SO_2$, $P(R^{25})$ and $P(=O)R^1$;

$X^1$ is on each occurrence, identically or differently, a divalent bridge selected from $N(R^{25})$, $B(R^{25})$, $O$, $C(R^{25})_2$, $Si(R^{25})_2$, $C=NR^{25}$, $C=C(R^{25})_2$, $S$, $S=O$, $SO_2$, $P(R^{25})$ and $P(=O)R^{25}$;

$X^2$ is on each occurrence, identically or differently, a divalent bridge selected from $N(R^{25})$, $B(R^{25})$, $C(R^{25})_2$, $Si(R^{25})_2$, $C=O$, $C=NR^{25}$, $C=C(R^{25})_2$, $S$, $S=O$, $SO_2$, $CR^{25}=CR^{25}$, $P(R^{25})$ and $P(=O)R^{25}$;

$X^3$ is on each occurrence, identically or differently, a divalent bridge selected from $N$, $B$, $C(R^1)$, $Si(R^1)$, $P$ and $P(=O)$;

L is a divalent, aromatic or heteroaromatic ring system having 5 to 40 aromatic ring atoms, which may be substituted by one or more radicals $R^1$;

n, m are 0 or 1, with the proviso that n+m=1 or 2;

q is 1, 2, 3, 4, 5 or 6;

$R^{24}$ is on each occurrence, identically or differently, H, D, F, Cl, Br, I, $N(Ar)_2$, $C(=O)Ar$, $P(=O)Ar_2$, $S(=O)Ar$, $S(=O)_2Ar$, $CR^{26}=CR^{26}Ar$, CN, $NO_2$, $Si(R^{26})_3$, $B(OR^{26})_2$, $OSO_2R^{26}$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^{26}$, where one or more non-adjacent $CH_2$ groups may be replaced by $R^{26}C=CR^{26}$, $C\equiv C$, $Si(R^{26})_2$, $Ge(R^{26})_2$, $Sn(R^{26})_2$, $C=O$, $C=S$, $C=Se$, $C=NR^{26}$, $P(=O)(R^{26})$, SO, $SO_2$, $NR^{26}$, O, S or $CONR^{26}$ and where one or more H atoms may be replaced by D, F, Cl, Br, I, ON or $NO_2$, a crosslinkable group or an aromatic or heteroaromatic group having 5 to 40 ring atoms, each of which may be substituted by one or more radicals $R^{26}$, or an aromatic or heteroaromatic ring system having 5 to 40 aromatic ring atoms, which may in each case be substituted by one or more radicals $R^{26}$, or an aryloxy or heteroaryloxy group having 5 to 40 aromatic ring atoms, which may be substituted by one or more radicals $R^{26}$, or a combination of these systems; two or more substituents $R^{24}$ here may also form a mono- or polycyclic, aliphatic, aromatic or heteroaromatic ring system with one another, together with the atoms to which they are bonded or, if they are bonded to Ar, with Ar;

$R^{25}$ is on each occurrence, identically or differently, H, D, F, Cl, Br, I, CN, $NO_2$, $CF_3$, $B(OR^{26})_2$, $Si(R^{26})_3$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^{26}$, where one or more non-adjacent $CH_2$ groups may be replaced by $—R^{26}C=CR^{26}—$, $—C\equiv C—$, $Si(R^{26})_2$, $Ge(R^{26})_2$, $Sn(R^{26})_2$, $C=O$, $C=S$, $C=Se$, $C=NR^{26}$, $—O—$, $—S—$, $—COO—$ or $—CONR^{26}—$ and where one or more H atoms may be replaced by D, F, Cl, Br, I, ON or $NO_2$, or arylamines, or substituted or unsubstituted carbazoles, each of which may be substituted by one or more radicals $R^{26}$, or an aryl or heteroaryl group having 5 to 40 ring atoms, which may be substituted by one or more aromatic or heteroaromatic or non-aromatic radicals $R^{27}$, or an aromatic or heteroaromatic ring system having 5 to 40 aromatic ring atoms, which may be substituted by one or more non-aromatic radicals $R^{26}$, or an aryloxy or heteroaryloxy group having 5 to 40 aromatic ring atoms, which may be substituted by one or more non-aromatic radicals $R^{27}$, or a combination of these systems; two or more substituents $R^{25}$ here, together with the atoms to which they are bonded, may also form a mono- or polycyclic, aliphatic, aromatic or heteroaromatic ring system with one another;

$R^{26}$ is on each occurrence, identically or differently, H, D or an aliphatic or aromatic hydrocarbon radical having 1 to 20 C atoms;

$Ar^4$ is on each occurrence, identically or differently, an aromatic or heteroaromatic ring system having 5 to 40 ring atoms, which may be substituted by one or more radicals $R^{25}$;

where at least one of the above-mentioned radicals includes a group of the formulae (L-I) and/or (L-II).

In addition, preference is given to soluble functional compounds of the formula (V-V),

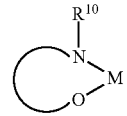

formula (V-V)

where $R^{10}$ has the same meaning as described above for the formulae (V-Ia), (V-Ib), (V-Ic) and (V-Id), the curved line represents two or three atoms and bonds which are necessary to make up a 5- or 6-membered ring with M, where these atoms may also be substituted by one or more radicals $R^{10}$, where at least one of the above-mentioned radicals includes a group of the formulae (L-I) and/or (L-II), and M represents an alkali metal selected from lithium, sodium, potassium, rubidium and caesium.

It is possible here for the complex of the formula (V-V) to be in monomeric form, as depicted above, or for it to be in the form of aggregates, for example comprising two alkali-metal ions and two ligands, four alkali-metal ions and four ligands, six alkali-metal ions and six ligands, or in the form of other aggregates.

Preferred compounds of the formula (V-V) are the compounds of the following formulae (V-V1) and (V-V2)

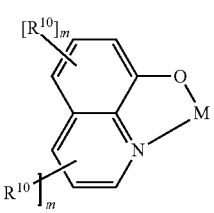

formula (V-V1)

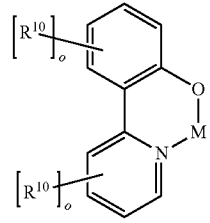

formula (V-V2)

where the symbols used have the same meaning as described above for the formulae (V-Ia), (V-Ib), (V-Ic) and (V-Id) and above for the formula (V-V), and m stands, identically or differently on each occurrence, for 0, 1, 2 or 3 and o stands, identically or differently on each occurrence, for 0, 1, 2, 3 or 4.

Further preferred organic alkali-metal compounds are the compounds of the following formula (V-V3):

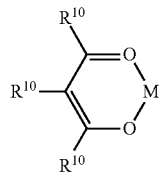

formula (V-V3)

where the symbols used have the same meaning as described above for the formulae (V-Ia), (V-Ib), (V-Ic) and (V-Id) and above for the formula (V-V), where at least one of the above-mentioned radicals includes a group of the formulae (L-I) and/or (L-II).

The alkali metal is preferably selected from lithium, sodium and potassium, particularly preferably from lithium and sodium, and is very particularly preferably lithium.

Particular preference is given to a compound of the formula (V-V1), in particular where M=lithium. Furthermore, the indices m are very particularly preferably =0. The compound is thus very particularly preferably unsubstituted lithium quinolinate.

The functional compounds of the formula (I) which are particularly preferably to be employed include, inter alia,

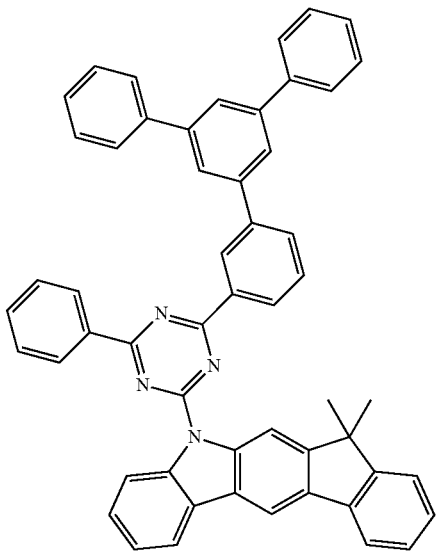

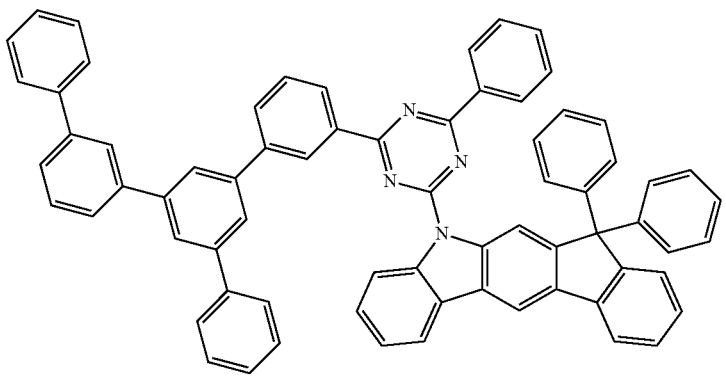

-continued
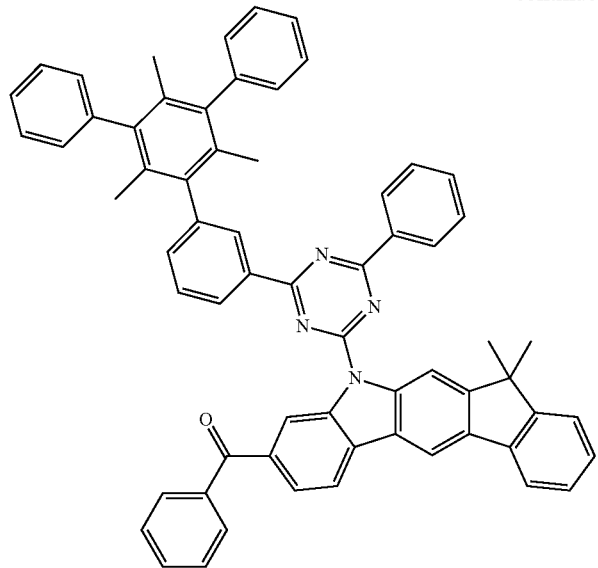
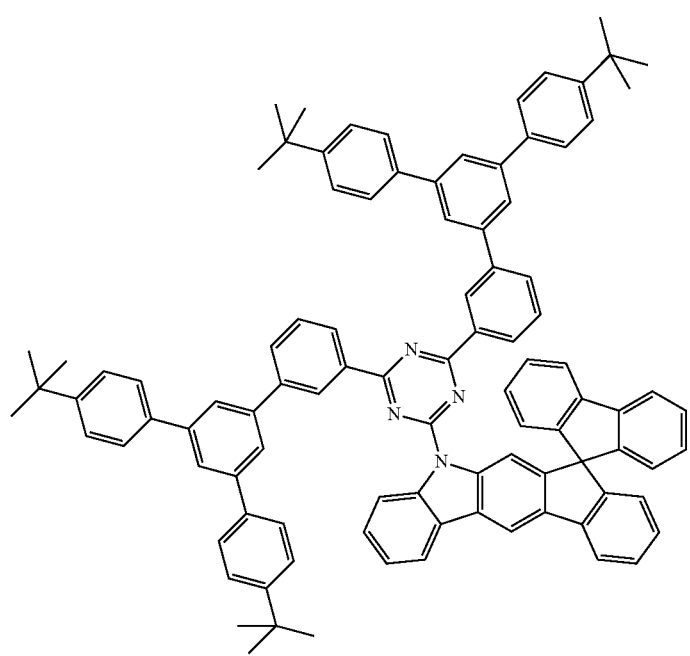

-continued
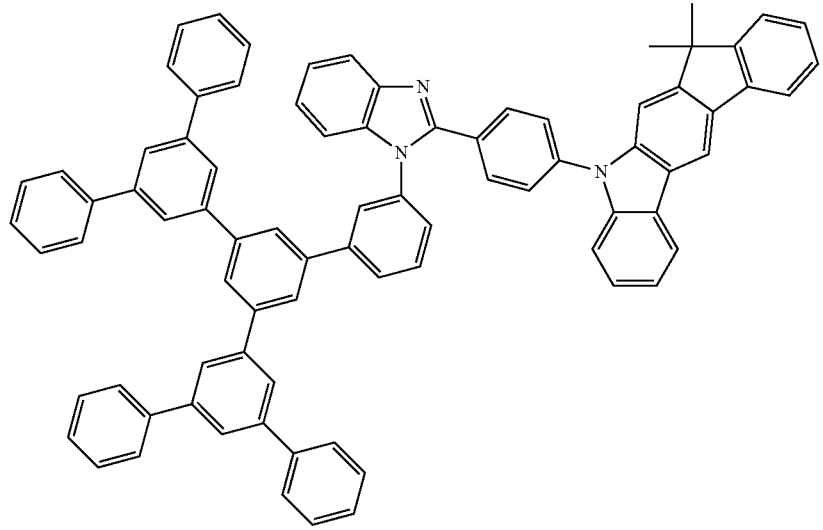
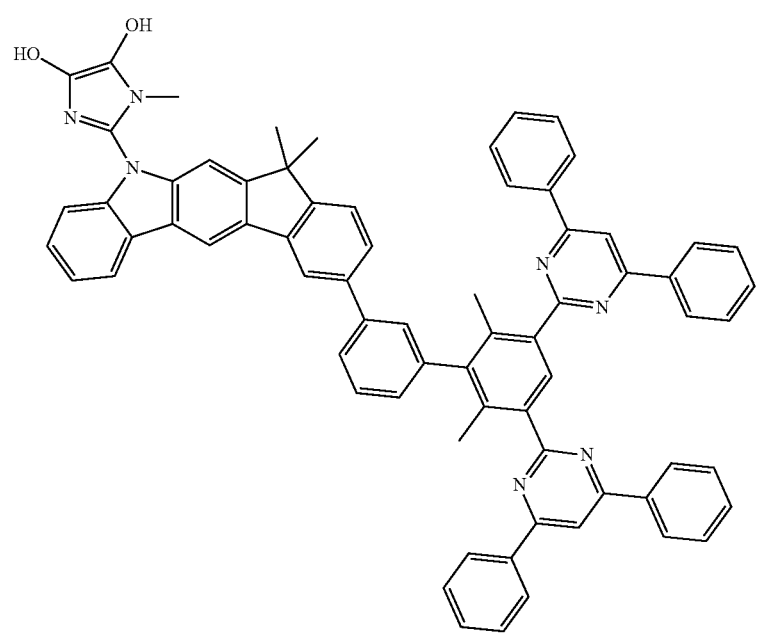

-continued
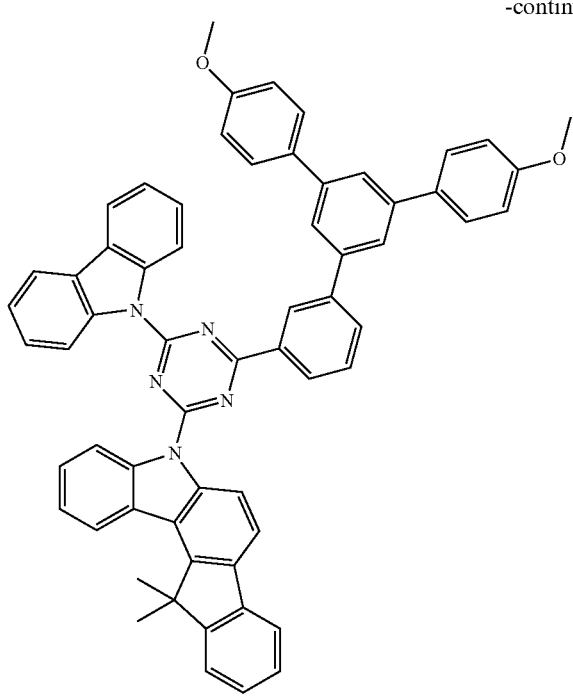
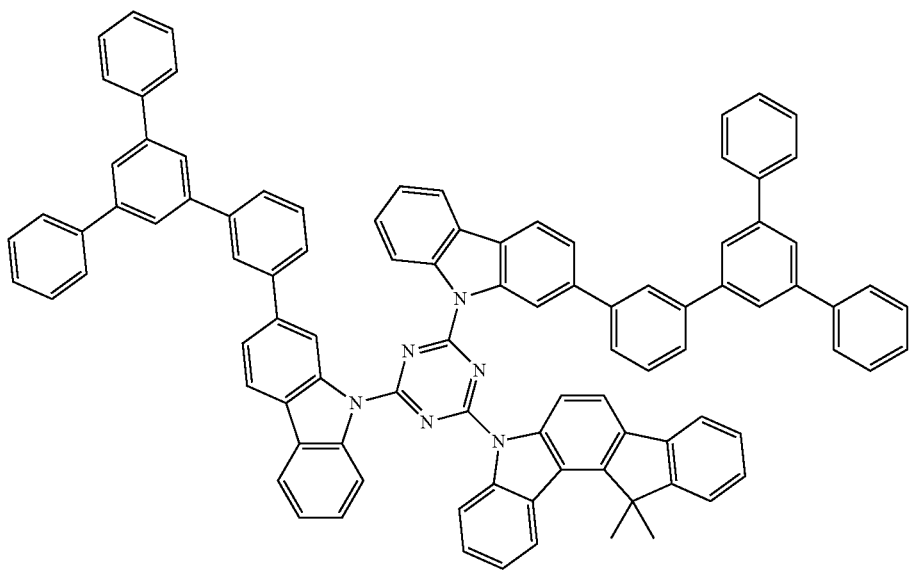

-continued
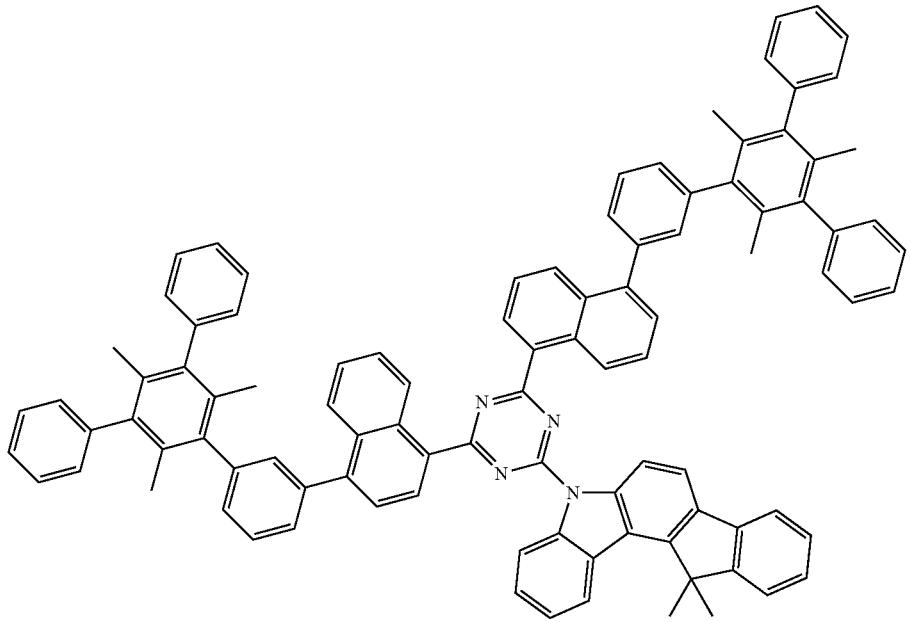
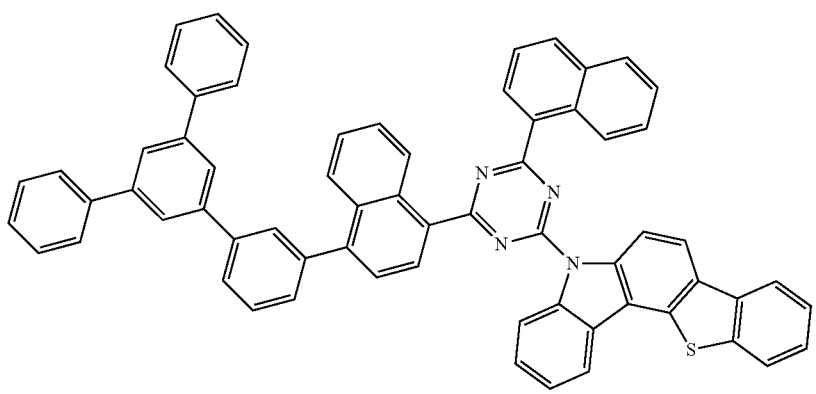
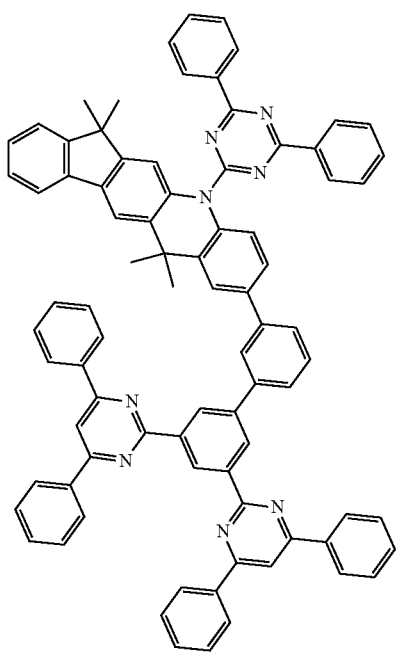

-continued
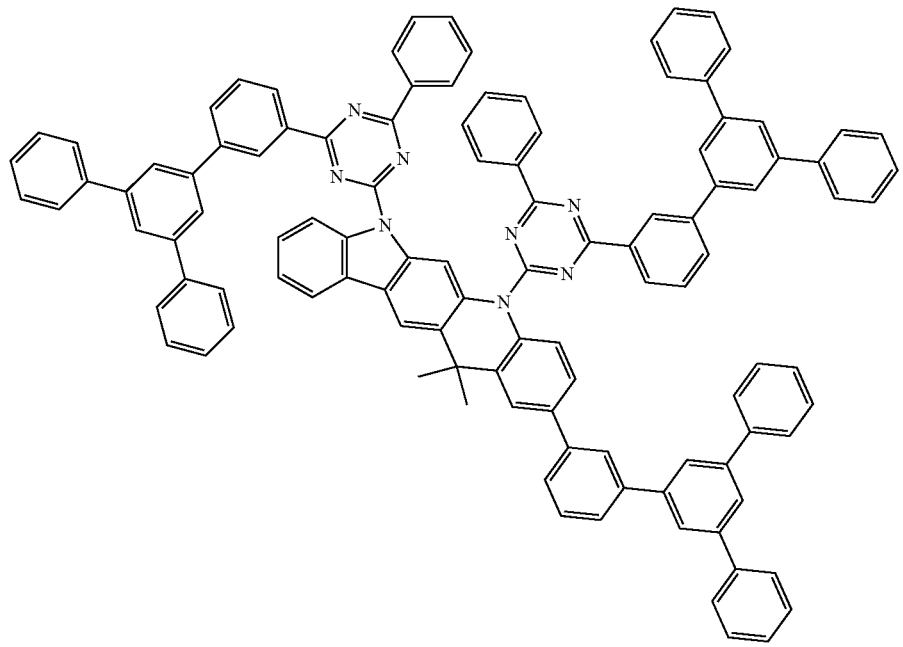
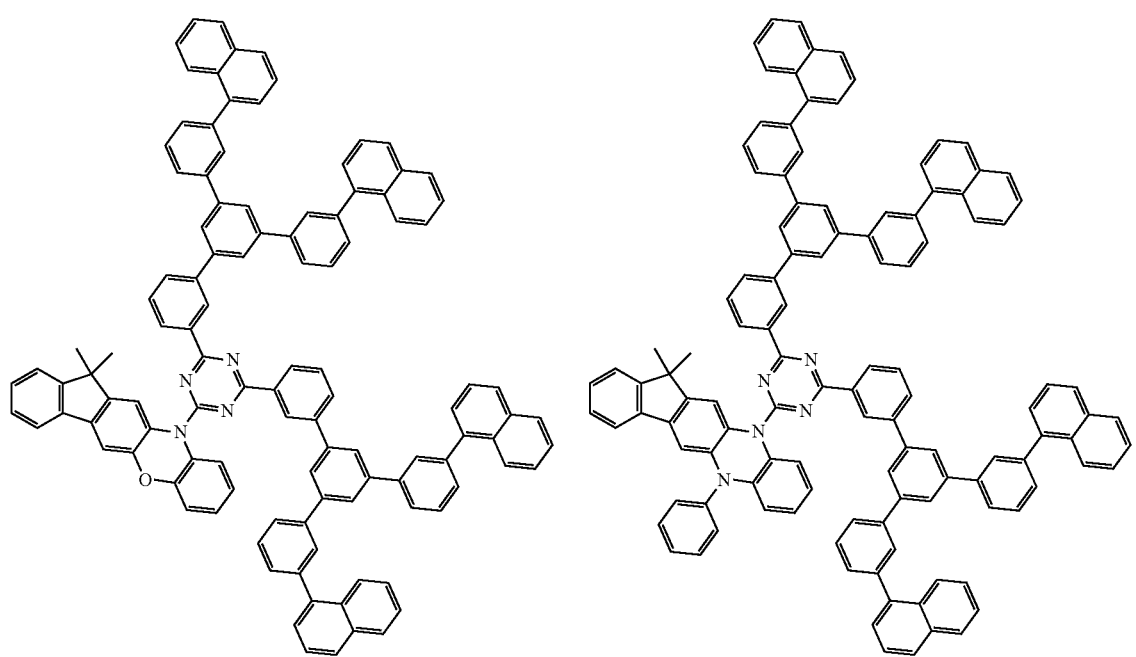

-continued
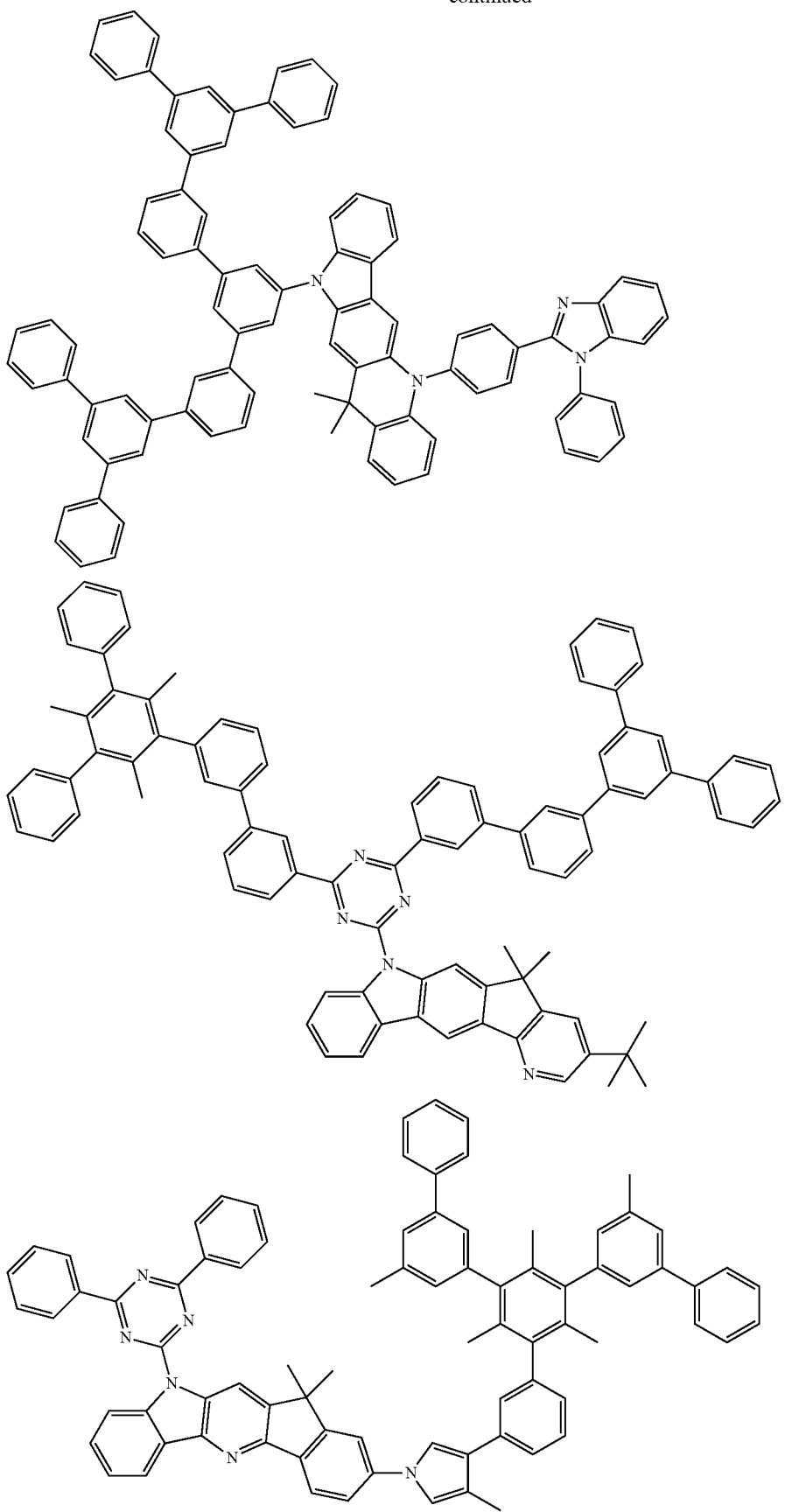

-continued
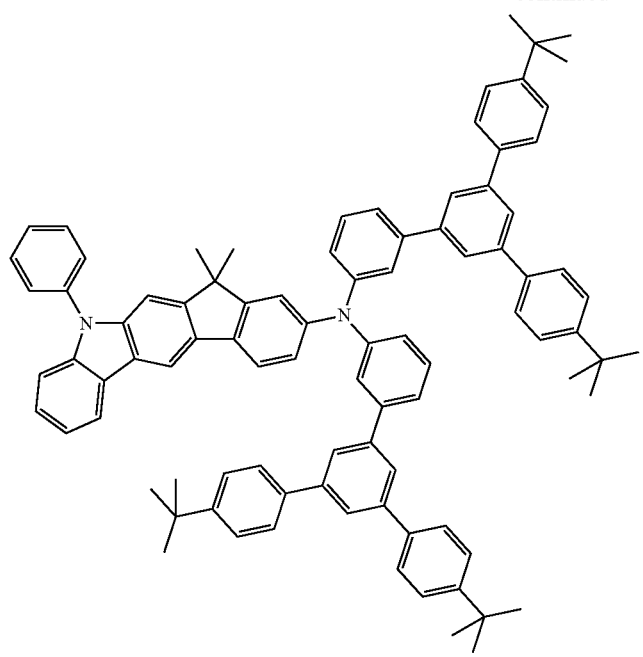
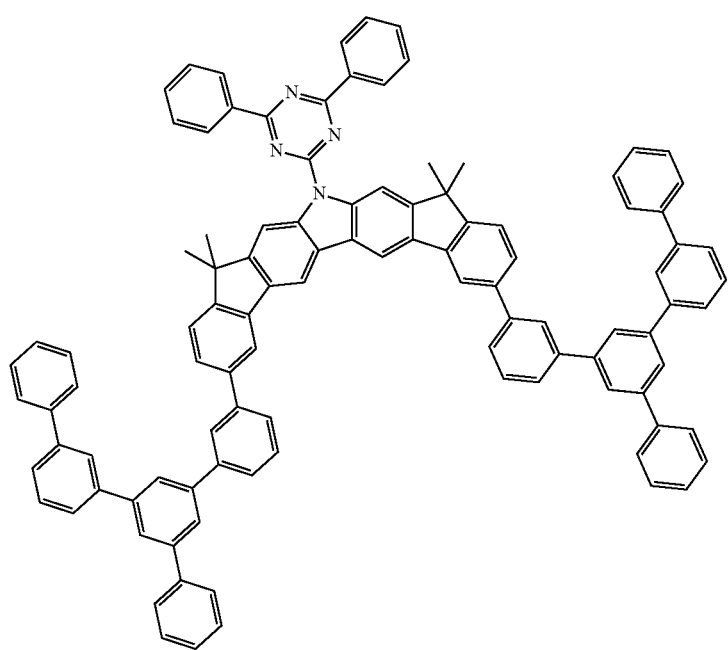

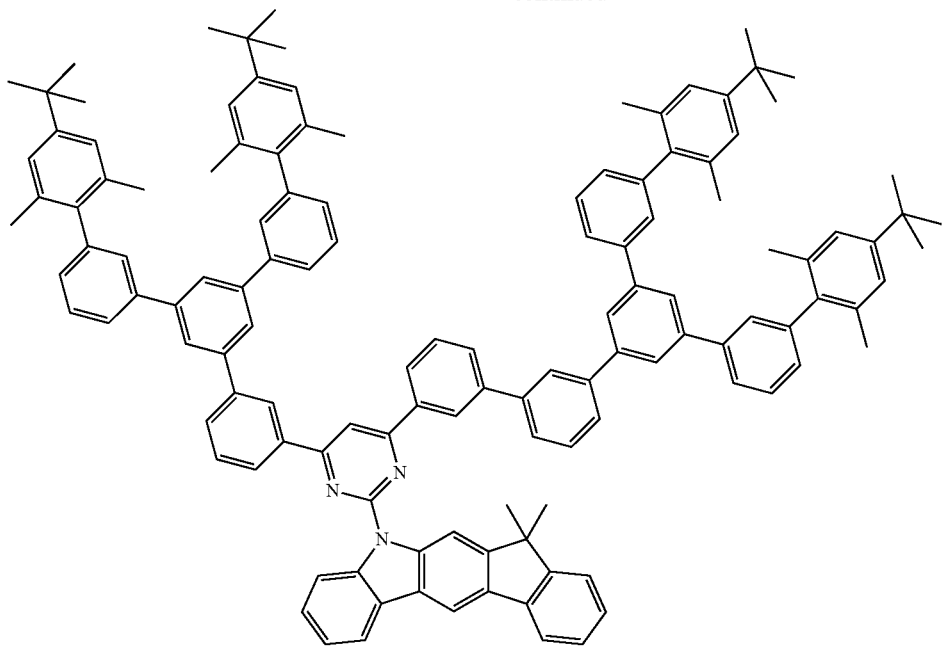
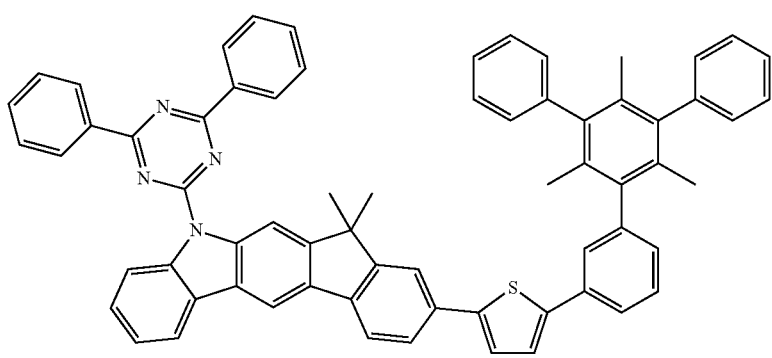
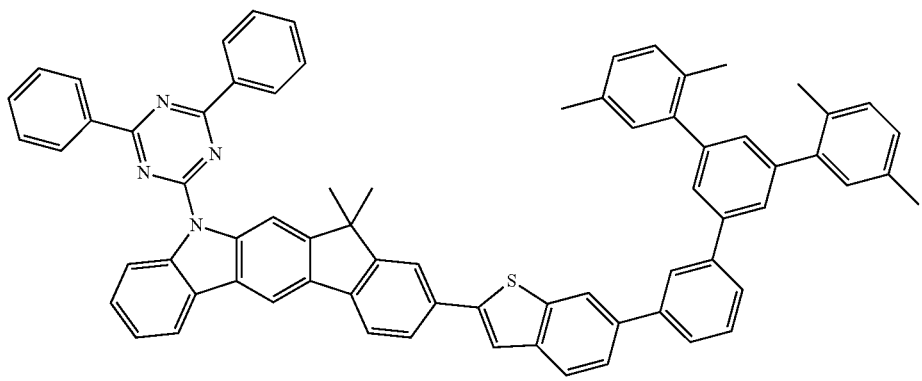

-continued
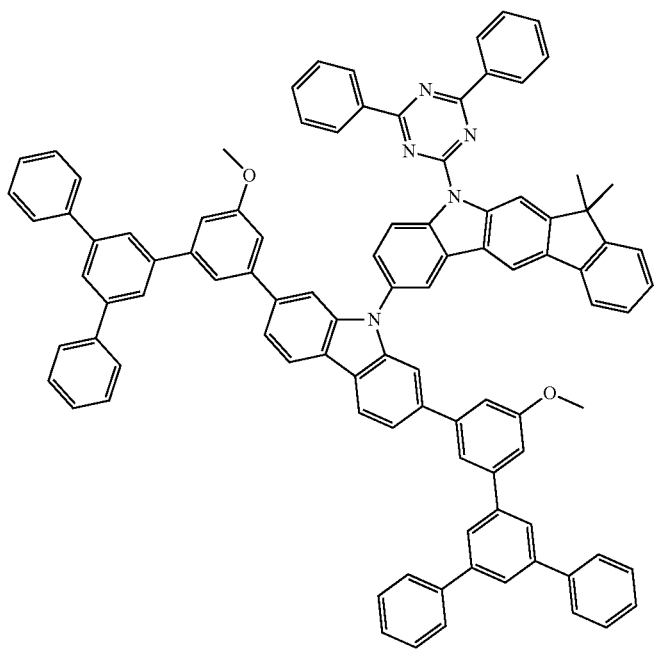
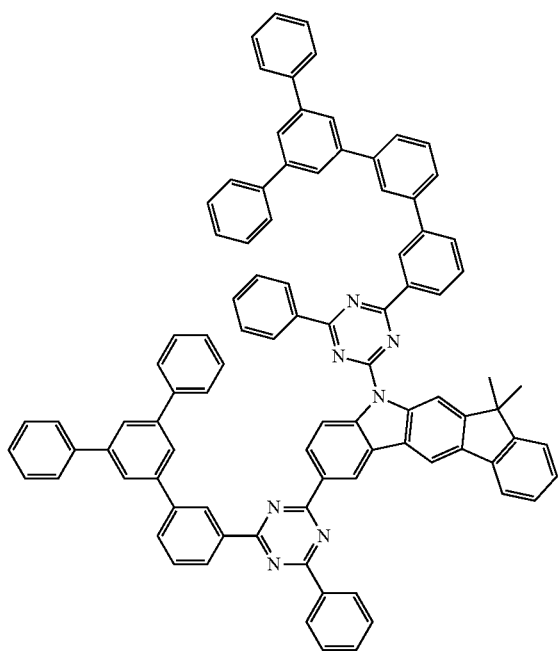

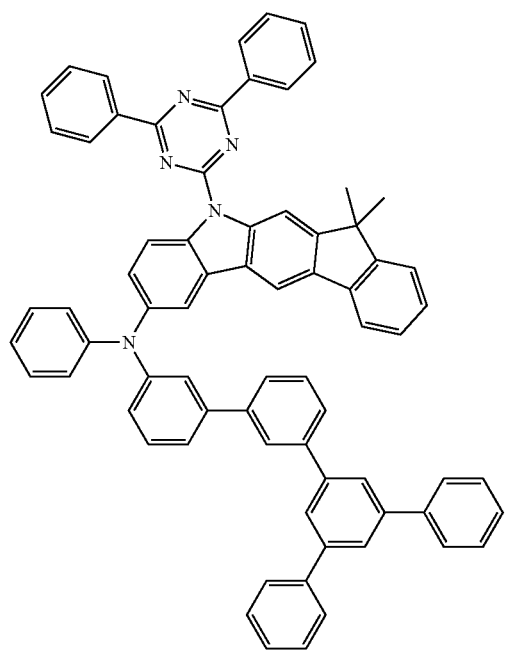
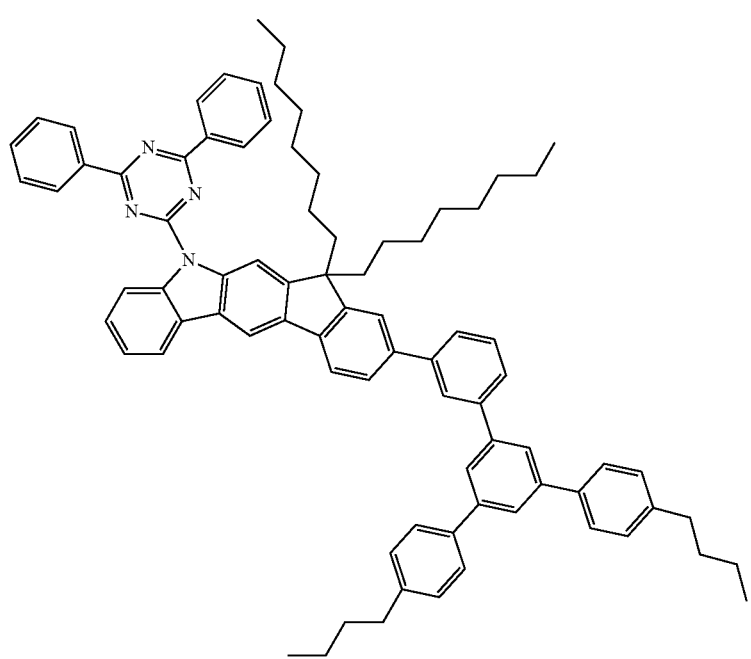

-continued
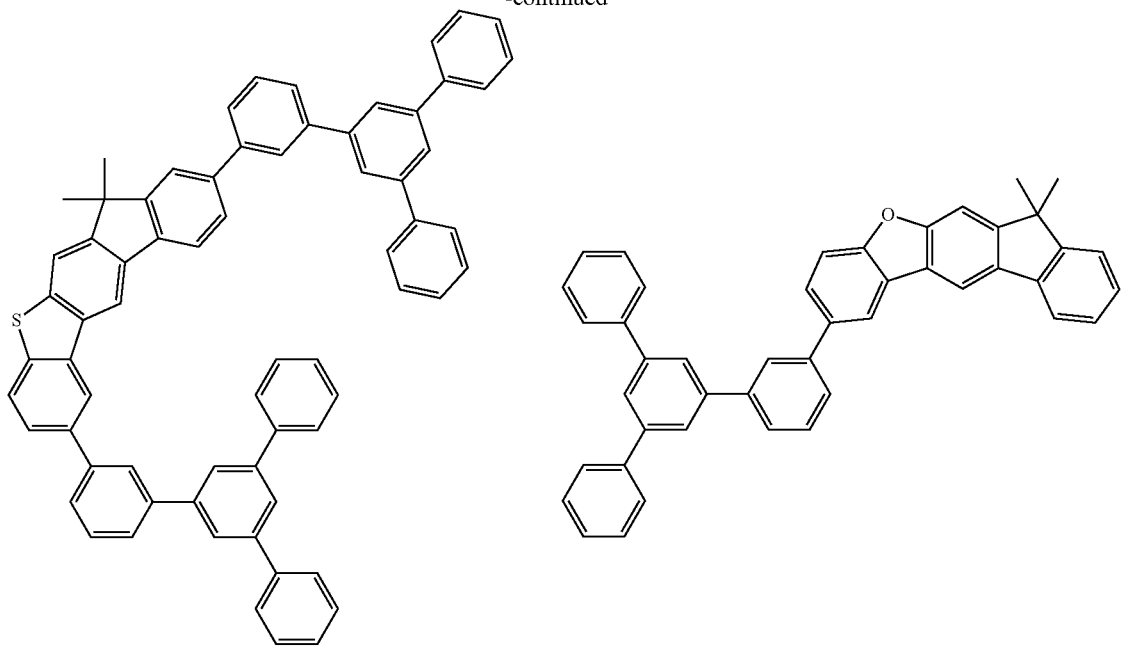
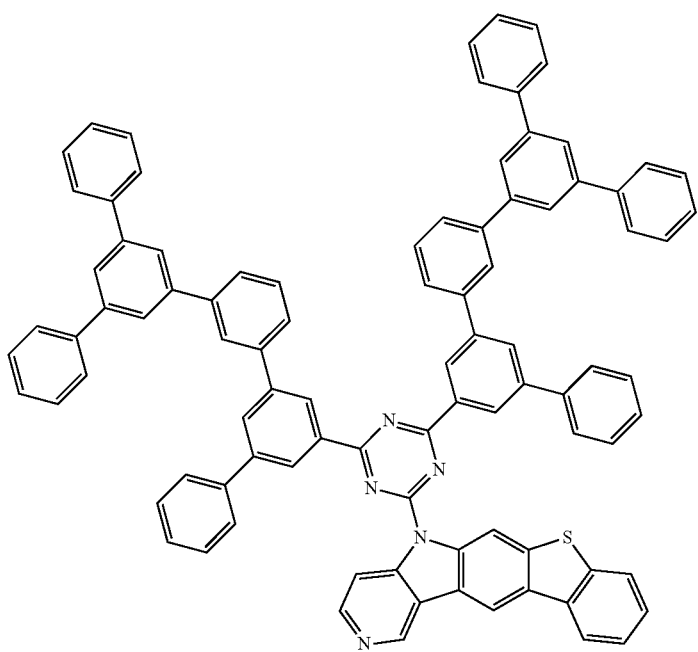

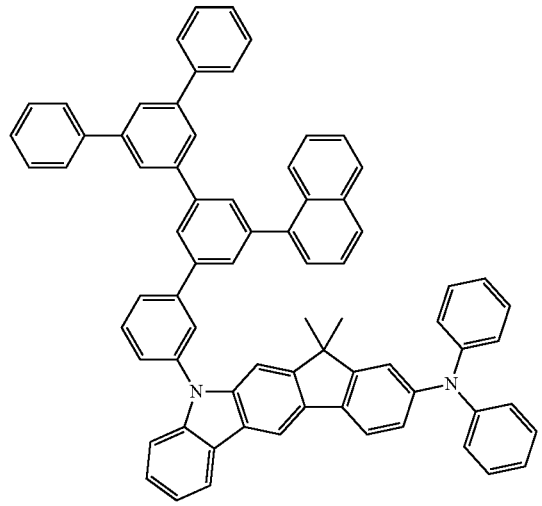
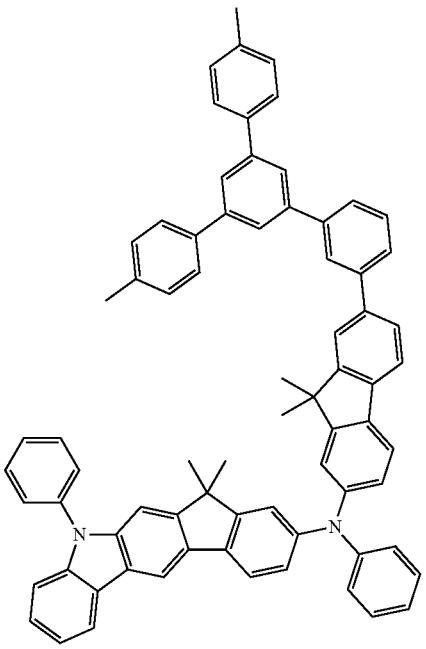
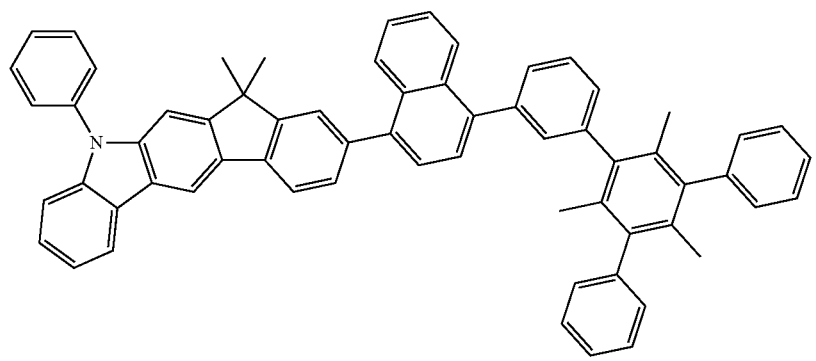
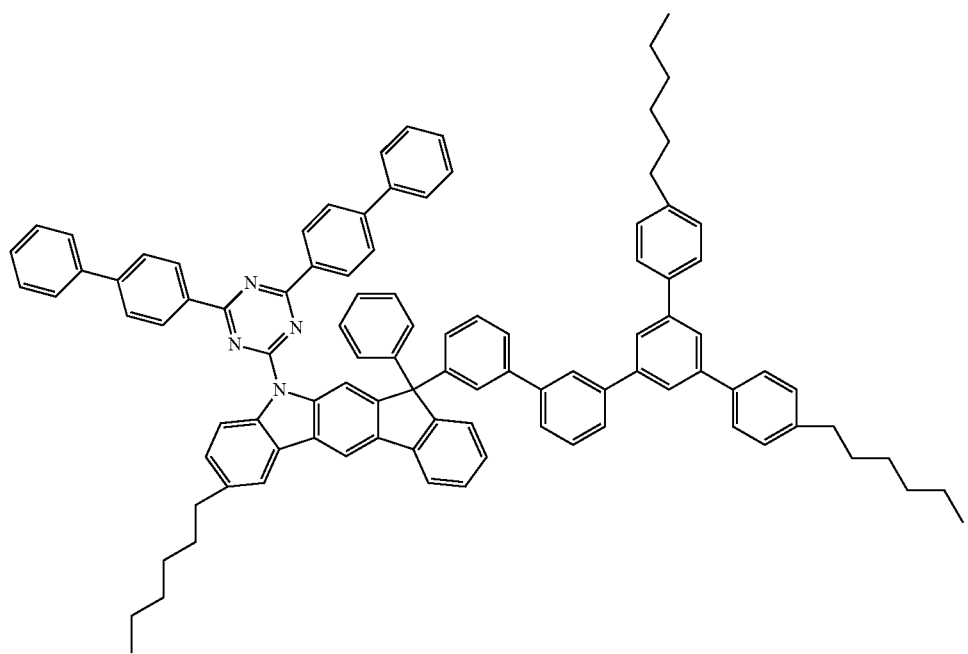

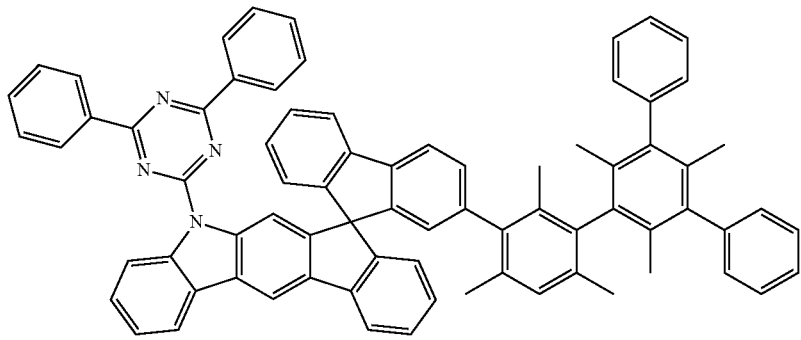
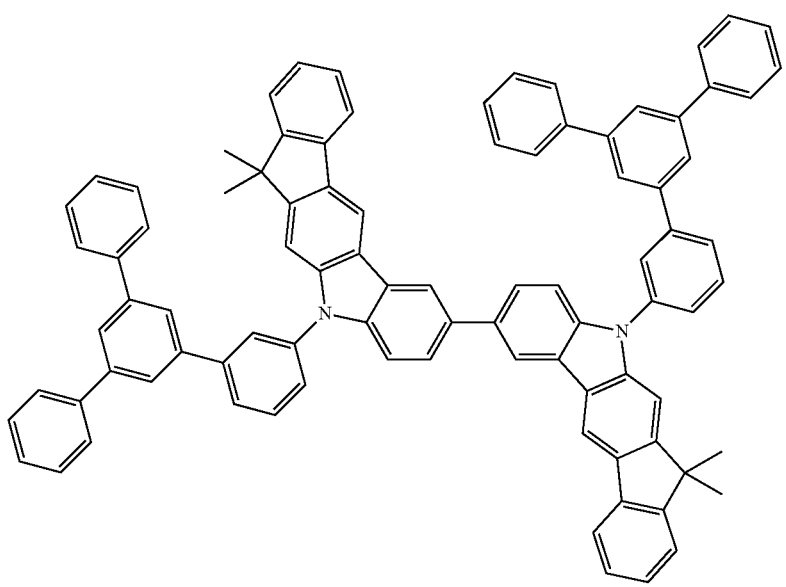
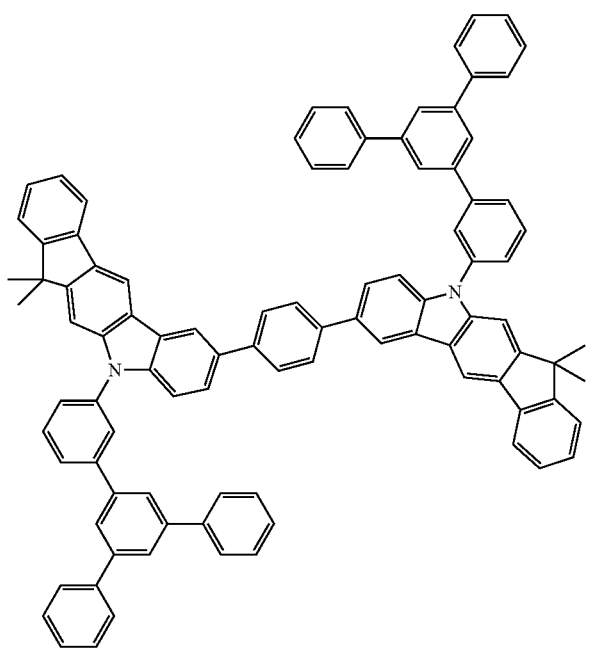

-continued
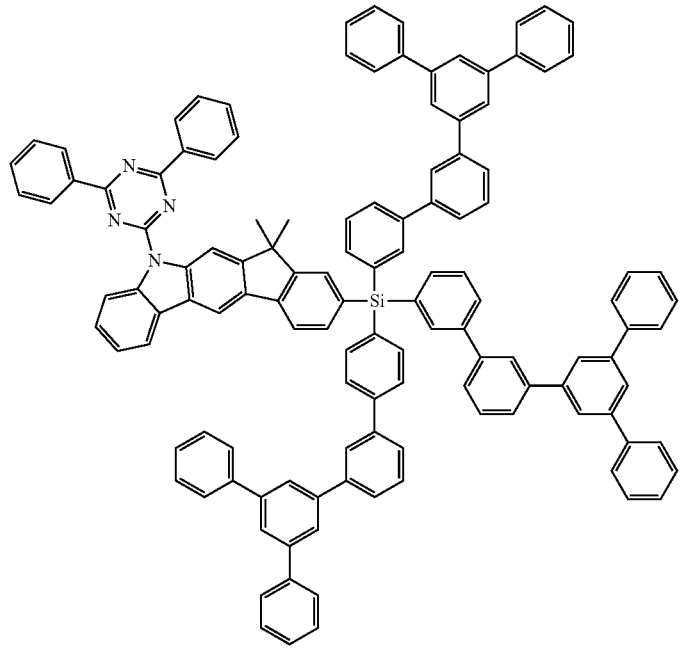
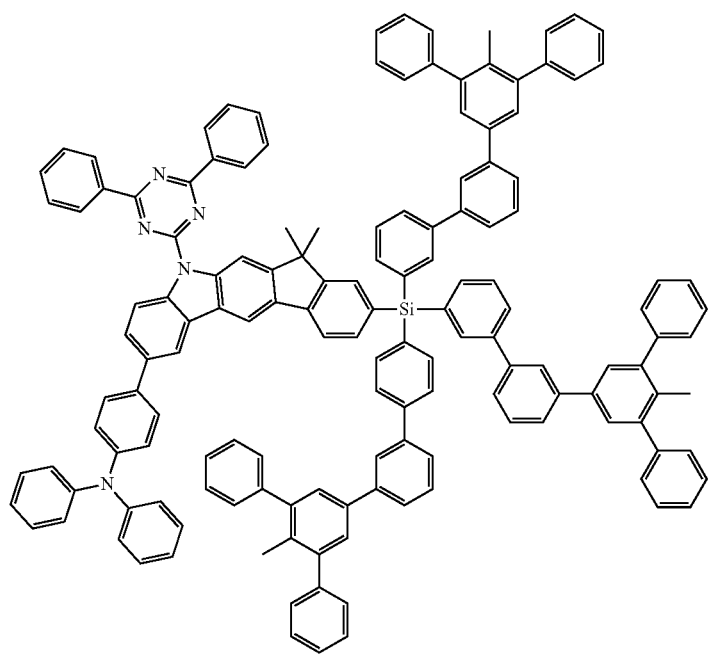

-continued
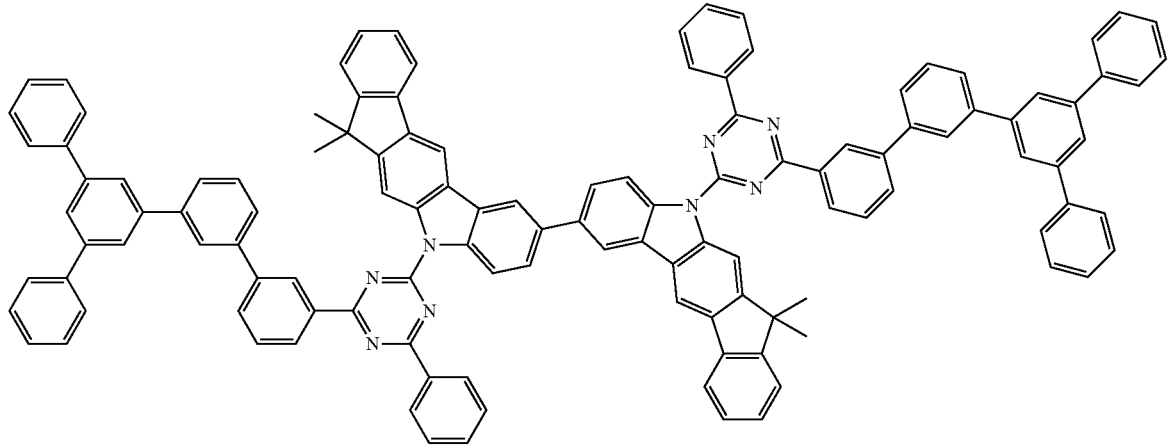
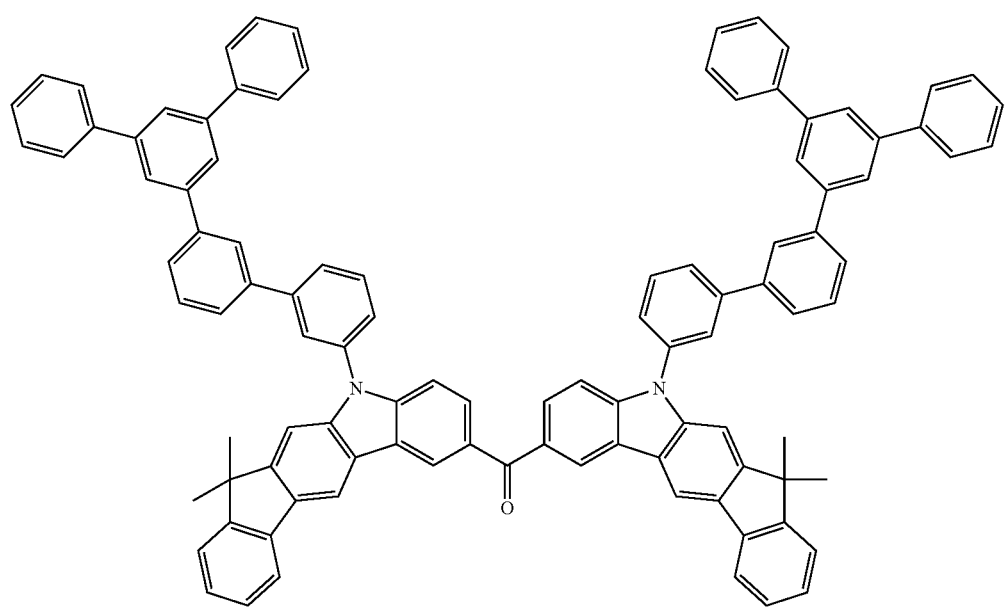
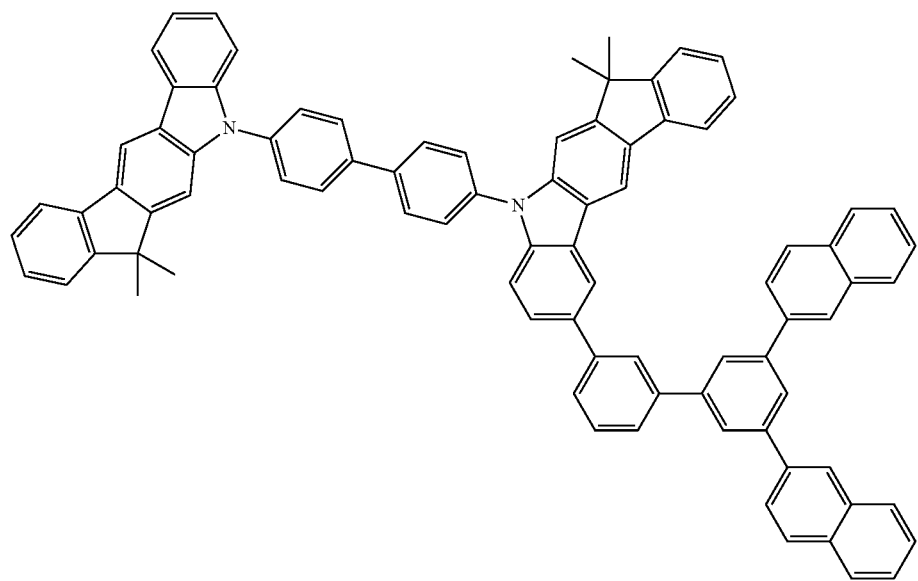

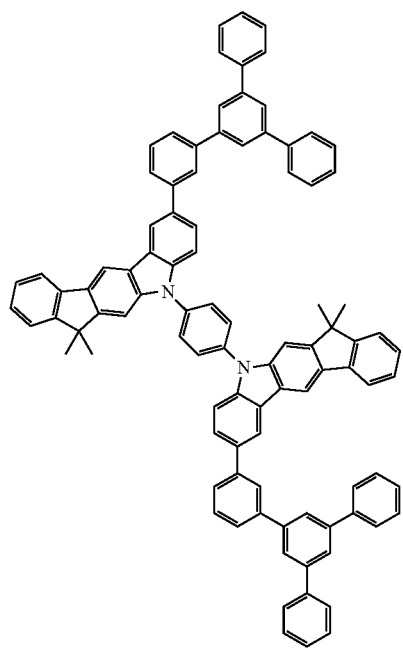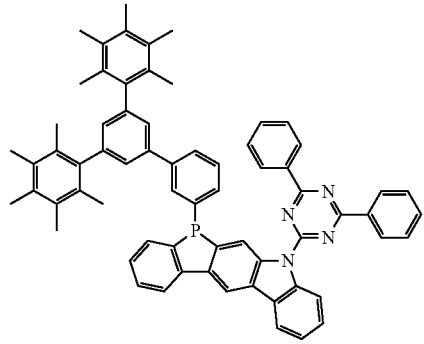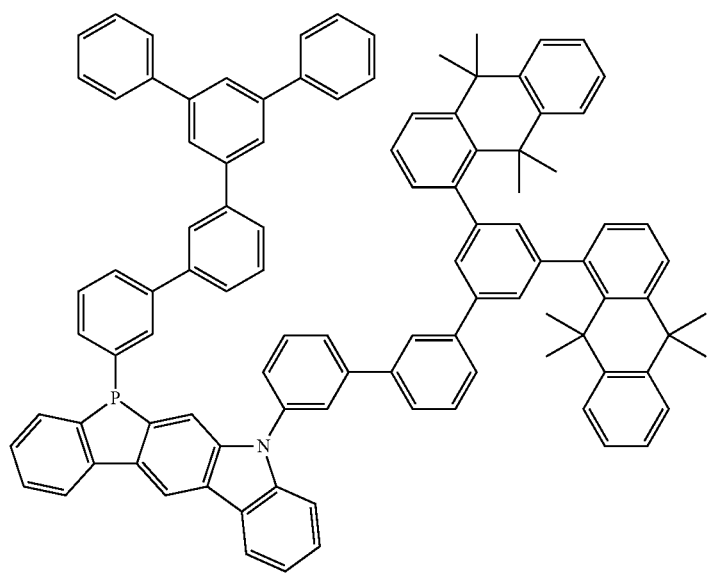

-continued
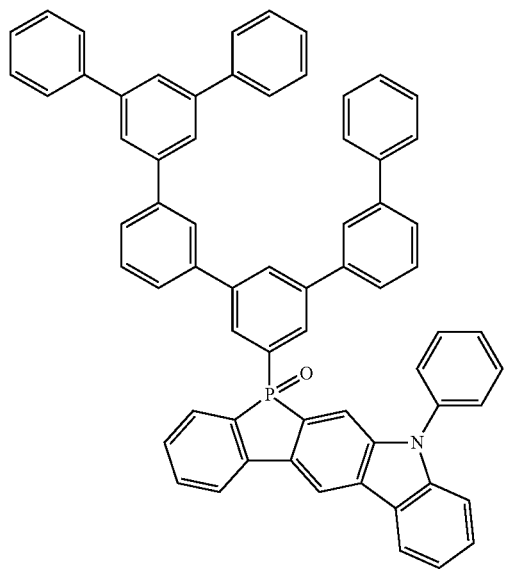
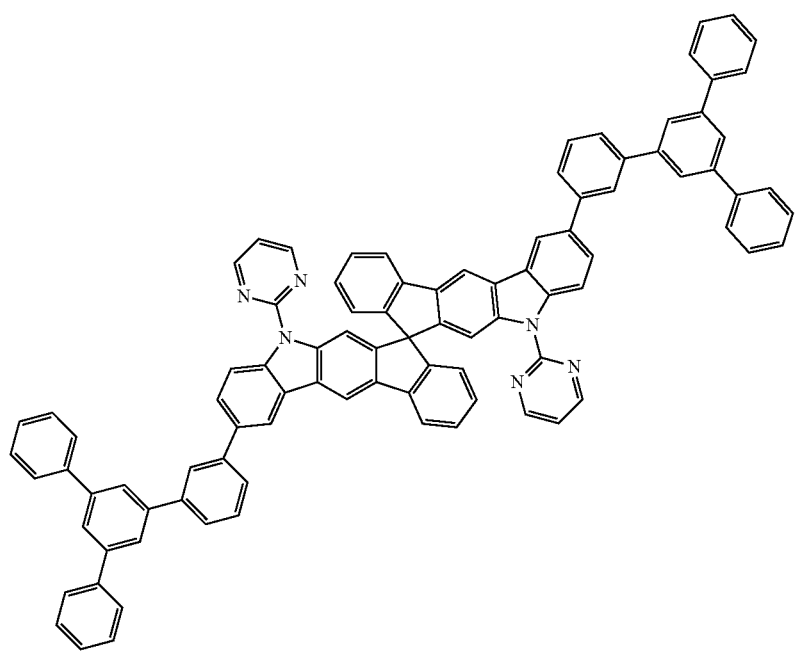

-continued
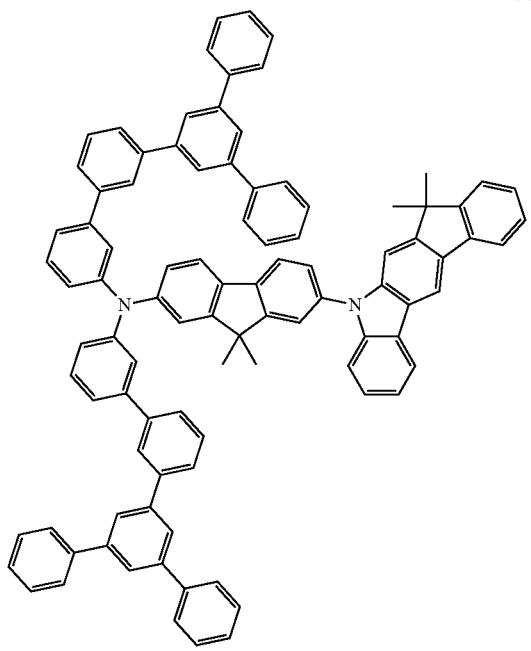
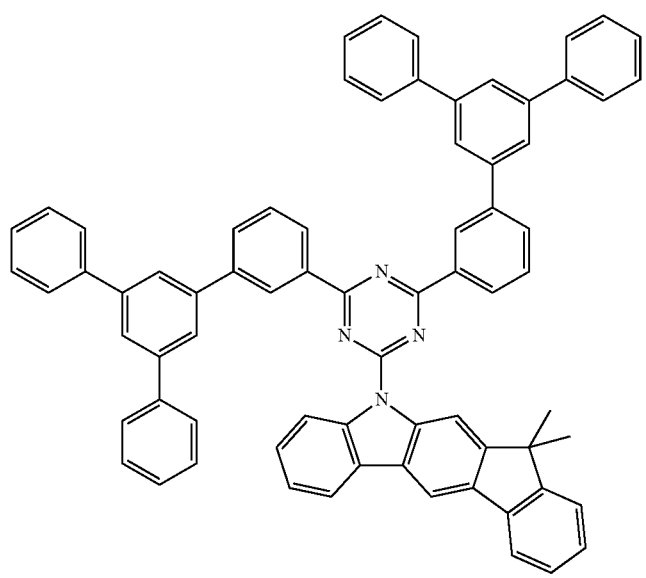

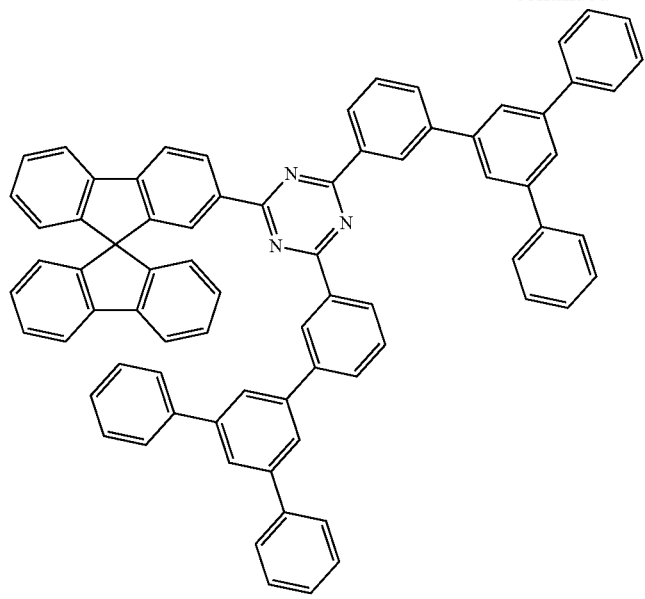
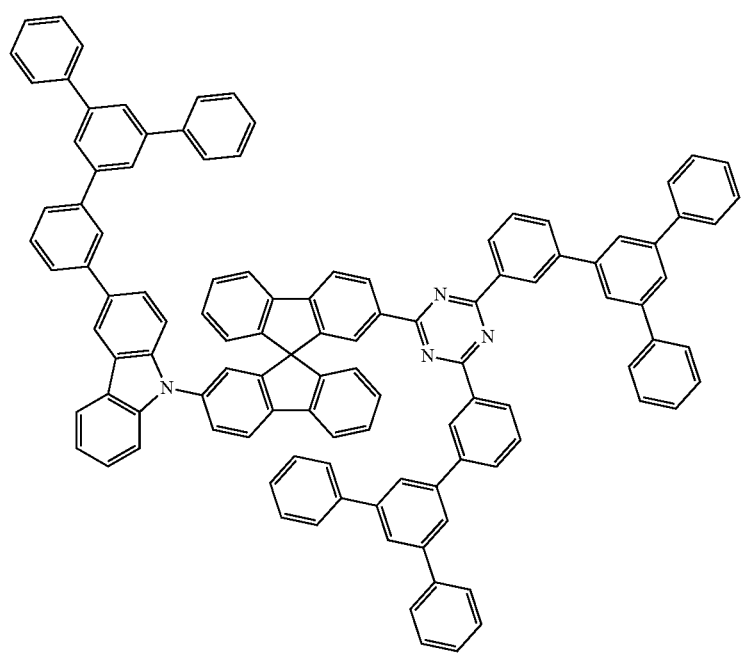

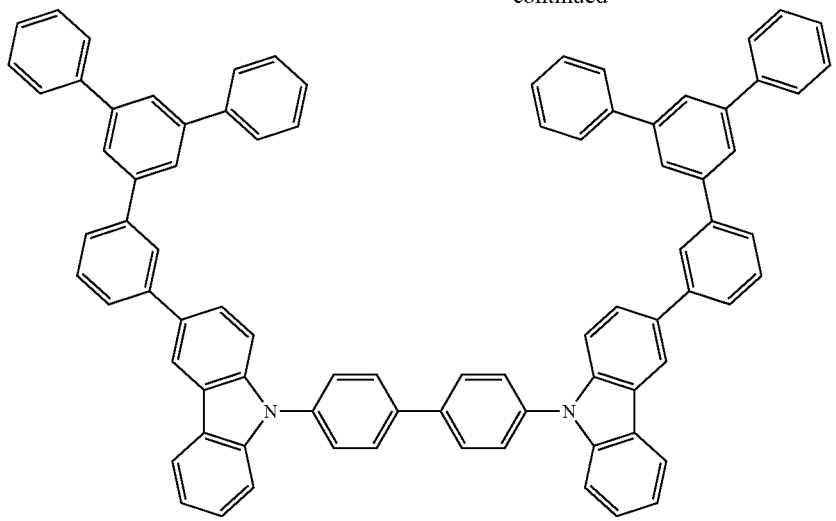
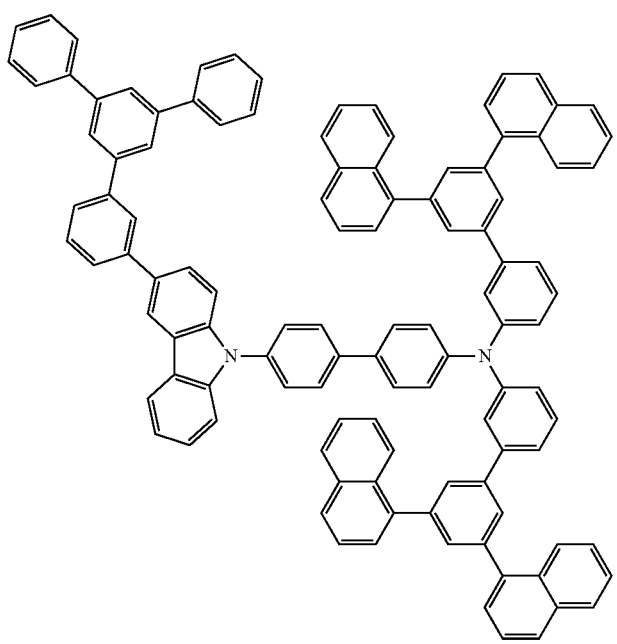

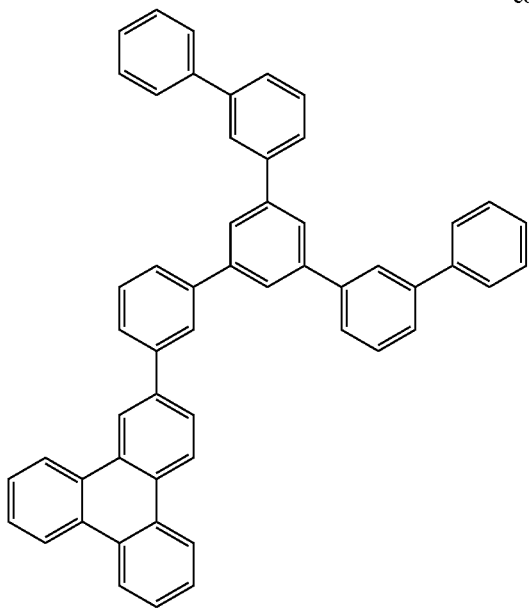
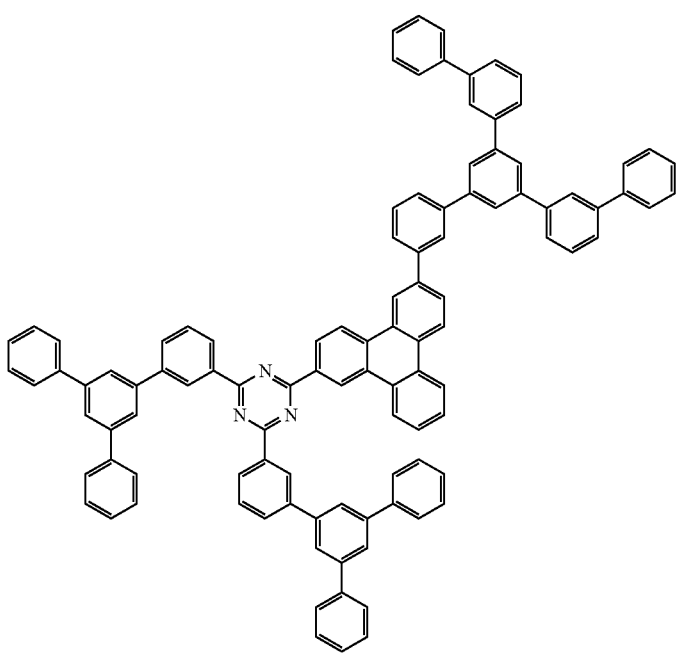

-continued
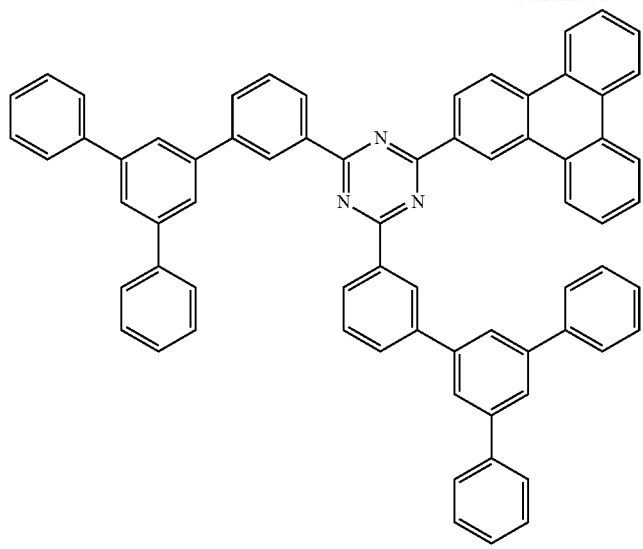
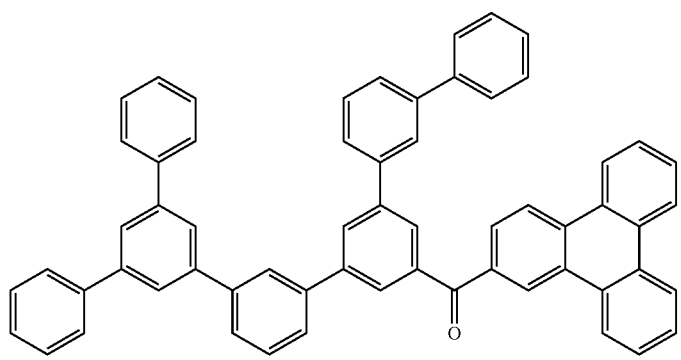
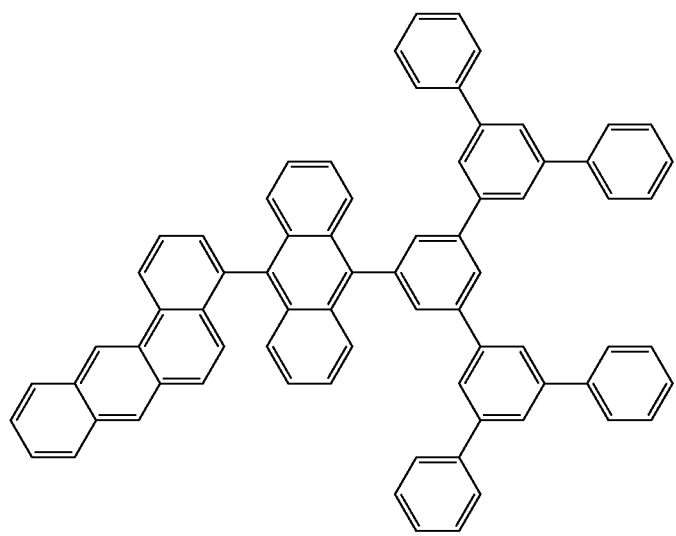

-continued
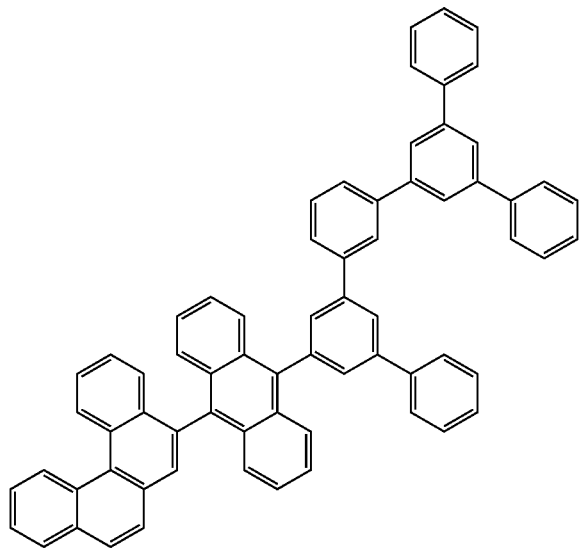
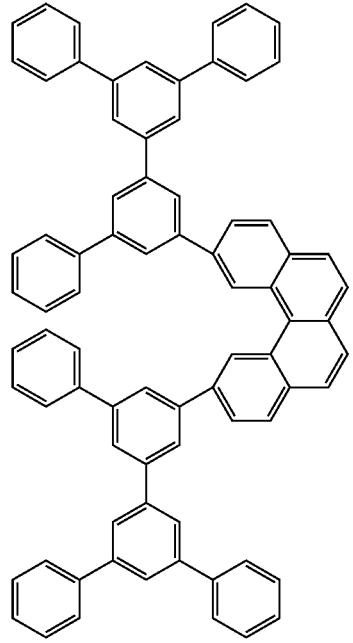
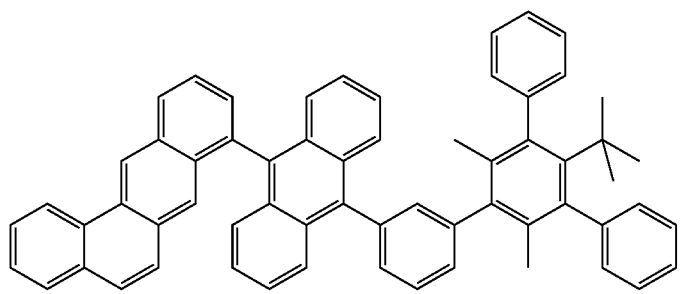
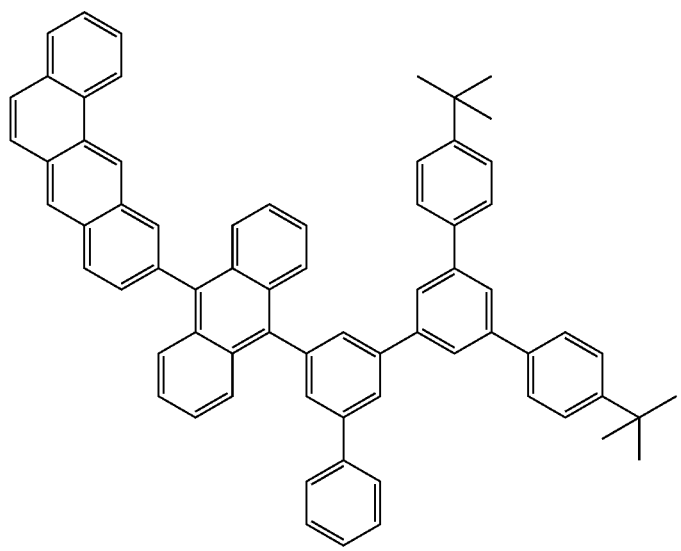

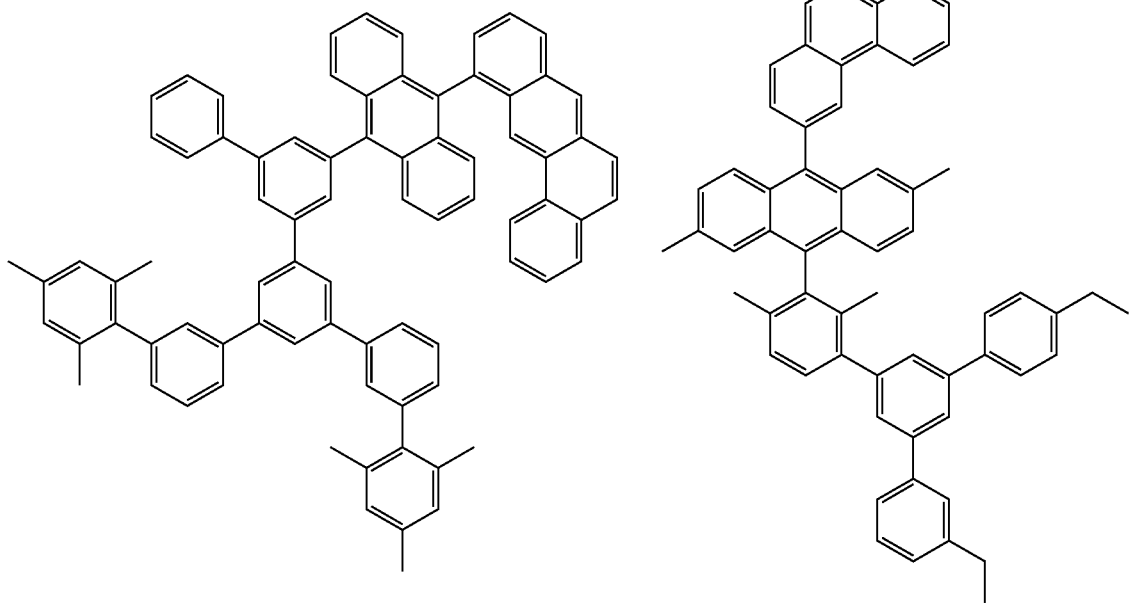
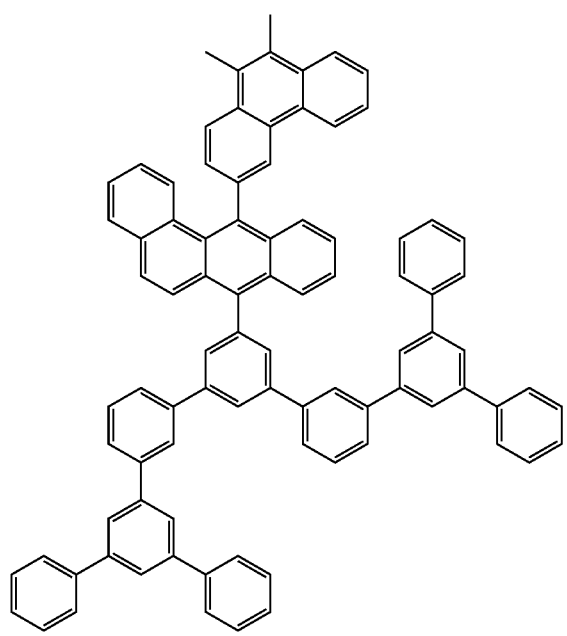

-continued
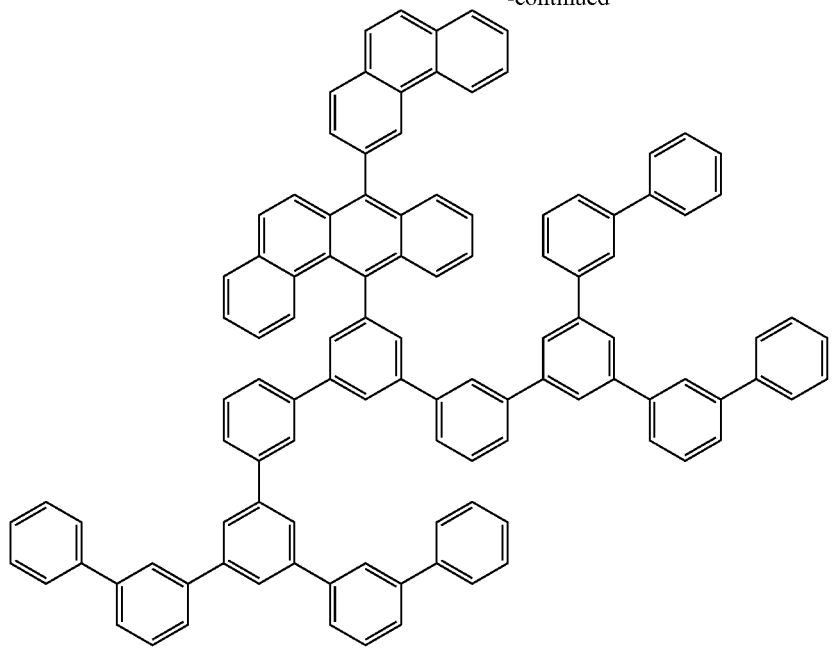
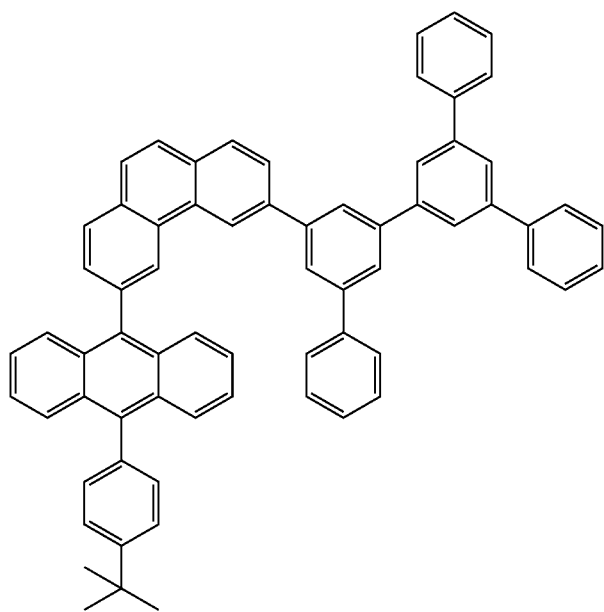

-continued
101
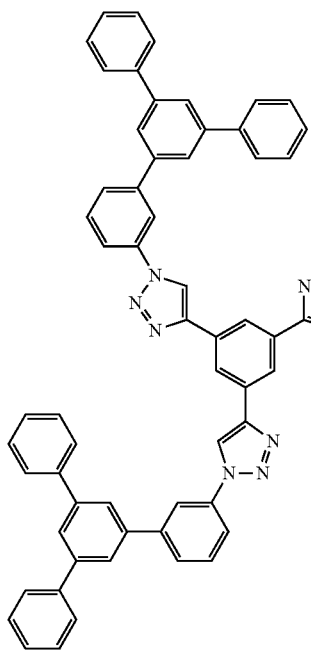
102
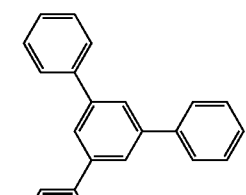
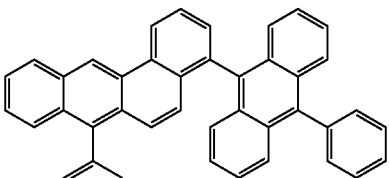
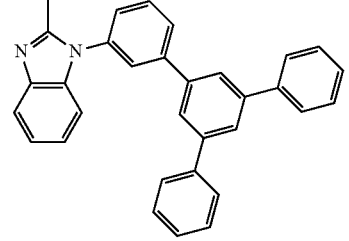
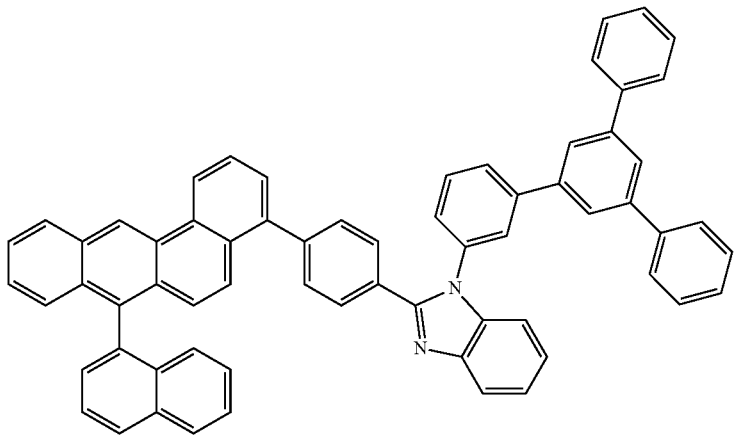
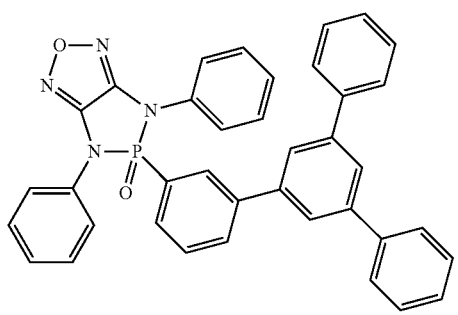

-continued
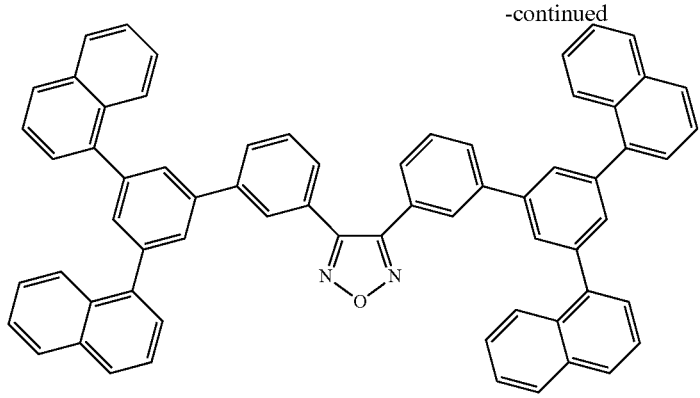
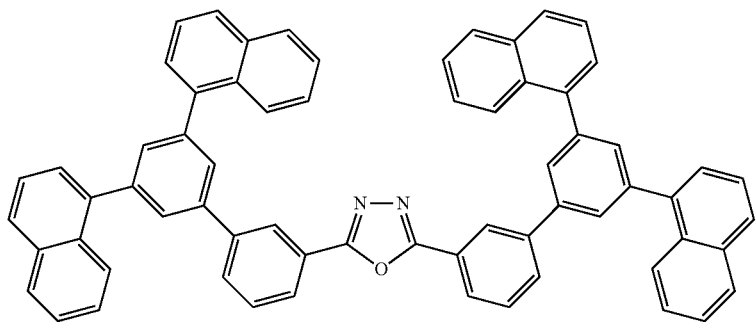
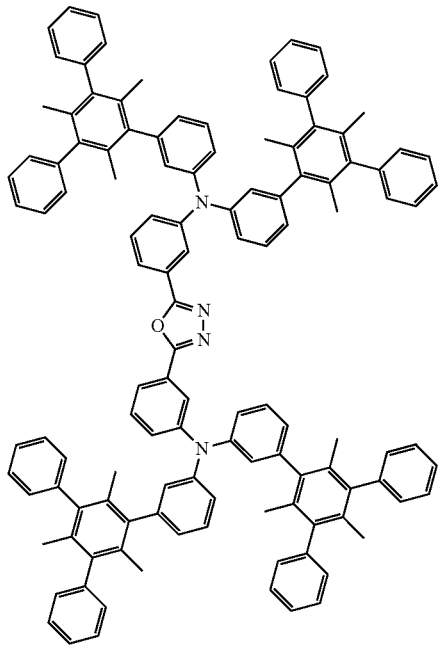
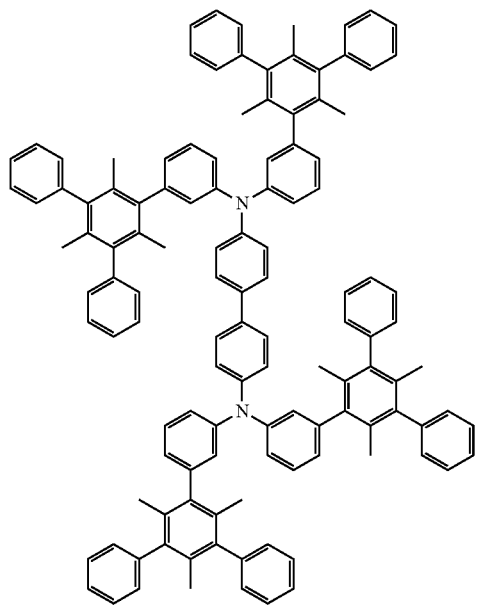
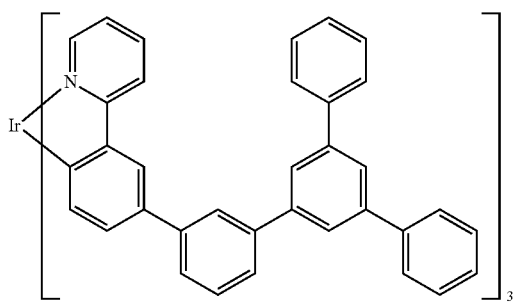
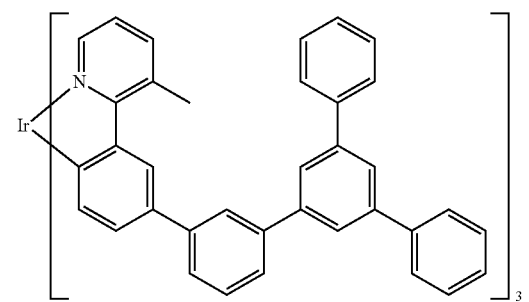

-continued
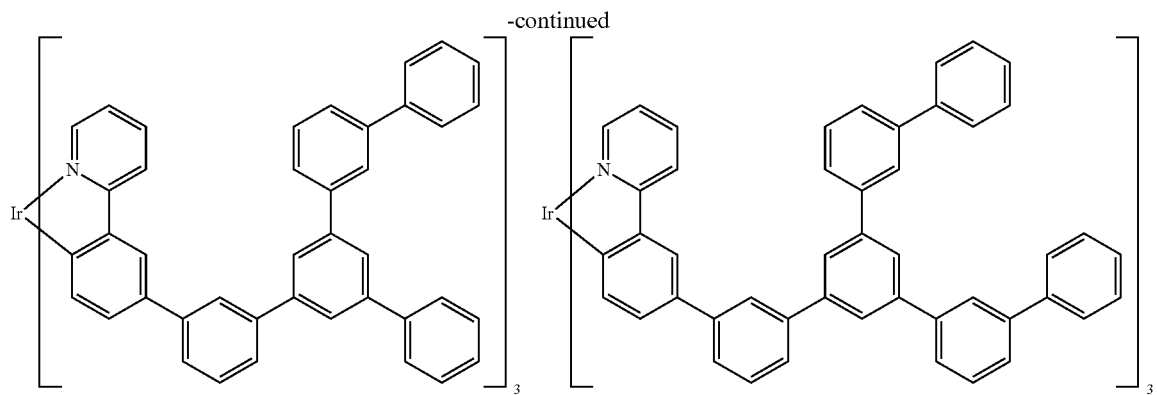
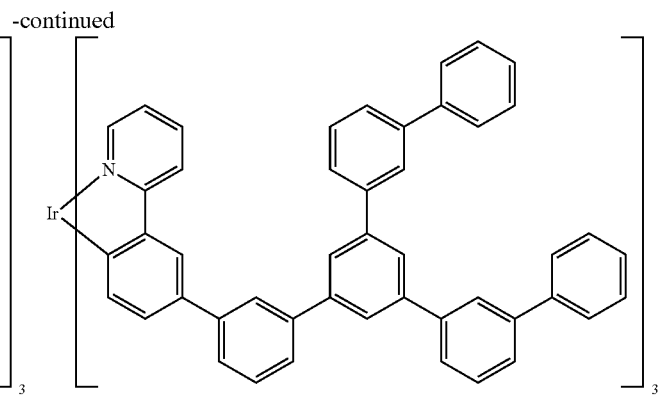
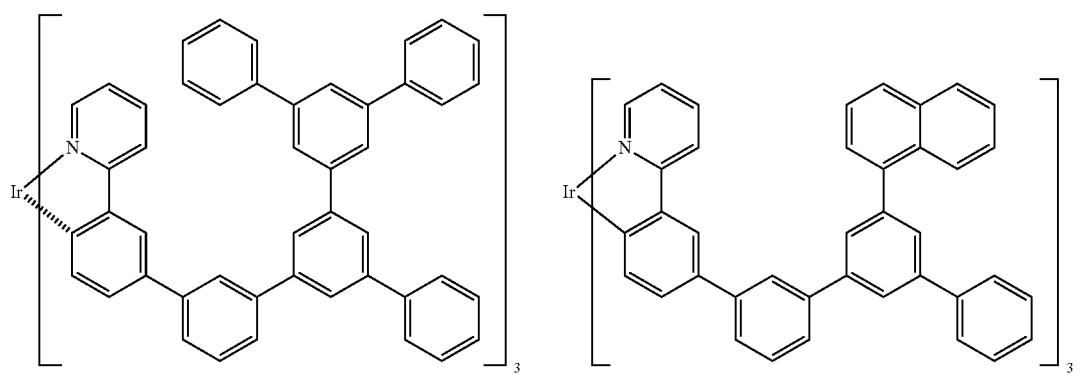
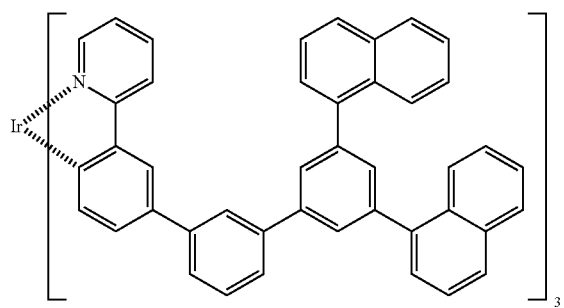
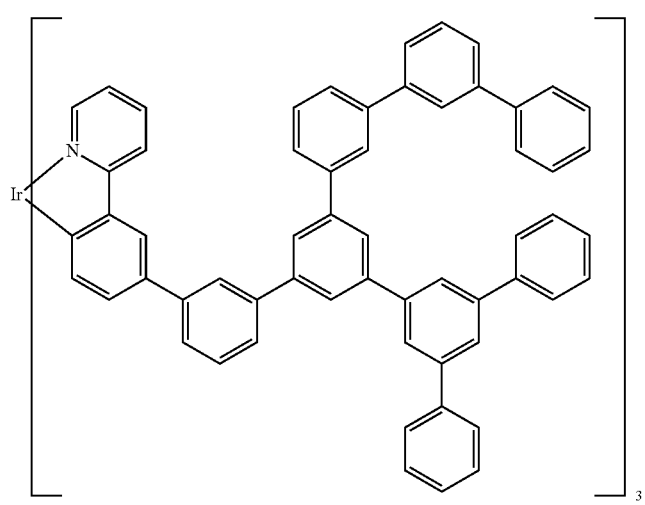

107 108
-continued
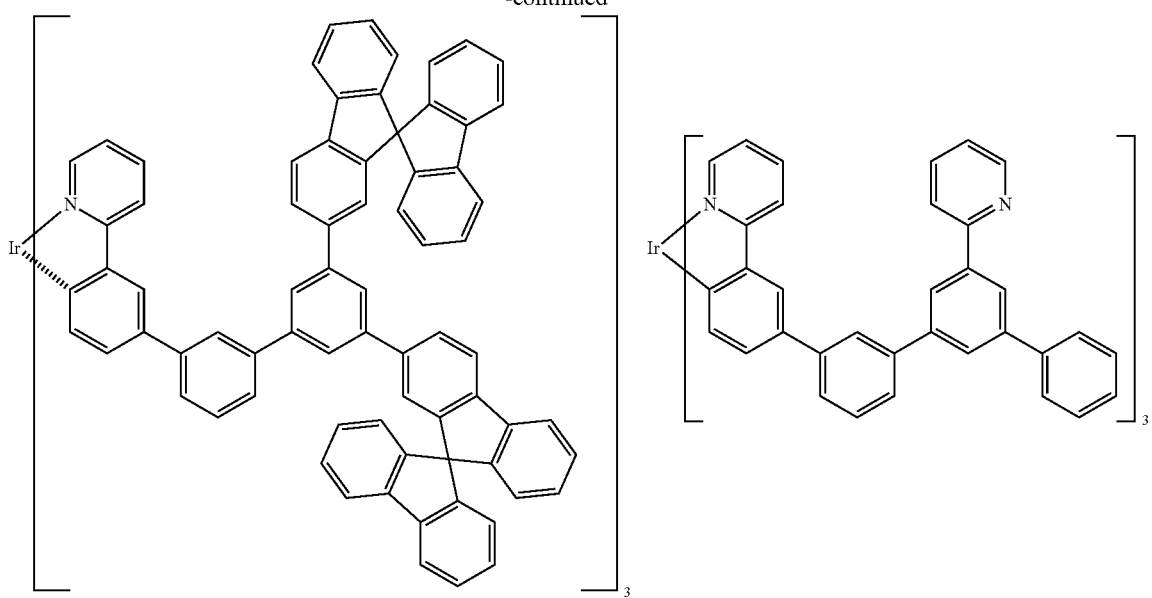
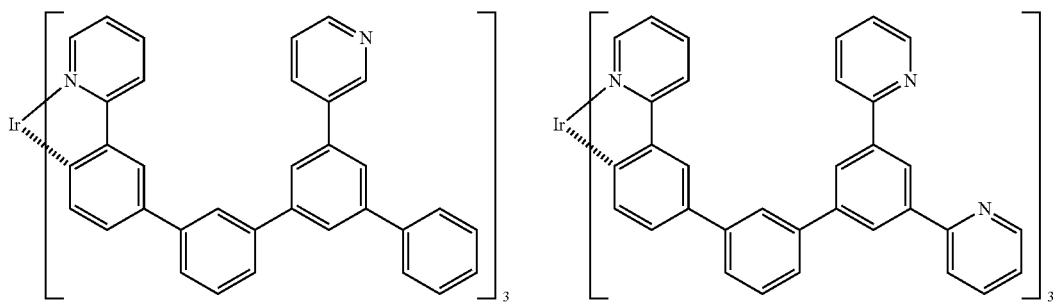
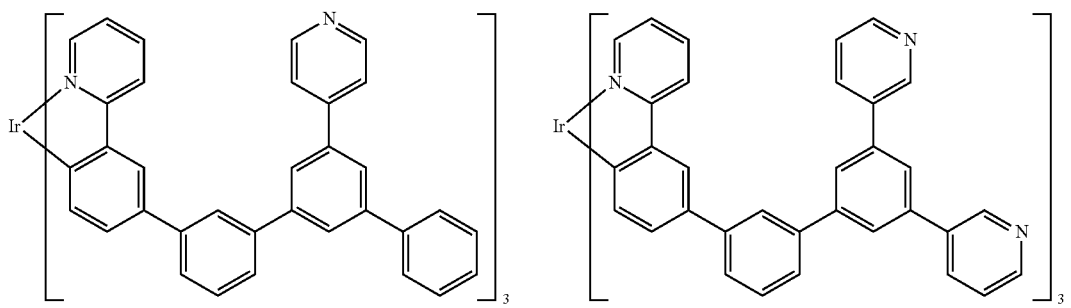
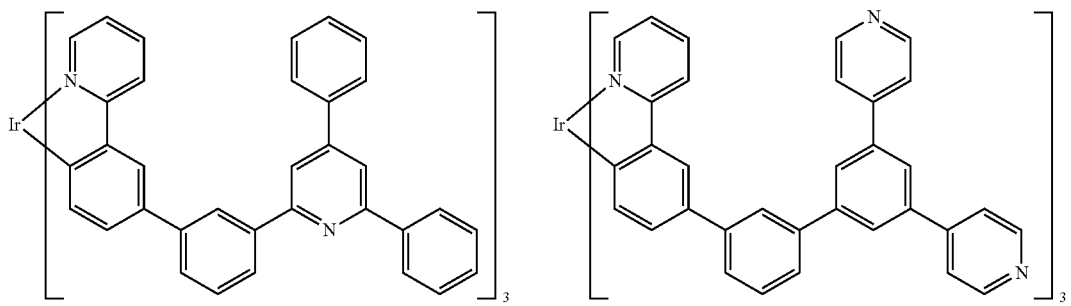

-continued
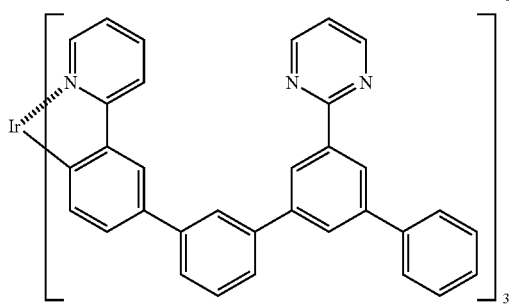
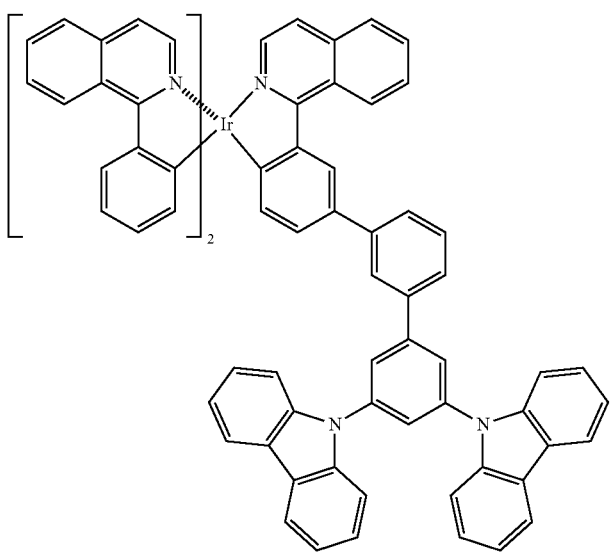
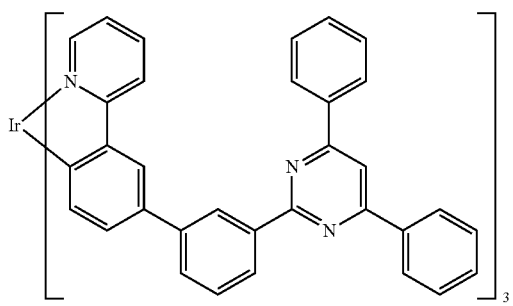
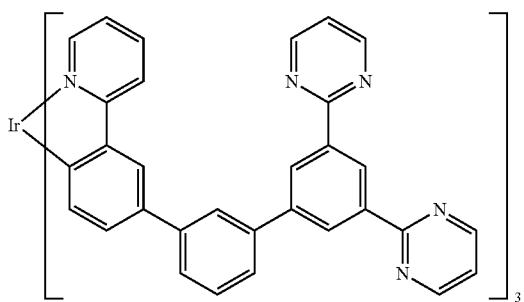
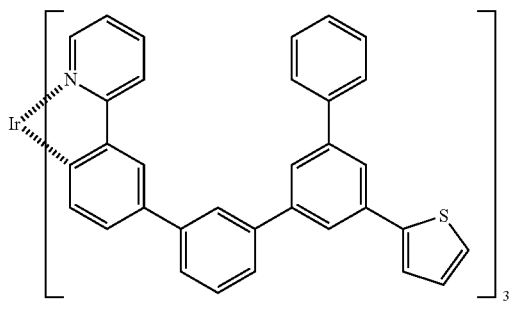
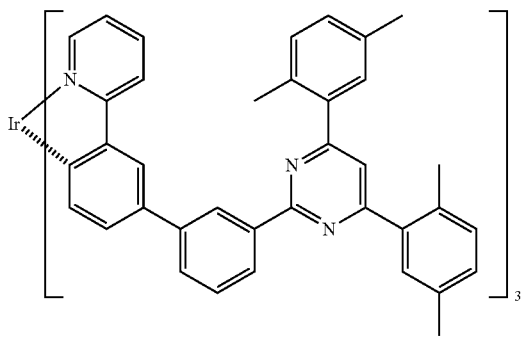

111
-continued
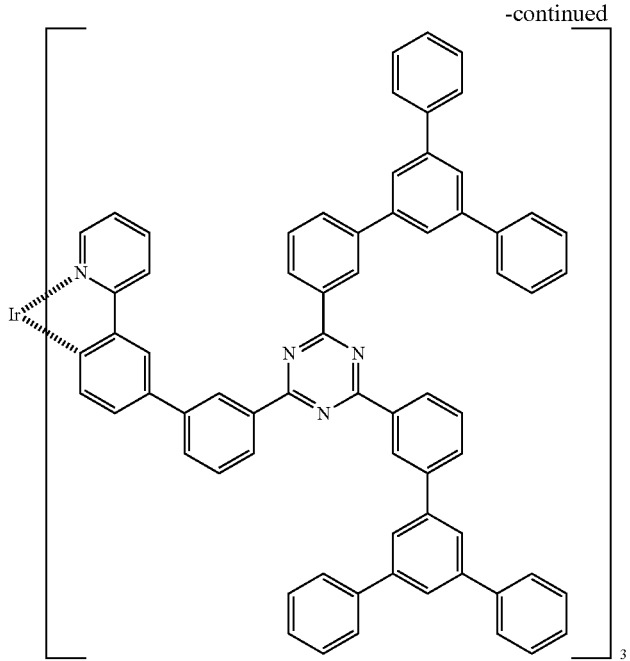
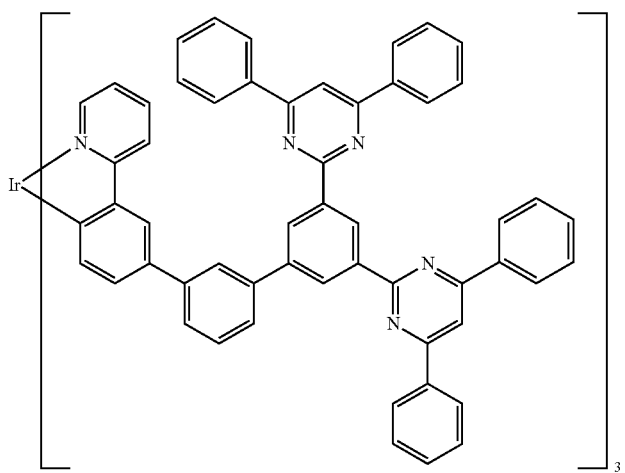
112
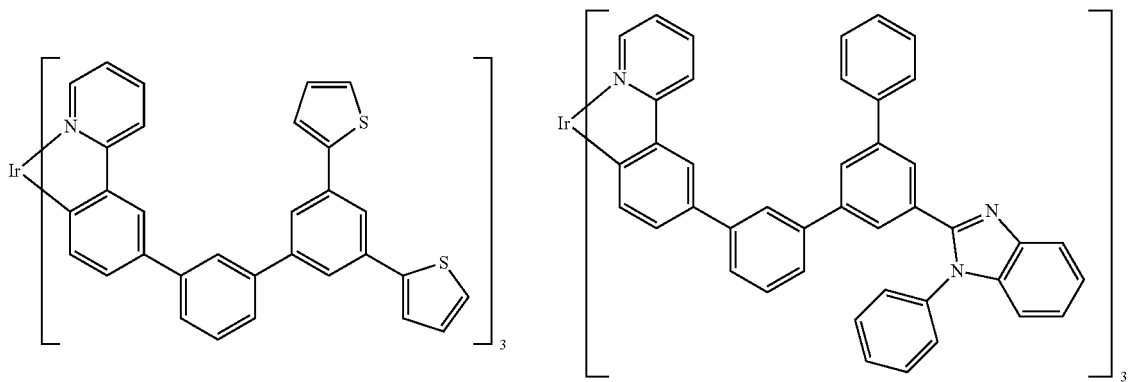

-continued
113
114
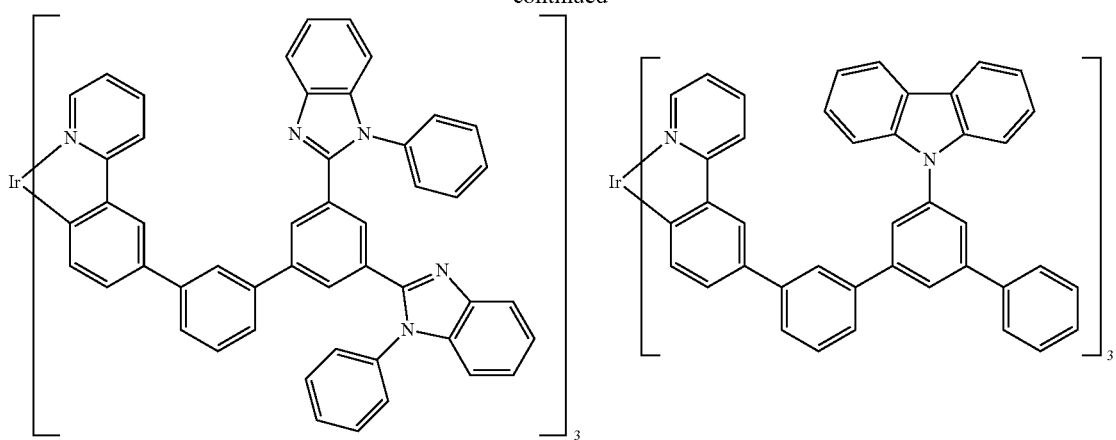
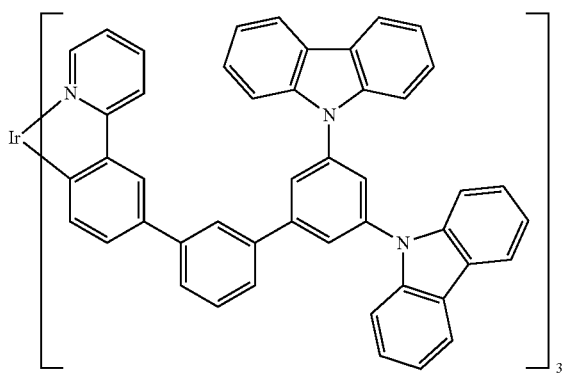
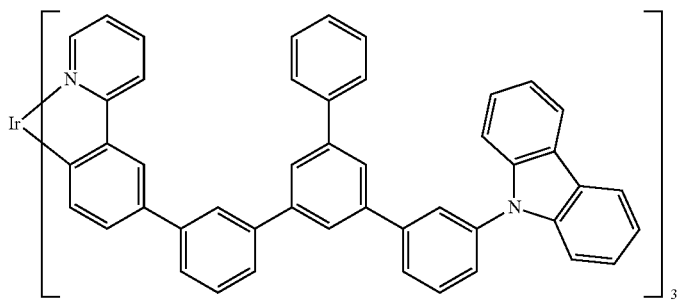
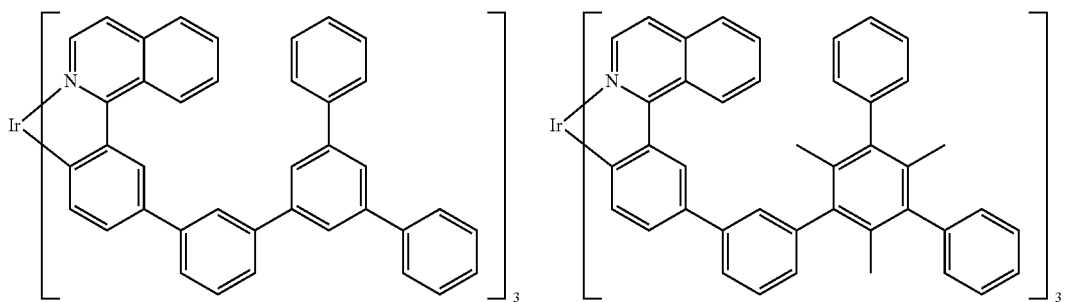

-continued
115
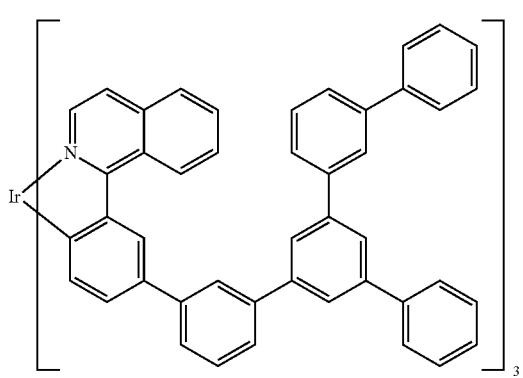
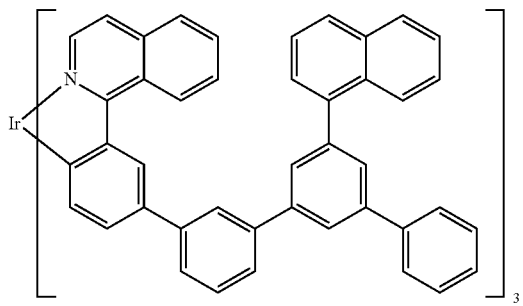
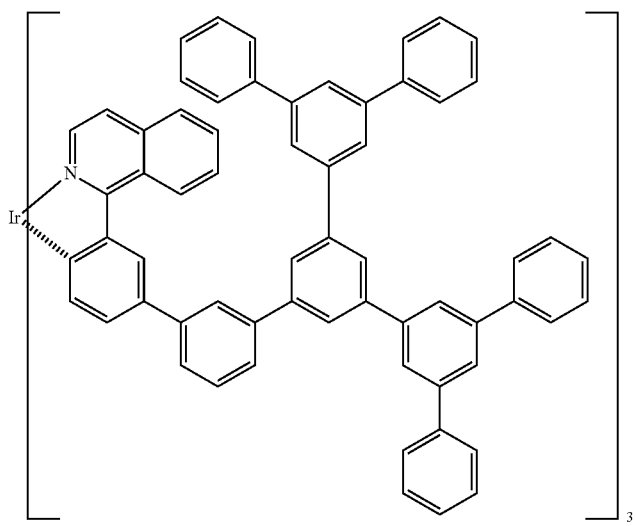
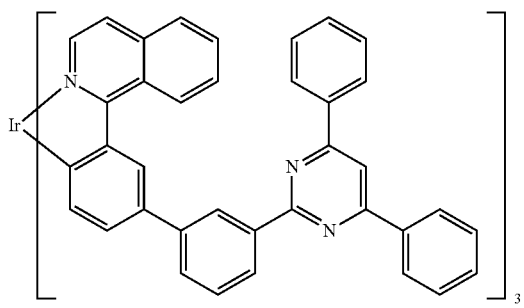
116
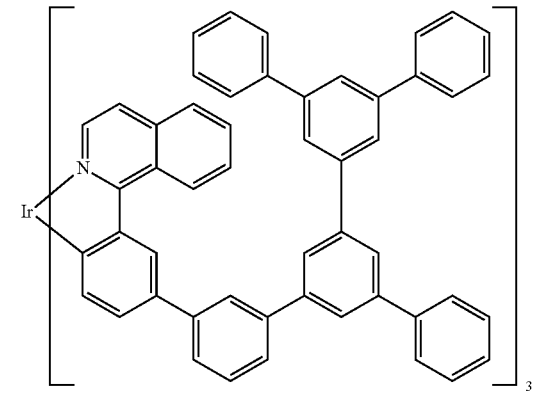
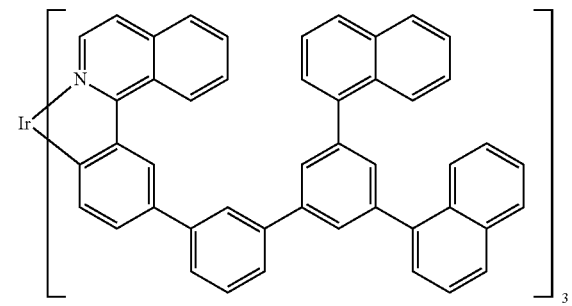
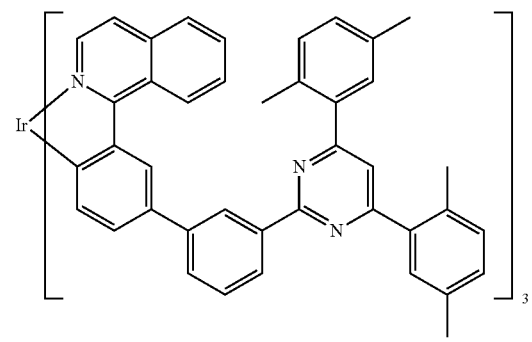

-continued
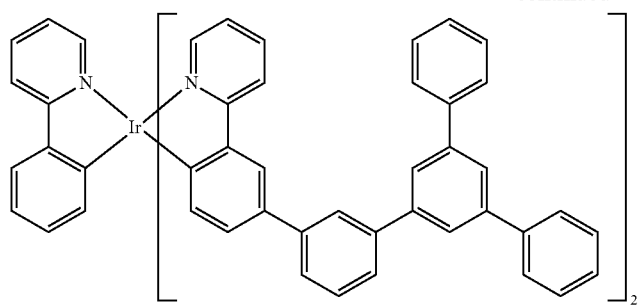
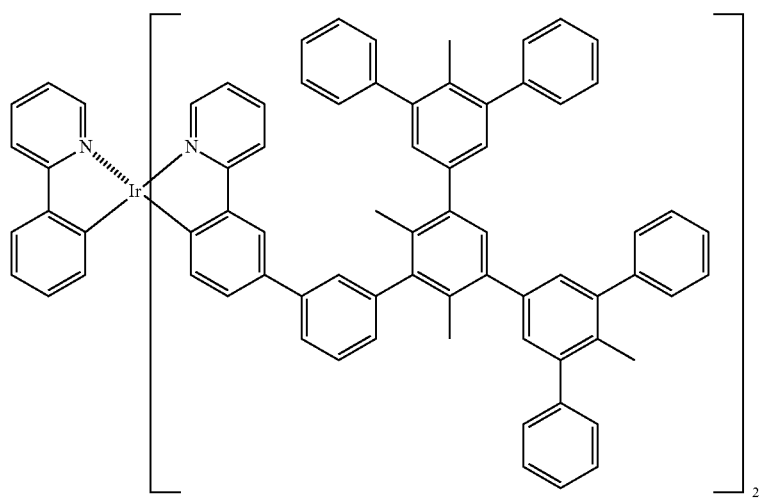
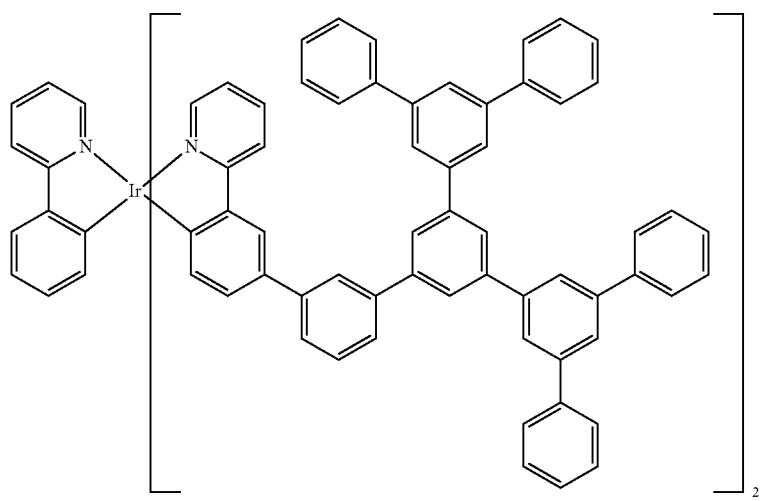
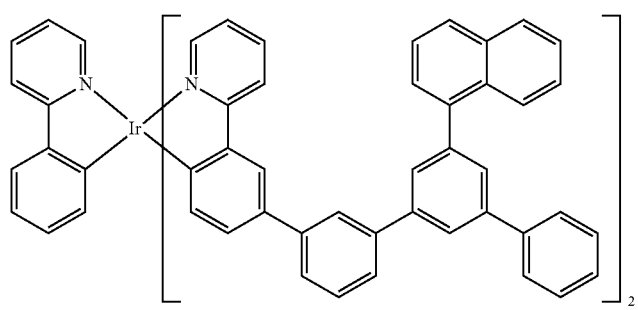

-continued
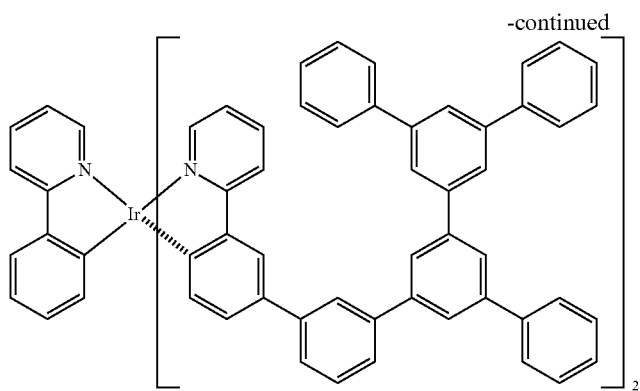
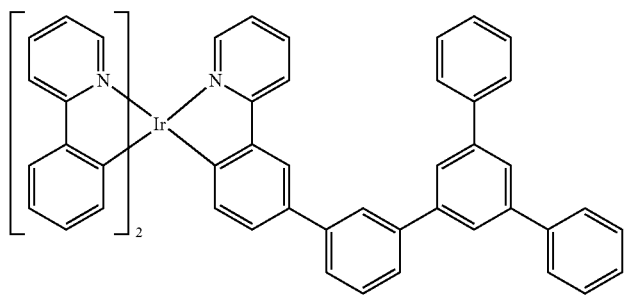
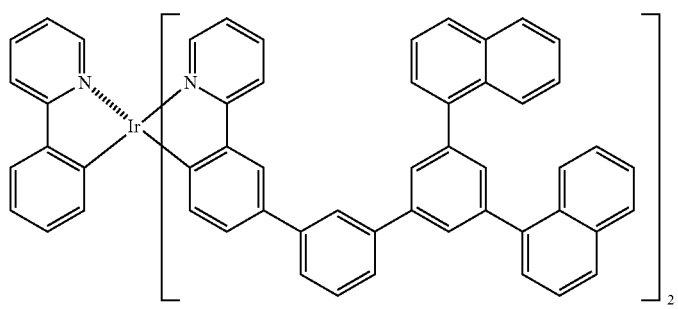
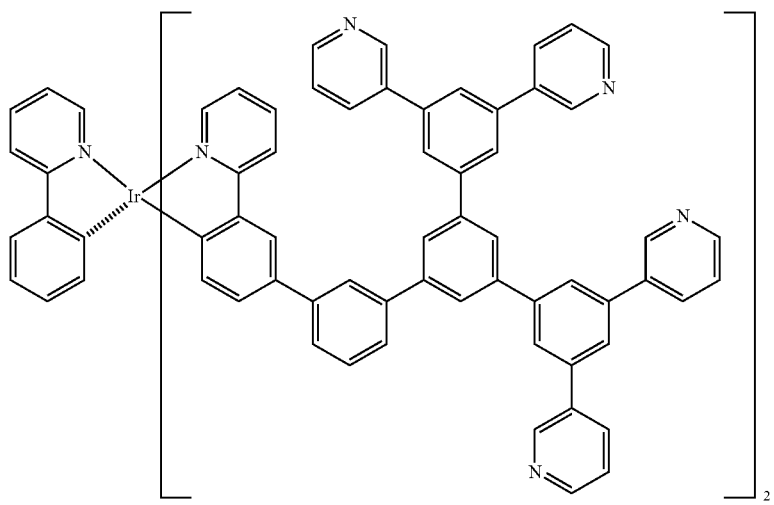

-continued
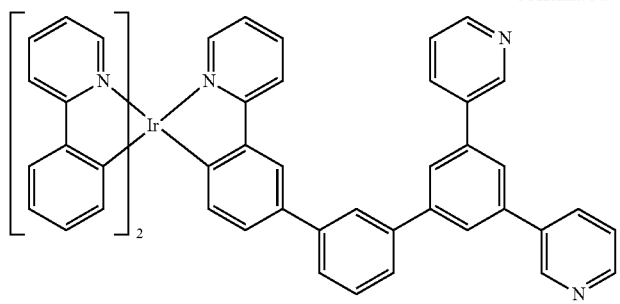
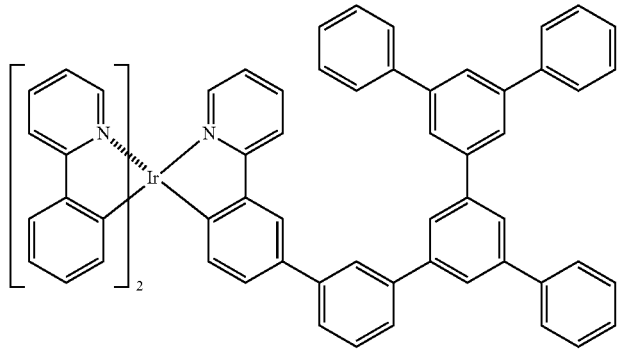
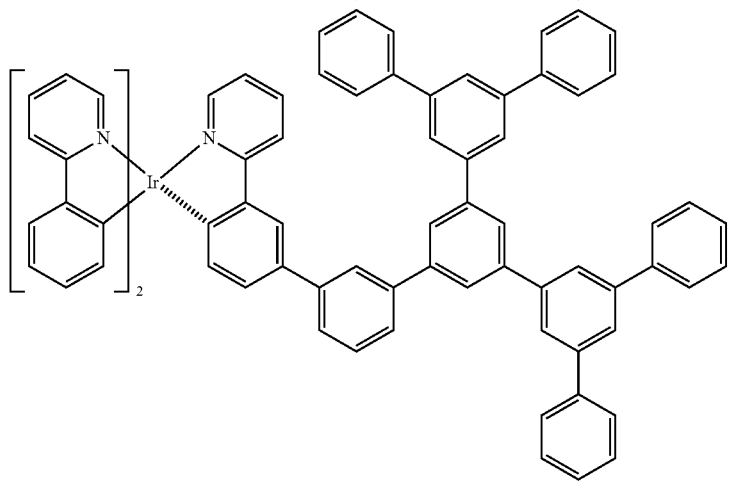
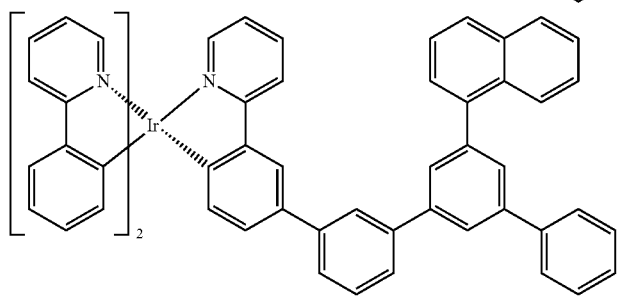
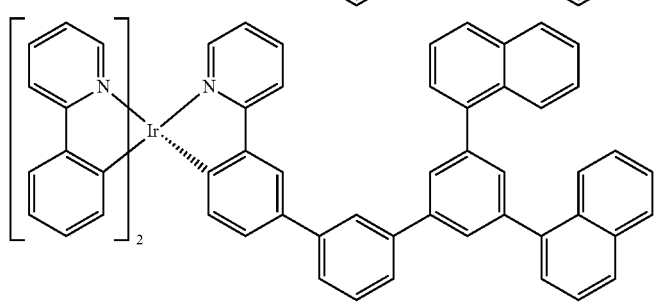

-continued
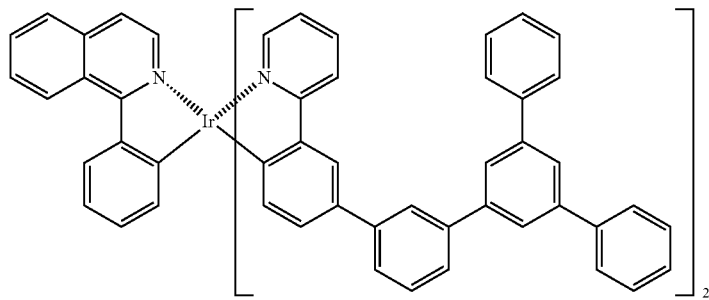
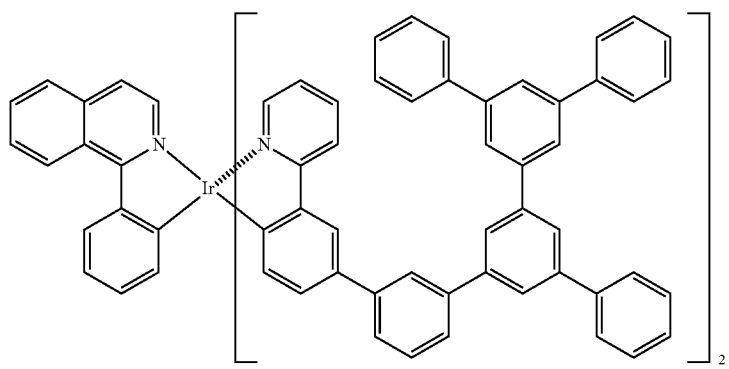
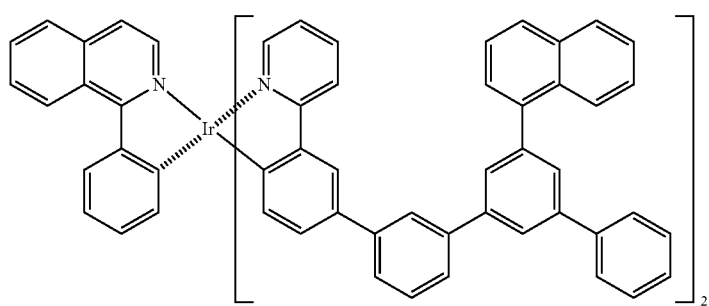
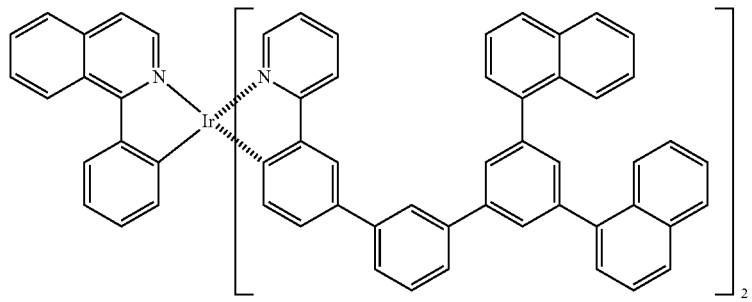

-continued
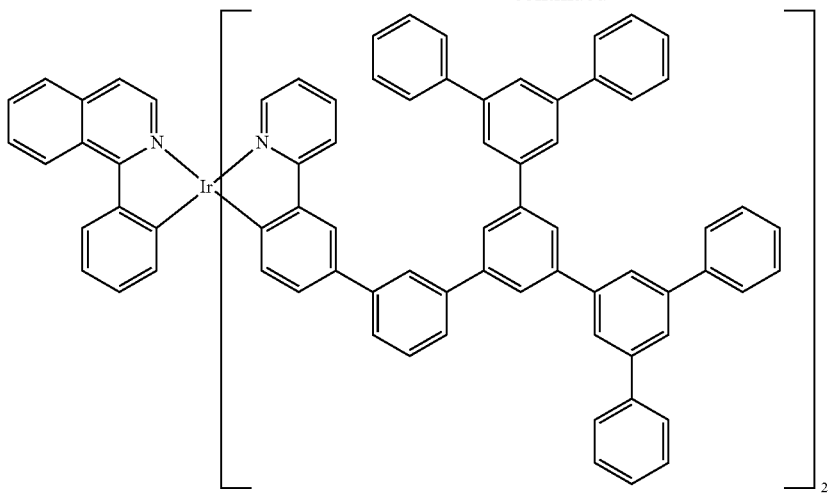
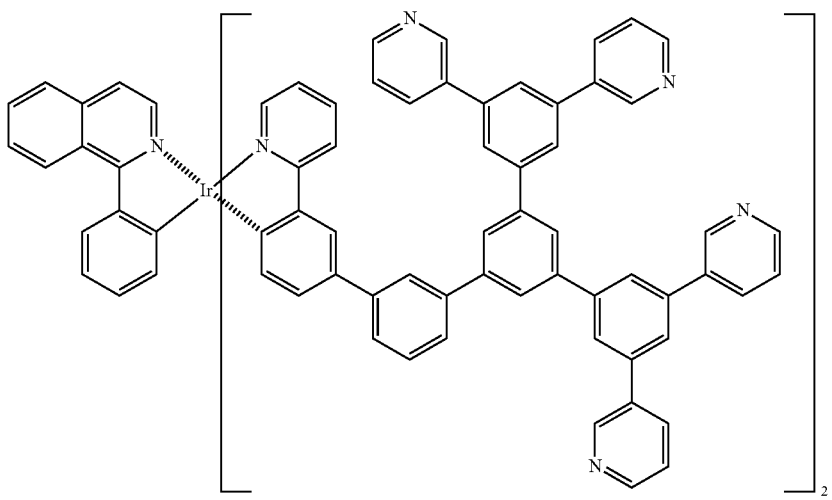
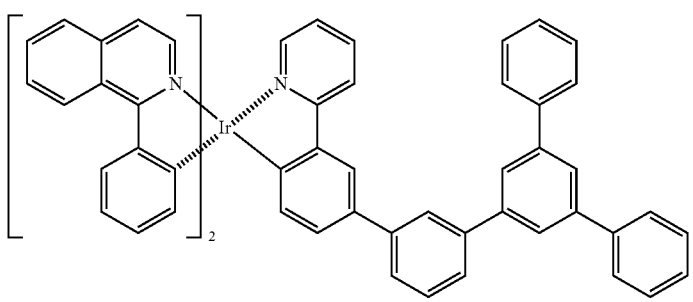
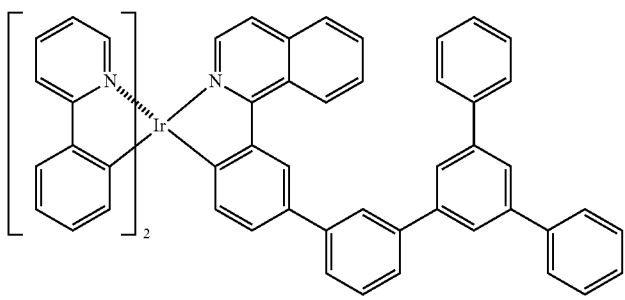

-continued
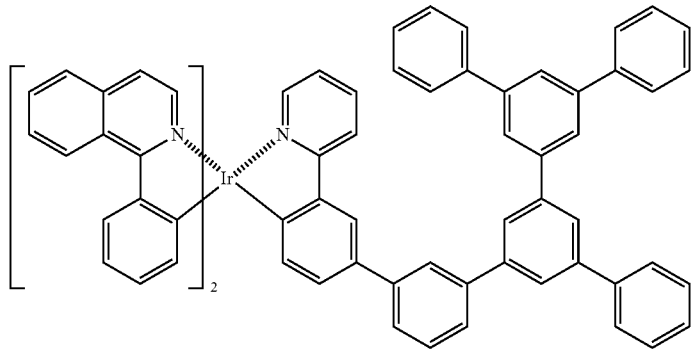
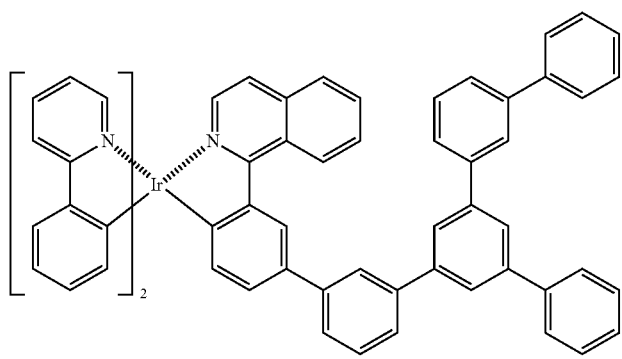
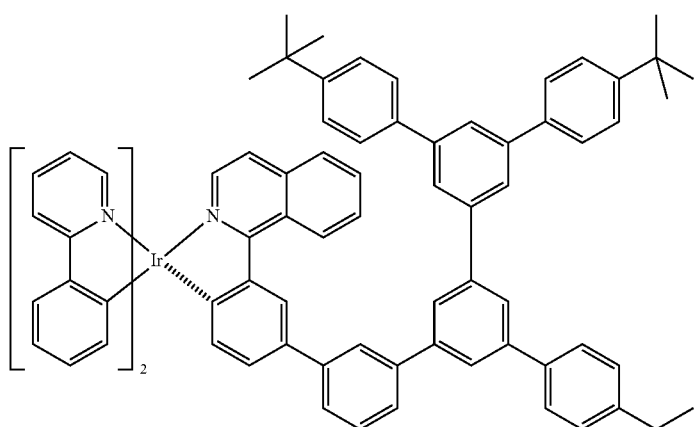
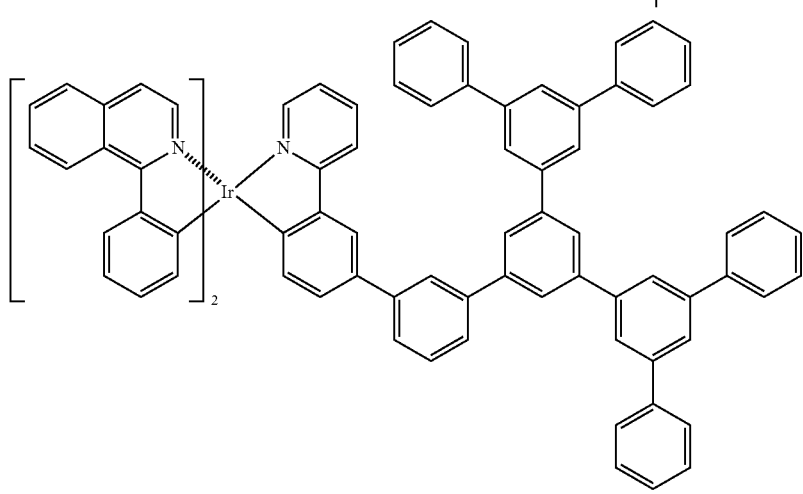

-continued
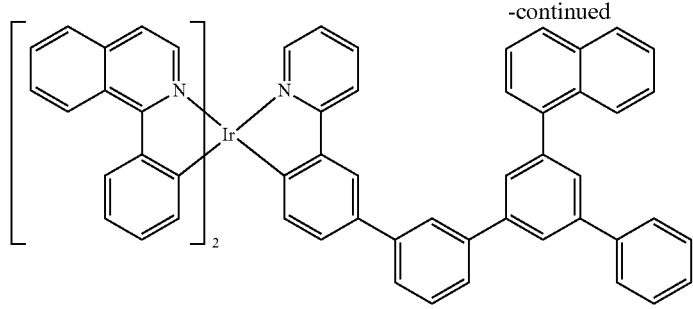
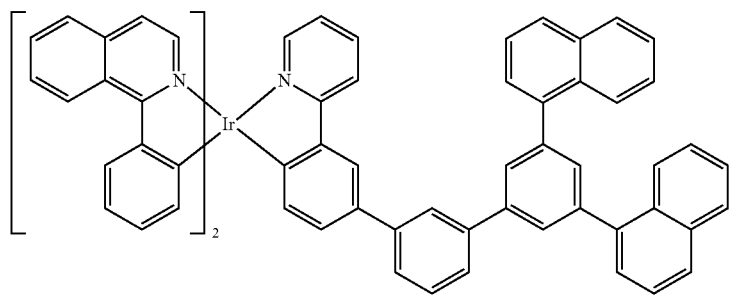
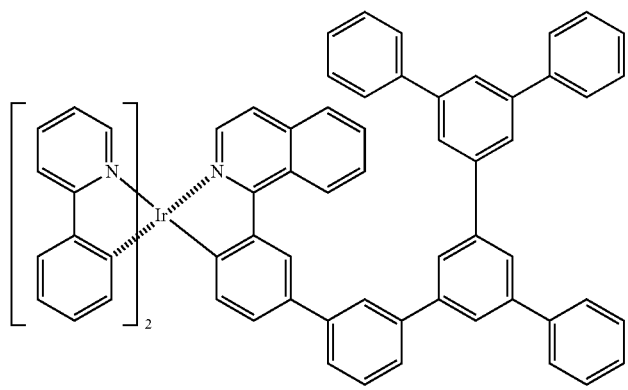
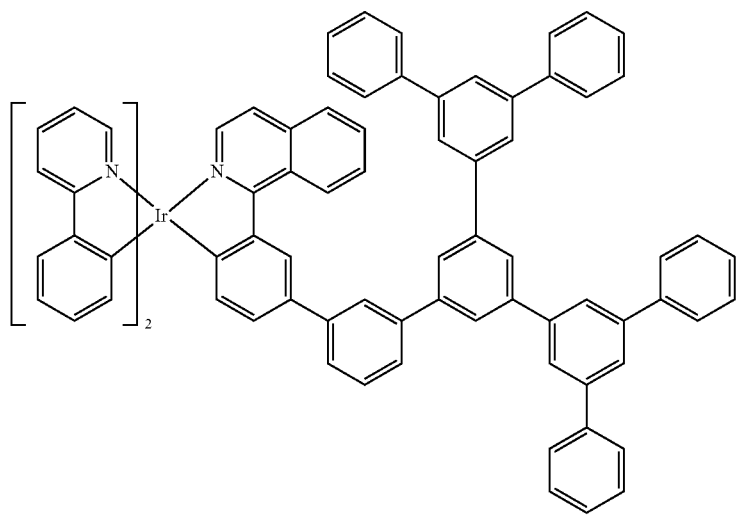

-continued
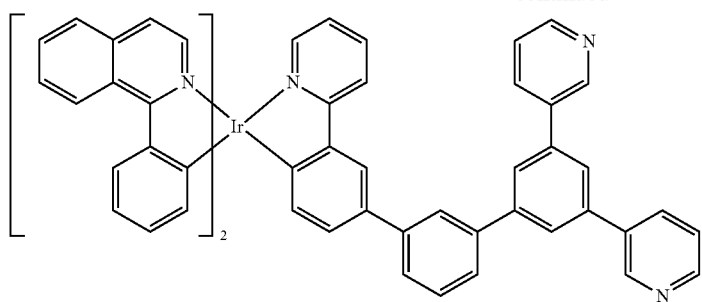
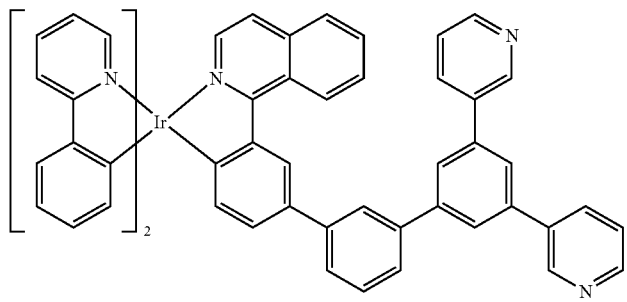
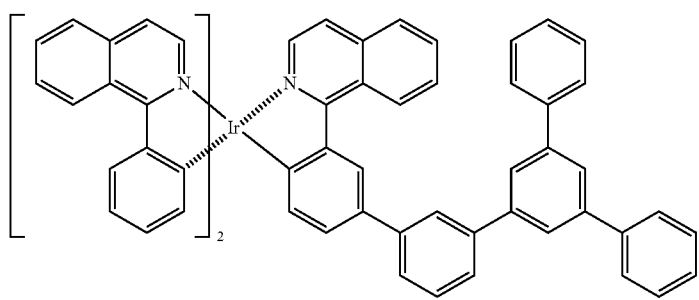
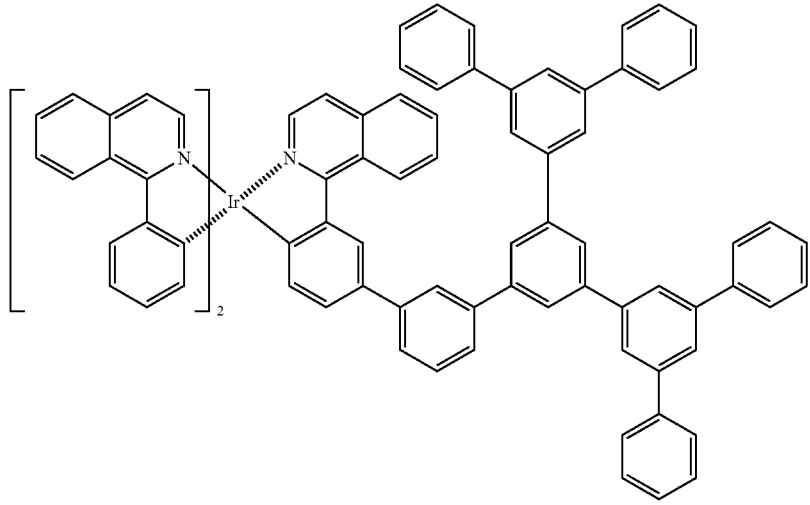
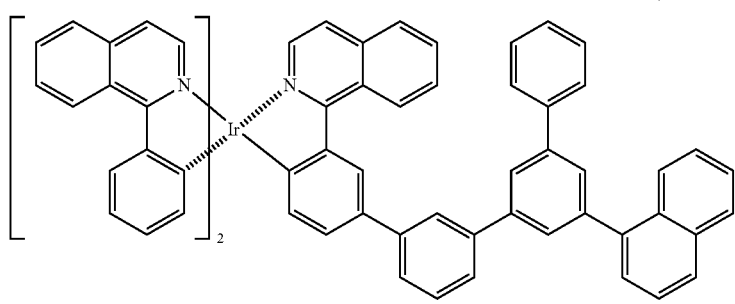

-continued
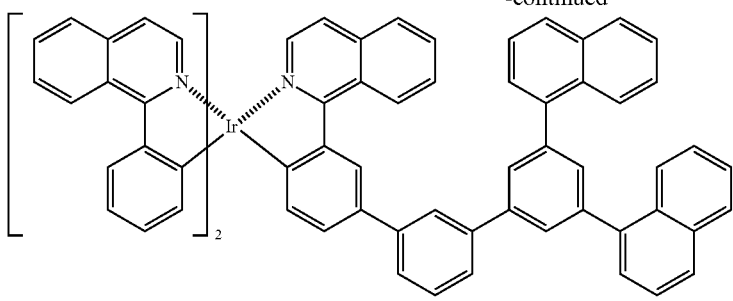
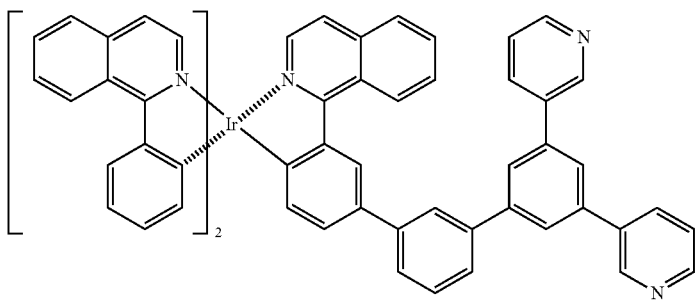
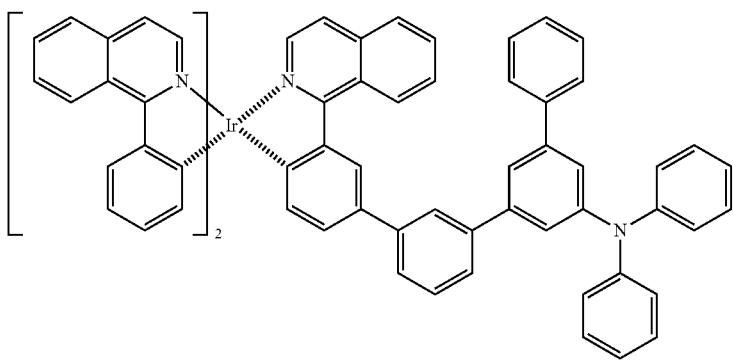
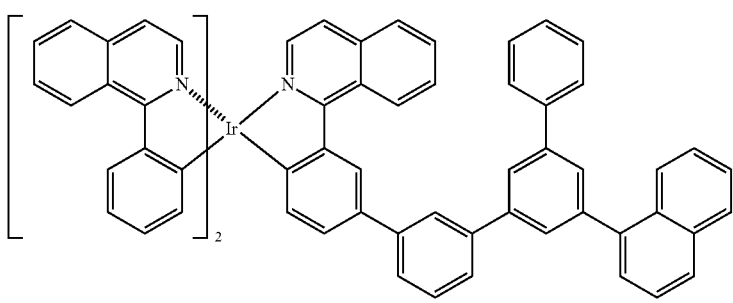
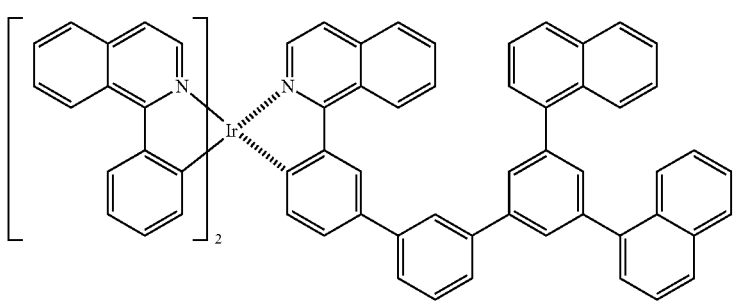

-continued
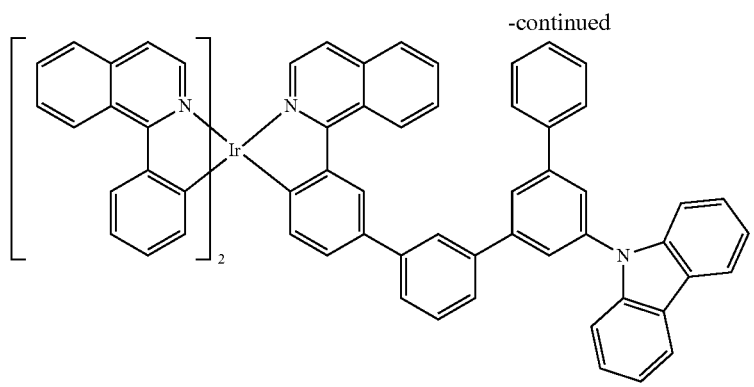
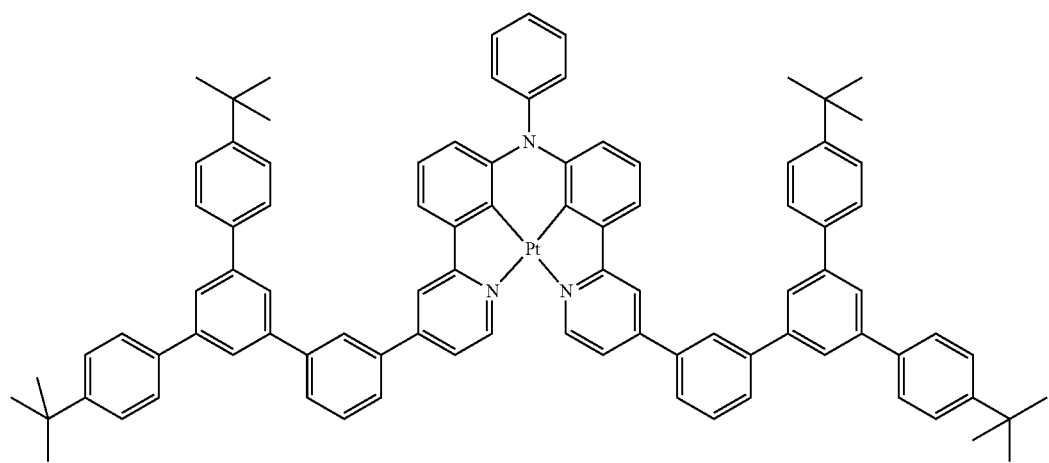
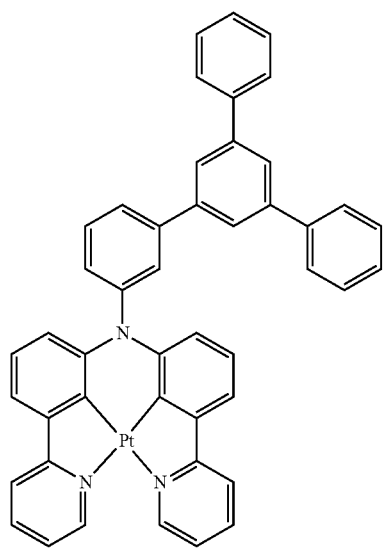

-continued

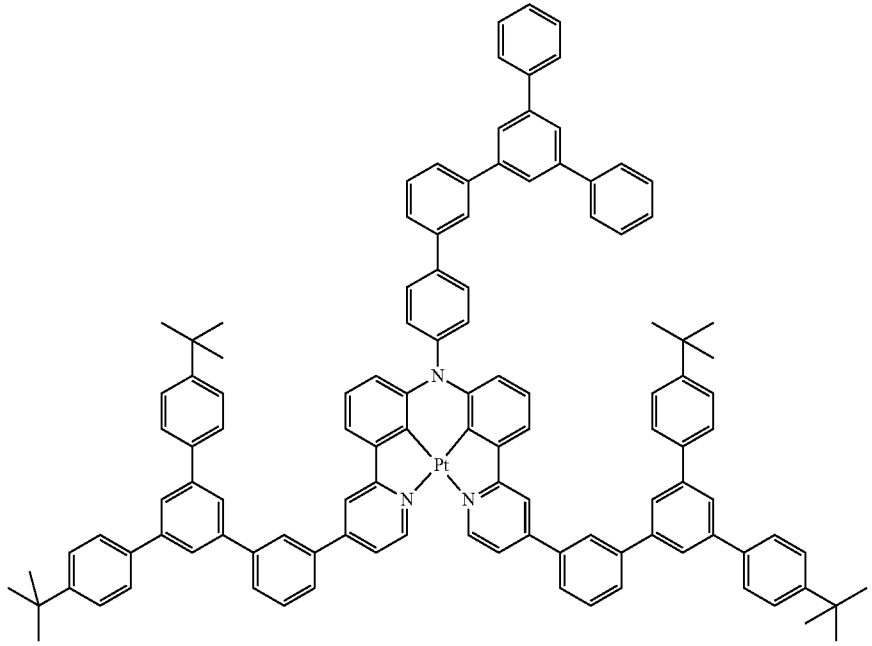

Besides the said components, the formulation according to the invention may comprise further additives and processing assistants. These include, inter alia, surface-active substances, surfactants, lubricants and greases, additives which increase the conductivity, dispersants, hydrophobicising agents, adhesion promoters, flow improvers, antifoams, deaerating agents, diluents, which may be reactive or unreactive, fillers, assistants, processing assistants, dyes, pigments, stabilisers, sensitisers, nanoparticles and inhibitors.

Compounds which contain the structural units according to the invention are used, for example, for the production of OLEDs or other electronic devices, preferably as hole-transport, hole-injection, emitter, electron-transport, electron-injection, charge-blocking and/or charge-generation layer.

The functional layers can be produced, for example, by coating from solution, preferably spin coating, or using any desired printing process, such as, for example, screen printing, flexographic printing or offset printing, but particularly preferably LITI (light induced thermal imaging, thermal transfer printing) or ink-jet printing.

The present invention also relates to the use of the functional compound in an organic, electronic device.

The organic, electronic device is preferably an organic electroluminescent device (OLED), a polymeric electroluminescent device (PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser).

For the purposes of the present invention, it is preferred for the functional compound according to the invention to be in the form of a layer (or to be present in a layer) in the electronic device.

The present invention thus also relates to a layer, in particular an organic layer, comprising one or more compounds as defined above.

In a further embodiment of the present invention, the device comprises a plurality of layers. The compound according to the invention can preferably be present here in a hole-transport, hole-injection, electron-transport, electron-injection and/or emission layer. Particular preference is given to the use of the compounds according to the invention in the hole-transport and/or emission layer.

The present invention accordingly also relates to an electronic device which comprises at least three layers, but in a preferred embodiment all said layers, from hole-injection, hole-transport, emission, electron-transport, electron-injection, charge-blocking and/or charge-generation layer and in which at least one layer comprises a compound to be employed in accordance with the invention. The thickness of the layers, for example the hole-transport and/or hole-injection layer, can preferably be in the range from 1 to 500 nm, particularly preferably in the range from 2 to 200 nm.

The device may furthermore comprise layers built up from further low-molecular-weight compounds or polymers. These can also be produced by evaporation of low-molecular-weight compounds in a high vacuum.

It may additionally be preferred to use the compounds to be employed in accordance with the invention not as the pure substance, but instead as a mixture (blend) together with further polymeric, oligomeric, dendritic or low-molecular-weight substances of any desired type. These may, for example, improve the electronic properties or emit themselves. The present application therefore likewise relates to mixtures of this type.

In a preferred embodiment of the present invention, the compounds according to the invention are employed as host materials or matrix materials in an emitting layer. The organic electroluminescent device here may comprise one or more emitting layers, where at least one emitting layer comprises at least one compound according to the invention, as defined above. If a plurality of emission layers are present, these preferably have a plurality of emission maxima between 380 nm and 750 nm, resulting overall in white emission, i.e. various emitting compounds which are able to fluoresce or phosphoresce are used in the emitting layers. Very particular preference is given to three-layer systems, where the three layers exhibit blue, green and orange or red emission (for the basic structure see, for example, WO 05/011013). White-emitting devices are suitable, for example, as backlighting of LCD displays or for general lighting applications.

Apart from these layers, the organic electroluminescent device may also comprise further layers, for example in each case one or more hole-injection layers, hole-transport layers, hole-blocking layers, electron-transport layers, electron-injection layers, exciton-blocking layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*).

Likewise, interlayers which have, for example, an exciton-blocking function may be introduced between two emitting layers. However, it should be pointed out that each of these layers does not necessarily have to be present. These layers may likewise comprise the compounds according to the invention, as defined above. It is also possible for a plurality of OLEDs to be arranged one above the other, enabling a further increase in efficiency with respect to the light yield to be achieved. In order to improve the coupling-out of light, the final organic layer on the light-exit side in OLEDs can, for example, also be in the form of a nanofoam, resulting in a reduction in the proportion of total reflection.

Preference is furthermore given to an organic electroluminescent device in which one or more layers are applied by means of a sublimation process, in which the materials are applied by vapour deposition in vacuum-sublimation units at a pressure below $10^{-5}$ mbar, preferably below $10^{-6}$ mbar, particularly preferably below $10^{-7}$ mbar.

Preference is likewise given to an organic electroluminescent device which is characterised in that one or more layers are applied by means of the OVPD (organic vapour phase deposition) process or with the aid of carrier-gas sublimation, in which the materials are applied at a pressure between $10^{-5}$ mbar and 1 bar.

Preference is furthermore given to an organic electroluminescent device which is characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or inkjet printing.

The device usually comprises a cathode and an anode (electrodes). The electrodes (cathode, anode) are selected for the purposes of the present invention in such a way that their band energies correspond as closely as possible to those of the adjacent, organic layers in order to ensure highly efficient electron or hole injection.

The cathode preferably comprises metal complexes, metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali-metal or alkaline-earth metal fluorides, but also the corresponding oxides (for example LiF, $Li_2O$, $BaF_2$, MgO, NaF, etc.). The layer thickness of this layer is preferably between 1 and 10 nm, particularly preferably between 2 and 8 nm.

The anode preferably comprises materials having a high work function. The anode preferably has a potential greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent in order to facilitate either irradiation of the organic material (O-SCs) or the coupling-out of light (OLEDs/PLEDs, O-lasers). A preferred structure uses a transparent anode. Preferred anode materials here are conductive, mixed metal oxides. Particular preference is given to indium tin oxide (ITO) or indium zinc oxide (IZO). Preference is furthermore given to conductive, doped organic materials, in particular conductive, doped polymers, such as, for example, poly(ethylenedioxythiophene) (PEDOT) and polyaniline (PANI).

The present invention likewise relates to a process for the production of an electronic device in which a formulation according to the invention is applied to a substrate and dried.

The solvent can preferably be removed at a temperature in the range from $-50°$ C. to $300°$ C., particularly preferably in the range from $20°$ C. to $250°$ C. The drying here can be carried out at a pressure in the range from $10^{-3}$ mbar to 1 bar, particularly preferably in the range from $10^{-2}$ mbar to 100 mbar.

The device is correspondingly structured, provided with contacts and finally hermetically sealed in a manner known per se, depending on the application, since the lifetime of such devices is drastically shortened in the presence of water and/or air.

The invention is explained in greater detail below with reference to working examples, but without being restricted thereby.

WORKING EXAMPLES

Example 1: Synthesis of Compounds 3 and 4

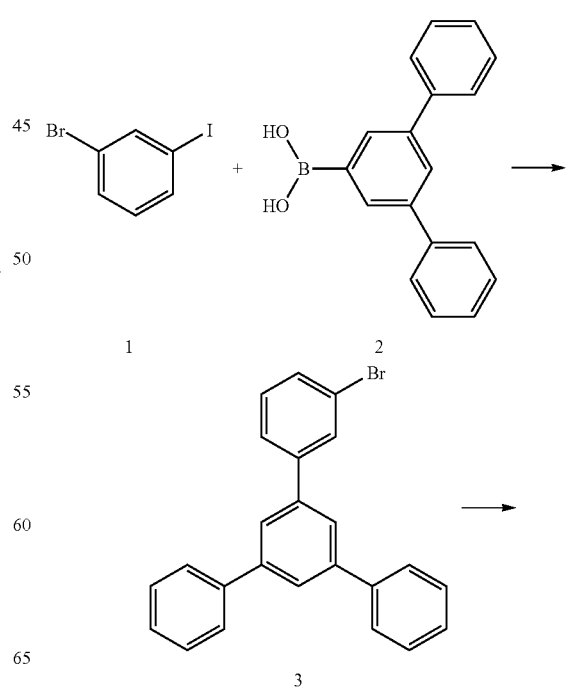

-continued

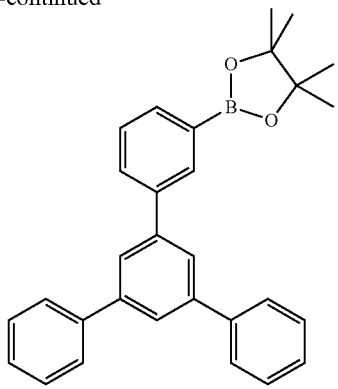

4

Synthesis of Compound 3

40.0 g (146 mmol) of 3-borono-[3,1';5,1"]terphenyl 2, 18.8 g (146 mmol) of 1-iodo-3-bromophenyl (1) and 109.3 g (730 mmol) of potassium carbonate are suspended in 1350 ml of toluene and 1150 ml of water. 844 mg (0.73 mmol) of tetrakis(triphenylphosphine)palladium(0) are added to this suspension, and the reaction mixture is heated under reflux for 16 hours. After cooling, the organic phase is separated off, washed three times with 200 ml of water, dried using sodium sulfate and subsequently evaporated to dryness. The residue is washed with ethanol and recrystallised from ethyl acetate and finally dried under reduced pressure. The yield is 47.6 g (123 mmol), corresponding to 84.5% of theory.

Synthesis of Compound 4

40.0 g (104 mmol) of 1-bromo-3-([3,1';5,1"]terphen-1-yl) benzene 3, 29.0 g (114 mmol) of bispinacolatodiboron, 29.5 g (301 mmol) of potassium acetate are suspended in 800 ml of dimethyl sulfoxide. 4.24 g (5.2 mmol) of 1,1-bis(diphenylphosphino)ferrocenepalladium(II) dichloride DCM are added to this suspension, and the reaction mixture is heated under reflux for 16 hours. After cooling, 600 ml of ethyl acetate and 400 ml of water are added, and the organic phase is separated off, washed three times with 200 ml of water, dried using sodium sulfate and subsequently evaporated to dryness. The crude product is recrystallised from heptane and finally dried under reduced pressure. The yield is 34.5 g (80 mmol), corresponding to 46.1% of theory.

Example 2: Synthesis of Compounds 5 to 8

Synthesis of Compound 5

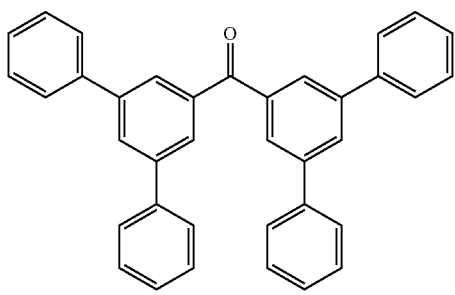

5

74.7 g (150 mmol) of bis(3,5-dibromophenyl) ketone, 109.7 g (900 mmol) of phenylboronic acid, 267.5 g (1162 mmol) of tripotassium phosphate monohydrate, 5.5 g (18 mmol) of tri-o-tolylphosphine and 673.5 mg (3 mmol) of palladium(II) acetate are suspended in a mixture of 600 ml of toluene, 300 ml of dioxane and 750 ml of water and heated under reflux for 72 hours. After cooling, the organic phase is separated off, washed three times with water and dried over sodium sulfate. The mixture is subsequently filtered through aluminium oxide, evaporated to about 200 ml, and 500 ml of ethanol are added, whereupon the crude product precipitates. The solid is filtered off with suction and washed with 100 ml of ethanol, then dissolved in boiling toluene and re-precipitated by addition of hot ethanol. The yield is 44.0 g (90 mmol), corresponding to 60.2% of theory.

Synthesis of Compound 6

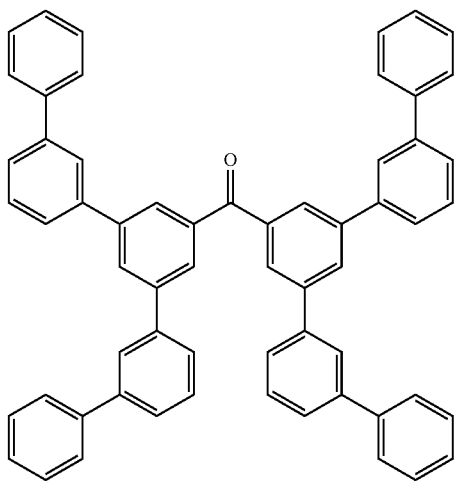

6

The synthesis is carried out analogously to compound 5, with phenylboronic acid being replaced by 3-bromobiphenyl. The yield is 84.3 g (89 mmol), corresponding to 59.3% of theory.

Synthesis of Compound 7

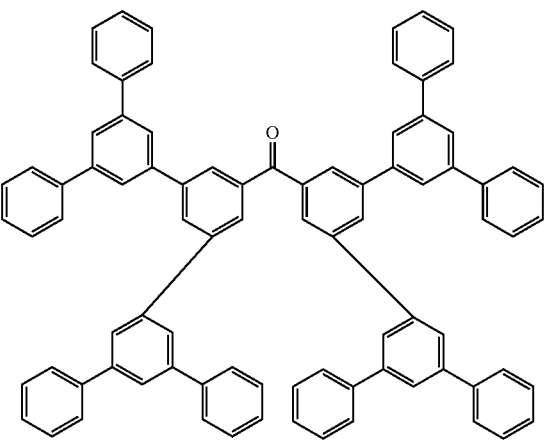

7

The synthesis is carried out analogously to compound 5, with phenylboronic acid being replaced by 1-bromo-[3,1'; 5,1"]-terphen-1-yl. The yield is 105.3 g (96 mmol), corresponding to 64.0% of theory.

Synthesis of Compound 8

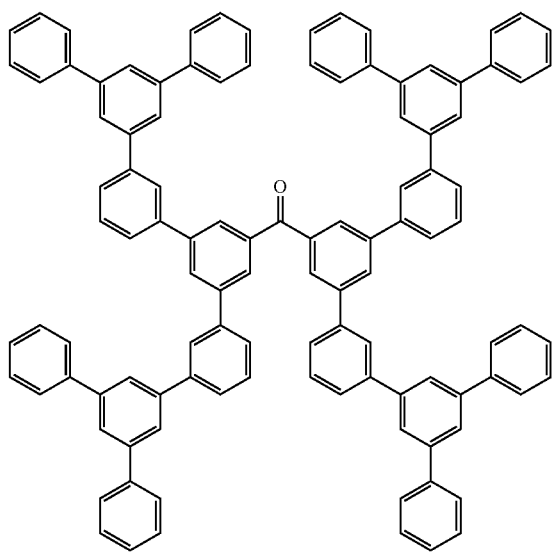

The synthesis is carried out analogously to compound 5, with phenylboronic acid being replaced by 1-bromo-3-([3, 1';5,1"]-terphen-1-yl)benzene. The yield is 123.2 g (88 mmol), corresponding to 58.7% of theory.

Comparison of the Properties

|  | Compound 5 | Compound 6 | Compound 7 | Compound 8 |
|---|---|---|---|---|
| $\Delta T_g$ (° C.) | 0 | 8.2 | 27.0 | 39.2 |
| $\Delta$HOMO (eV) | 0 | 0.05 | 0.02 | 0.01 |
| $\Delta$LUMO (ev) | 0 | 0.01 | 0.00 | 0.01 |

As can be seen from the results, compound 8 according to the invention has the same energy levels as comparable compounds in accordance with the prior art, but with a significantly higher $T_g$.

Example 3: Synthesis of Compounds 9 to 12

Synthesis of Compound 9

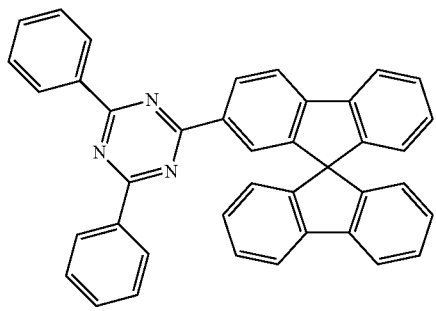

28.0 g (50.0 mmol) of spiro-9,9'-bifluorene-2-boronic acid, 14.7 g (55.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 hours. After cooling, the organic phase is separated off, filtered through silica gel, washed three times with 200 ml of water and subsequently evaporated to dryness. The residue is recrystallised from toluene and finally sublimed in high vacuum. The yield is 38 g (41.5 mmol), corresponding to 95.0% of theory.

Synthesis of Compound 10

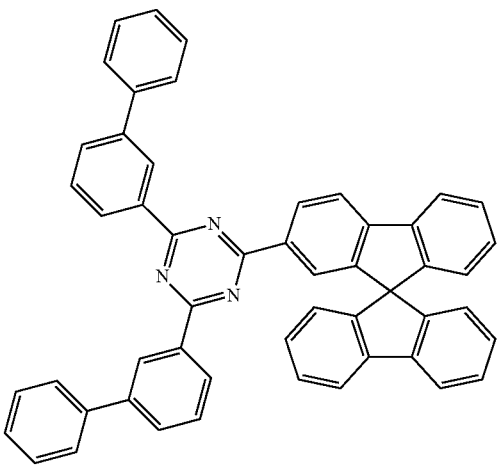

a) Synthesis of 2-chloro-(4,6-bisbiphen-3-yl)-1,3,5-triazine 80.2 ml of a 2.0 molar solution of n-butyllithium in hexane are slowly added dropwise to a solution, cooled to −78° C., of 37.3 g (160 mmol) of 3-bromobiphenyl in 250 ml of abs. tetrahydrofuran, and the mixture is stirred for 15 minutes. The reaction solution is slowly added dropwise to a solution, cooled to −78° C., of 10.0 g (45 mmol) of cyanuric chloride in 400 ml of abs. tetrahydrofuran, and the cooling is removed. When room temperature has been reached, the precipitated product is filtered off. The yield is 14.7 g (35 mmol), corresponding to 77.8% of theory.

b) Synthesis of 2-(4,6-bisbiphen-3-yl)-1,3,5-triazin-2-yl)spiro-9,9'-bifluorene

The synthesis is carried out analogously to compound 9 with 10.2 g (28.3 mmol) of spiro-9,9'-bifluorene-2-boronic acid, with 2-chloro-4,6-diphenyl-1,3,5-triazine being replaced by 10.5 g (25.0 mmol) of 2-chloro-4,6-bis(biphen-3-yl)-1,3,5-triazine. The yield is 12.7 g (17.8 mmol), corresponding to 71.3% of theory.

Synthesis of Compound 11

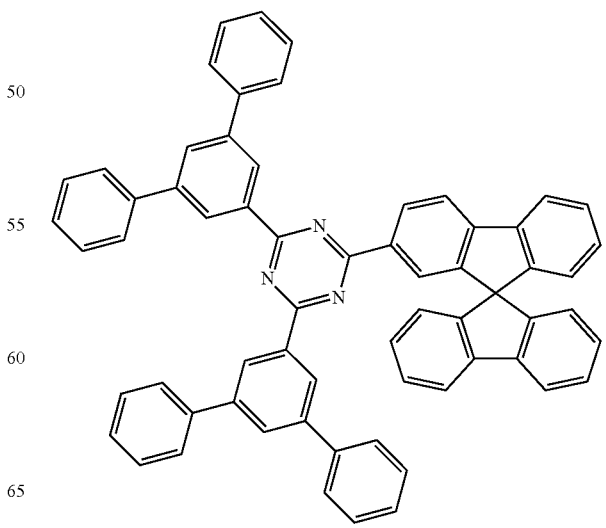

a) Synthesis of 2-chloro-(4,6-bis-(3,1';5,1''-terphen-1-yl)-1,3,5-triazine

The synthesis is carried out analogously to compound 10 (step 1), with 3-bromobiphenyl being replaced by 50.3 g (163 mmol) of 1-bromo-[3,1';5,1'']-terphen-1-yl. The yield is 21.1 g (37 mmol), corresponding to 67.9% of theory.

b) Synthesis of 2-(4,6-bis-(3,1';5,1''-terphen-1-yl)-1,3,5-triazin-2-yl)spiro-9,9'-bifluorene The synthesis is carried out analogously to compound 9 with 17.5 g (48 mmol) of spiro-9,9'-bifluorene-2-boronic acid, with 2-chloro-4,6-diphenyl-1,3,5-triazine being replaced by 21.06 g (37 mmol) of 2-chloro-(4,6-bis-[3,1';5,1'']-terphen-1-yl)-1,3,5-triazine. The yield is 20.2 g (24 mmol), corresponding to 64.4% of theory.

Synthesis of Compound 12

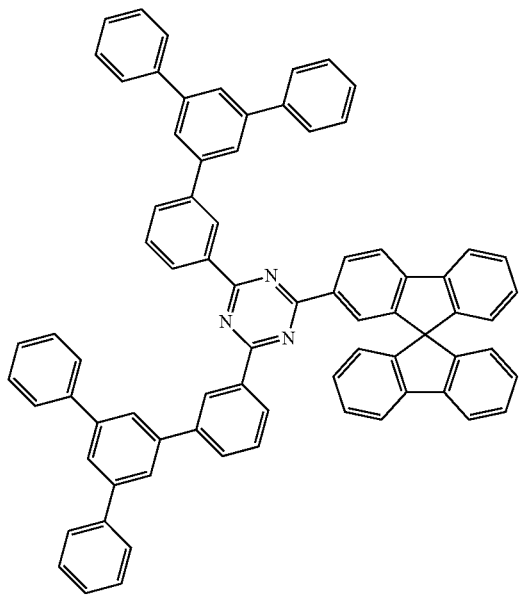

12 a) Synthesis of 2-chloro-4,6-bis-(3-([3,1';5,1'']-terphen-1-yl)phen-1-yl)-1,3,5-triazine The synthesis is carried out analogously to compound 10 (step 1), with 3-bromobiphenyl being replaced by 43.88 g (143 mmol) of 1-bromo-3-([3,1';5,1'']-terphen-1-yl)benzene. The yield is 6.3 g (9.0 mmol), corresponding to 23.3% of theory.

b) Synthesis of 2-(4,6-bis-(3-([3,1';5,1'']-terphen-1-yl)phen-1-yl)-1,3,5-triazin-2-yl)spiro-9,9'-bifluorene The synthesis is carried out analogously to compound 9 with 4.07 g (11.3 mmol) of spiro-9,9'-bifluorene-2-boronic acid, with 2-chloro-4,6-diphenyl-1,3,5-triazine being replaced by 6.3 g (9.0 mmol) of 2-chloro-4,6-bis-(3-([3,1'; 5,1'']-terphen-1-yl)phen-1-yl)-1,3,5-triazine. The yield is 4.9 g (4.8 mmol), corresponding to 56.3% of theory.

Comparison of the Properties

|  | Compound 9 | Compound 10 | Compound 11 | Compound 12 |
|---|---|---|---|---|
| $\Delta T_g$ (° C.) | 0.00 | 4.20 | 24.7 | 37.3 |
| $\Delta$HOMO (eV) | 0.00 | 0.02 | 0.02 | 0.01 |
| $\Delta$LUMO (eV) | 0.00 | 0.01 | 0.03 | 0.02 |

As can be seen from the results, compound 12 according to the invention has the same energy levels as comparable compounds in accordance with the prior art, but with a significantly higher $T_g$.

Example 4: Synthesis of Compounds 13 to 17

Synthesis of Compound 13

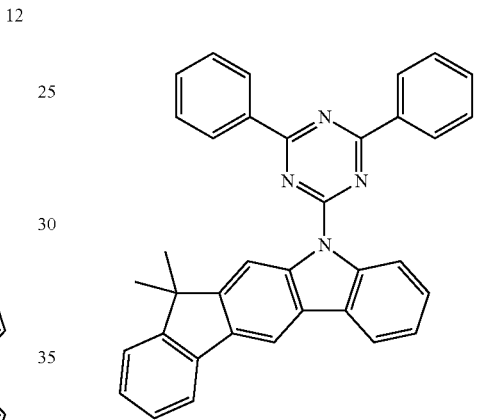

13

8 g (28.2 mmol) of 12,12-dimethyl-10,12-dihydro-10-azaindeno[2,1-b]fluorene are dissolved in 225 ml of dimethylformamide under a protective-gas atmosphere, and 1.5 g of NaH, 60% in mineral oil (37.5 mmol), are added. After 1 hour at room temperature, a solution of 2-chloro-4,6-diphenyl-1,3,5-triazine (8.5 g, 31.75 mmol) in 75 ml of dimethylformamide is added dropwise. The reaction mixture is then stirred at room temperature for 12 hours. After this time, the reaction mixture is poured onto ice and extracted three times with dichloromethane. The combined organic phases are dried over $Na_2SO_4$ and evaporated. The residue is extracted with hot toluene. The yield is 12 g (23 mmol), corresponding to 83% of theory.

Synthesis of Compound 14

18.6 g (64.6 mmol) of 12,12-dimethyl-10,12-dihydro-10-azaindeno[2,1-b]-fluorene are dissolved in 400 ml of dimethylformamide under a protective-gas atmosphere, and 3.1 g of NaH, 60% in mineral oil (77.5 mmol), are added. After 1 hour at room temperature, a solution of 2,4-bisbiphenyl-3-yl-6-chloro-1,3,5-triazine (32.6 g, 64.6 mmol) in 100 ml of THF is added dropwise. The reaction mixture is stirred at room temperature for 12 hours. After this time, the reaction mixture is poured onto ice and extracted three times with dichloromethane. The combined organic phases are dried over Na$_2$SO$_4$ and evaporated. The residue is extracted with hot toluene, recrystallised from toluene and finally sublimed in high vacuum. The yield is 41.5 g (61 mmol), corresponding to 80% of theory.

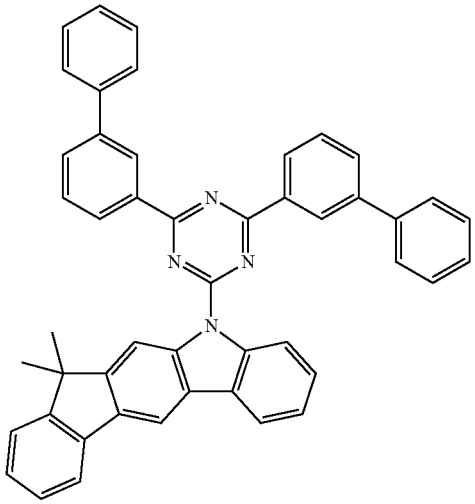

Synthesis of Compound 15

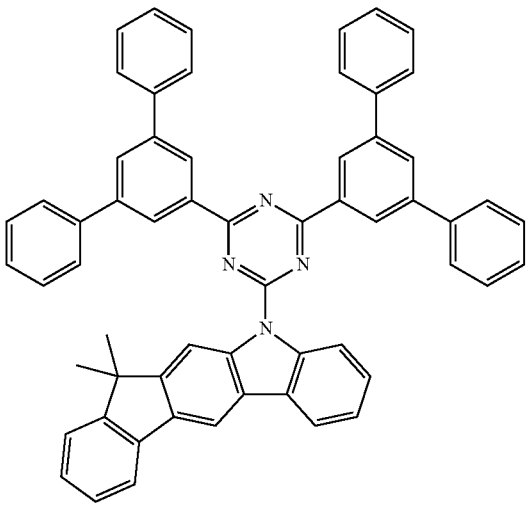

11.3 g (40 mmol) of 12,12-dimethyl-10,12-dihydro-10-azaindeno[2,1-b]fluorene are dissolved in 285 ml of dimethylformamide under a protective-gas atmosphere, and 1.9 g of NaH, 60% in mineral oil (19 mmol), are added. After 1 hour at room temperature, a solution of 2-chloro-4,6-bis-[1,1';3',1"]-terphenyl-5'-yl-1,3,5-triazine (25.1 g, 44 mmol) in 315 ml of dimethylformamide is added dropwise. The reaction mixture is stirred at room temperature for 12 hours. After this time, the reaction mixture is poured onto ice and extracted three times with dichloromethane. The combined organic phases are dried over Na$_2$SO$_4$ and evaporated. The residue is extracted with hot toluene. The yield is 23 g (28 mmol), corresponding to 70% of theory.

Synthesis of Compound 16

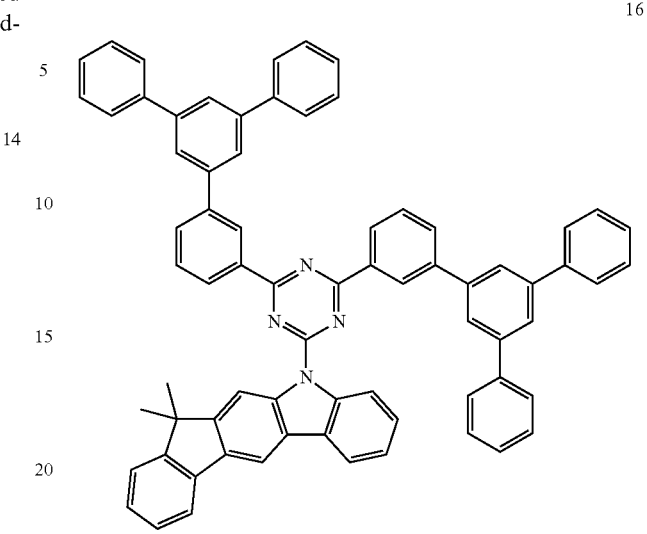

8.0 g (28 mmol) of 12,12-dimethyl-10,12-dihydro-10-azaindeno[2,1-b]fluorene are dissolved in 210 ml of dimethylformamide under a protective-gas atmosphere, and 1.4 g of NaH, 60% in mineral oil (35 mmol), are added. After 1 hour at room temperature, a solution of 2-chloro-[4,6-bis-5'-(3-bromophenyl)-[1,1';3',1"]terphenyl-5'-yl]-1,3,5-triazine (22.5 g, 31 mmol) in 250 ml of dimethylformamide is added dropwise. The reaction mixture is stirred at room temperature for 12 hours. After this time, the reaction mixture is poured onto ice and extracted three times with dichloromethane. The combined organic phases are dried over Na$_2$SO$_4$ and evaporated. The residue is recrystallised from heptane/toluene. The yield is 12.2 g (13 mmol), corresponding to 44% of theory.

Synthesis of Compound 17

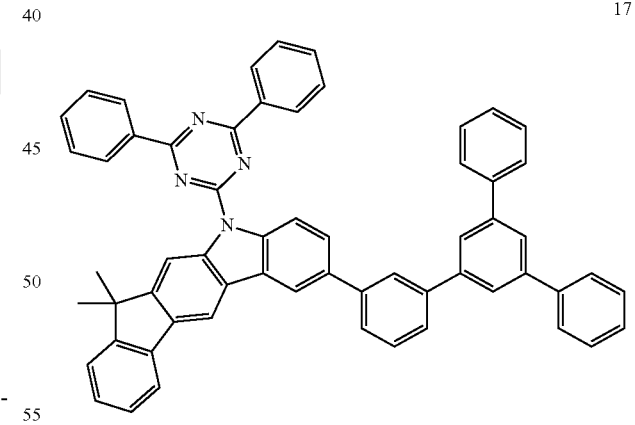

25.0 g (42.1 mmol) of 7-bromo-10-(4,6-diphenyl-1,3,5-triazin-2-yl)-12,12-dimethyl-10,12-dihydro-10-azaindeno[2,1-b]fluorene and 19.9 g of 1-pinacolylboronato-3-([3,1',5,1"]terphen-1-yl)benzene (46.3 mmol) are dissolved in 80 ml of toluene and degassed. 281 ml of degassed 2 M K$_2$CO$_3$ and 2.4 g (2.1 mmol) of Pd(PPh$_3$)$_4$ are added. The reaction mixture is subsequently stirred at 80° C. for 48 hours under a protective-gas atmosphere. Toluene is added to the cooled solution, and the mixture is washed a number of times with water, dried and evaporated. The residue is recrystallised from heptane/toluene. The yield is 21.8 g (26.6 mmol), corresponding to 63.2% of theory.

| | Compound 13 | Compound 14 | Compound 15 | Compound 16 | Compound 17 |
|---|---|---|---|---|---|
| $\Delta T_g$ (° C.) | 0.0 | 6.9 | 26.5 | 57.1 | 59.3 |
| $\Delta$HOMO (eV) | 0.00 | 0.01 | 0.00 | 0.01 | 0.01 |
| $\Delta$LUMO (eV) | 0.00 | 0.00 | 0.01 | 0.01 | 0.01 |

As can be seen from the results, compounds 16 and 17 according to the invention have the same energy levels as comparable compounds in accordance with the prior art, but with a significantly higher $T_g$.

Example 5: Synthesis of Compound 18

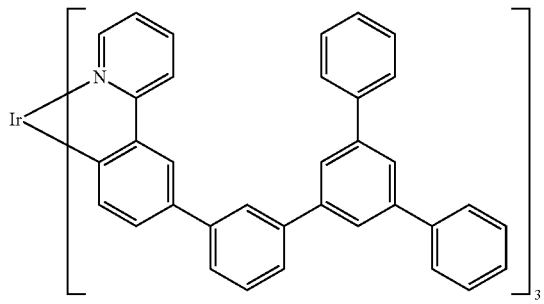

18

1.7 g (2.0 mmol) of fac-tris[2-(2-pyridinyl-κN)(5-bromophenyl)-κC]-iridium(III), 7.42 g (17 mmol) of 1-pinacolylboronato-3-([3,1';5,1"]terphen-1-yl)benzene, 2.51 g (12 mmol) of potassium phosphate are suspended in 100 ml of toluene, 100 ml of dioxane and 111 ml of water. 4 mg (0.1 mmol) of palladium(II) acetate and 35 mg (0.2 mmol) of tri-o-tolylphosphine are added to this suspension, and the reaction mixture is heated under reflux for 24 hours. After cooling, the organic phase is separated off, washed three times with 200 ml of water, filtered through silica gel, dried using sodium sulfate and subsequently evaporated to dryness. The residue is recrystallised from dioxane/ethanol and finally dried under reduced pressure. The yield is 2.42 g (1.6 mmol), corresponding to 80.9% of theory.

| | T-1 Ir(ppy)$_3$ | Compound 18 |
|---|---|---|
| $\Delta T_m$ (° C.) | 0.0 | 32.8 |
| $\Delta$HOMO (eV) | 0.00 | 0.06 |
| $\Delta$LUMO (eV) | 0.00 | 0.06 |

As can be seen from the results, compound 18 according to the invention has the same energy levels as the comparable compound (Ir(ppy)$_3$) in accordance with the prior art, but with a significantly higher $T_g$.

Example 6: Synthesis of Compounds 20 to 29

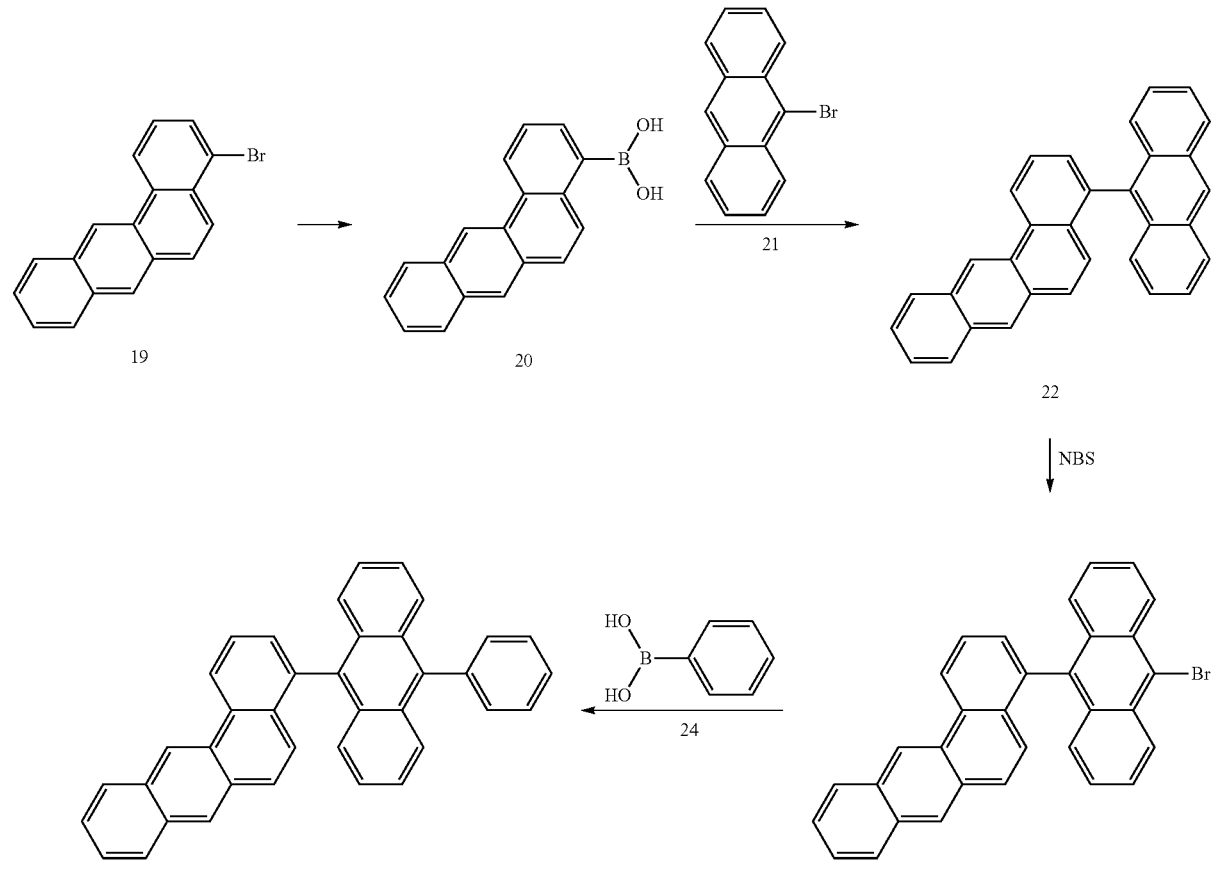

Synthesis of Compound 20

52 ml (130 mmol) of n-butyllithium (2.5 M in n-hexane) are added dropwise to a suspension of 30.7 g (100 mmol) of 4-bromobenz[a]anthracene (19) in 1000 ml of THF at −78° C. with vigorous stirring, and the mixture is stirred for a further 2 hours. 16.7 ml (150 mmol) of trimethyl borate are added in one portion to the red solution with vigorous stirring, the mixture is stirred at −78° C. for a further 30 minutes and then warmed to room temperature over the course of 3 hours, 300 ml of water are added, and the mixture is stirred for 30 minutes. The organic phase is separated off and evaporated to dryness in vacuo. The solid is taken up in 100 ml of n-hexane, filtered off with suction, washed once with 100 ml of n-hexane and dried in vacuo. Yield: 23.7 g (87.0 mmol), corresponding to 87.0% of theory, purity about 90.0% (NMR) of the boronic acid, with varying amounts of the boronic anhydride and borinic acid. The boronic acid can be used in this form without further purification.

Synthesis of Compound 22

25.0 g (97.2 mmol) of 9-bromoanthracene (21), 27.0 g (99.2 mmol) of benz[a]anthracene-4-boronic acid (20) and 44.5 g (210 mmol) of tripotassium phosphate are suspended in 500 ml of toluene, 600 ml of water and 100 ml of dioxane. 1.83 g (6.01 mmol) of tri-o-tolylphosphine and then 225 mg (1.0 mmol) of palladium(II) acetate are added to this suspension, and the mixture is subsequently heated under reflux for 16 hours. After cooling, the organic phase is separated off, washed three times with 500 ml of water, dried using sodium sulfate and subsequently evaporated to dryness. The solid is recrystallised from 300 ml of toluene and finally dried under reduced pressure. The yield is 26.2 g (64.8 mmol), corresponding to 64.8% of theory.

Synthesis of Compound 23

1.3 g (8.02 mmol) of iron(III) chloride and then 13.3 g (74.7 mmol) of N-bromosuccinimide are added to a suspension, cooled to 0° C., of 26.0 g (64.3 mmol) of 22 in 600 ml of chloroform, and the mixture is stirred at 0° C. for 4 hours. After the mixture has warmed to room temperature, 400 ml of water are added, and the organic phase is separated off, washed three times with 300 ml of water, dried using sodium sulfate and subsequently evaporated to dryness. The orange solid obtained is recrystallised from toluene and finally dried under reduced pressure. The yield is 23.7 g (49.0 mmol), corresponding to 76.6% of theory.

Synthesis of Compound 25

10.0 g (20.7 mmol) of 23, 2.80 g (23.0 mmol) of phenylboronic acid (24) and 8.5 g (80.2 mmol) of sodium carbonate are suspended in 70 ml of toluene, 56 ml of water and 21 ml of ethanol. 240 mg (0.208 mmol) of tetrakis(triphenylphosphine)palladium(0) are added to this suspension, and the mixture is subsequently heated under reflux for 16 hours. After cooling, the precipitated solid is filtered off with suction, washed three times with 50 ml of toluene, three times with 50 ml of ethanol:water (1:1, v:v) and three times with 100 ml of ethanol, recrystallised three times from DMF (about 10 ml/g) and subsequently sublimed twice. The yield is 6.07 g (12.6 mmol), corresponding to 61.3% of theory.

Synthesis of Compound 27

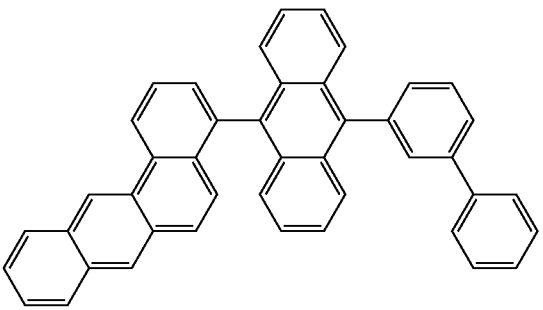

27

The synthesis is carried out analogously to compound 25 with 6.0 g (12.4 mmol) of compound 23, with compound 24 being replaced by 2.8 g (14.1 mmol) of biphenyl-3-boronic acid (26). The yield is 5.04 g (9.05 mmol), corresponding to 73.0% of theory.

Synthesis of Compound 28

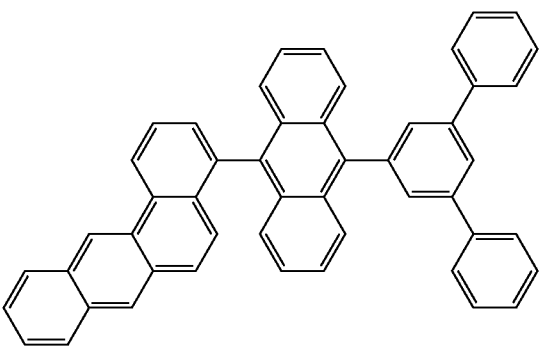

28

The synthesis is carried out analogously to compound 25 with 3.0 g (6.21 mmol) of compound 23, with compound 24 being replaced by 1.87 g (6.82 mmol) of 3-borono-[3,1';5,1"]terphenyl (2). The yield is 3.41 g (5.39 mmol), corresponding to 86.8% of theory.

Synthesis of Compound 29

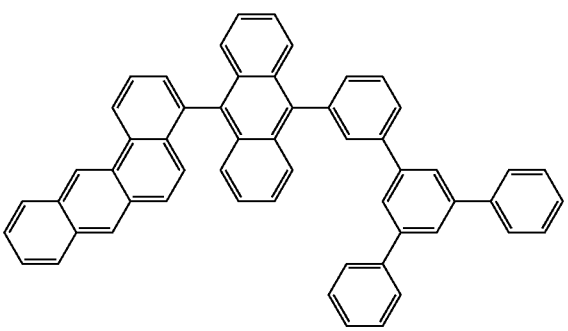

29

The synthesis is carried out analogously to compound 25 with 2.0 g (4.14 mmol) of compound 23, with compound 24 being replaced by 2.0 g (4.63 mmol) of 1-borono-3-([3,1';5,1"]-terphen-1-yl)benzene (4). The yield is 2.72 g (3.84 mmol), corresponding to 93.8% of theory.

Comparison of the Properties

|  | Compound 25 | Compound 27 | Compound 28 | Compound 29 |
|---|---|---|---|---|
| $\Delta T_g$ (° C.) | 0.00 | 1.9 | 23.2 | 29.0 |
| $\Delta$HOMO (eV) | 0.00 | 0.01 | 0.00 | 0.00 |
| $\Delta$LUMO (eV) | 0.00 | 0.00 | 0.00 | 0.00 |

As can be seen from the results, compound 29 according to the invention has the same energy levels as comparable compounds in accordance with the prior art, but with a significantly higher $T_g$.

Example 7: Production and Characterisation of Organic Electroluminescent Devices Materials according to the invention are used from solution, where they result in simple devices having nevertheless good properties. The production of such components is based on the production of polymeric light-emitting diodes (PLEDs), which has already been described many times in the literature (for example in WO 2004/037887 A2). In the present case, the compounds according to the invention are dissolved in toluene or chlorobenzene. The concentration employed in the examples given here is 20% by weight of the emitter (T-1 or compound 18) and 80% by weight of the matrix materials (compounds 5 to 17). The typical solids content of such solutions is between 16 and 25 g/l if, as here, the typical layer thickness of 80 nm for a device is to be achieved by means of spin coating.

FIG. 1 shows the typical structure of a device of this type. The EML comprises the jointly dissolved matrix materials and the emitter in the form of an amorphous layer. Structured ITO substrates and the material for the so-called buffer layer (PEDOT, actually PEDOT:PSS) are commercially available (ITO from Technoprint and others, PEDOT:PSS as Clevios P aqueous dispersion from H.C. Starck). The interlayer used (HIL-012 from Merck) serves for hole injection. The emission layer is applied by spin coating in an inert-gas atmosphere, in the present case argon, and dried by heating at 160° C. or 180° C. for 10 minutes. Finally, a cathode comprising barium and aluminium is applied by vacuum vapour deposition. The HBL and ETL layers used in the above-mentioned examples can also be applied by vapour deposition between the EML and the cathode, and the interlayer can also be replaced by one or more layers, which merely have to satisfy the condition of not being detached again by the subsequent processing step of EML deposition from solution.

The solution-processed devices were characterised by standard methods, and the OLED examples mentioned were not optimised. Table 1 shows the results.

TABLE 1

Results of the device configuration shown in FIG. 1

| Ex. | EML 80 nm | Max. eff. [cd/A] | Voltage [V] at 1000 cd/m² | CIE (x, y) | Lifetime [h], initial luminance 1000 cd/m² |
|---|---|---|---|---|---|
| Comp. | Compound 05: T-1 | 27 | 4.2 | 0.36/0.62 | 2000 |
| Comp. | Compound 06: T-1 | 28 | 4.3 | 0.35/0.61 | 3500 |
| Comp. | Compound 07: T-1 | 30 | 4.1 | 0.35/0.62 | 4000 |
|  | Compound 08: T-1 | 37 | 4.2 | 0.35/0.62 | 17000 |
| Comp. | Compound 09: T-1 | 11 | 5.7 | 0.36/0.61 | 9500 |
| Comp. | Compound 10: T-1 | 14 | 5.6 | 0.36/0.61 | 10000 |
| Comp. | Compound 11: T-1 | 15 | 5.5 | 0.36/0.61 | 9000 |
|  | Compound 12: T-1 | 24 | 5.5 | 0.36/0.61 | 20500 |
| Comp. | Compound 13: T-1 | 14 | 4.3 | 0.33/0.62 | 3800 |
| Comp. | Compound 14: T-1 | 13 | 4.5 | 0.33/0.62 | 5200 |
| Comp. | Compound 15: T-1 | 15 | 4.4 | 0.33/0.62 | 4600 |
|  | Compound 16: T-1 | 26 | 4.1 | 0.34/0.62 | 18400 |
|  | Compound 17: T-1 | 28 | 4.2 | 0.34/0.62 | 23000 |
| Comp. | Compound 09: T-1 | 11 | 5.7 | 0.36/0.61 | 9500 |
|  | Compounds 9: 18 | 28 | 5.0 | 0.35/0.62 | 20500 |

As can be seen from the results, compounds 8, 12, 16, 17 and 18 according to the invention represent a significant improvement over the comparable compounds in accordance with the prior art with respect to operating voltage, lifetime and efficiency.

Example 8: Production and Characterisation of Organic Electroluminescent Devices—(Compounds 25, 27, 28, 29)

The concentration employed in the examples given here is 5% by weight of the emitter (SEB-095, Merck) and 95% by weight of the matrix materials (compounds 28 and 29). The typical solids content of such solutions is between 15 g/l if, as here, the typical layer thickness of 50 nm for a device is to be achieved by means of spin coating. Table 2 shows the device results.

TABLE 2

Results of the device configuration

| Ex. | EML 50 nm | Max. eff. [cd/A] | Voltage [V] at 1000 cd/m² | CIE (x, y) | Lifetime [h], initial luminance 1000 cd/m² |
|---|---|---|---|---|---|
| Comp. | Compound 25: emitter | n/a | n/a | n/a | n/a |
| Comp. | Compound 27: emitter | n/a | n/a | n/a | n/a |
| Comp. | Compound 28: emitter | 5.0 | 4.8 | 0.14, 0.17 | 300 |
|  | Compound 29: emitter | 6.1 | 4.9 | 0.14, 0.17 | 500 |

Owing to the poor solubility of compounds 25 and 27, it was not possible to produce devices with these matrices. However, compounds 28 and 29 can be processed well due to the improved solubility. As can be seen from Table 2, compound 29 according to the invention represents a significant improvement over the comparable compound in accordance with the prior art with respect to lifetime and efficiency.

The invention claimed is:

1. A formulation comprising at least one solvent and at least one functional compound of the general formula (I)

  (I)

where
A is a functional structural element which has electron-injection and/or electron-transport properties and the functional structural element which has electron-injection and/or electron-transport properties is selected from the group consisting of triazine derivatives and ketone derivatives,
B is a solubility-promoting structural element and
k is an integer in the range from 1 to 20,
wherein
the solubility-promoting structural element B conforms to the general formula (L-I)

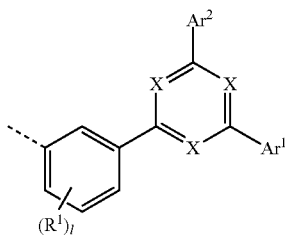
  (L-I)

where
$Ar^1$ and $Ar^2$ are each, independently of one another, an aryl or heteroaryl group, which may be substituted by one or more radicals R,
X is in each case, independently of one another, N or $CR^2$,
$R^1$ and $R^2$ are each, independently of one another, hydrogen, a straight-chain alkyl, alkoxy or thioalkoxy group having 1 to 40 C atoms or a branched or cyclic alkyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—X', in which X' represents a halogen atom), a formyl group (—C(=O)—H), an isocyano group, an isocyanate group, a thiocyanate group or a thioisocyanate group, a hydroxyl group, a nitro group, a CF$_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$ and/or $R^2$ may form a mono- or polycyclic, aliphatic or aromatic ring system with one another and/or with the ring to which the group $R^1$ is bonded; and
l is 0, 1, 2, 3 or 4;
where the dashed bond indicates the bond to the functional structural element A.

2. The formulation according to claim 1, wherein X is CH.

3. The formulation according to claim 1, wherein the solubility-promoting structural element B conforms to the general formula (L-II)

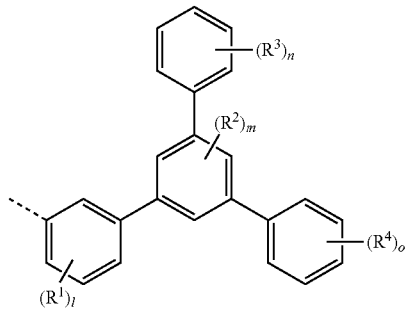
  (L-II)

where
$R^1$, $R^2$, $R^3$, $R^4$ are each, independently of one another, a straight-chain alkyl, alkenyl or thioalkoxy group having 1 to 40 C atoms or a branched or cyclic alkyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a formyl group (—C(=O)—H), a CF$_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups R', $R^2$, $R^3$ and/or $R^4$ optionally form a mono- or polycyclic, aliphatic or aromatic ring system with one another and/or with another ring;
m is 0, 1, 2 or 3,
n, o are each, independently of one another, 0, 1, 2, 3, 4 or 5
and the dashed bond and the index 1 have the meaning mentioned in claim 1.

4. The formulation according to claim 1, wherein the formulation comprises at least 80% by weight of aromatic or heteroaromatic solvent.

5. The formulation according to claim 1, wherein the index k in formula (I) is an integer greater than or equal to 2.

6. The formulation according to claim 1, wherein the molecular weight of the functional compound of the general formula (I) is at least 900 g/mol.

7. The formulation according to claim 1, wherein the functional compound of the general formula (I) has a glass-transition temperature of at least 70° C.

8. The formulation according to claim 1, wherein the functional structural element A in formula (I) is a unit which has light-emitting properties.

9. The formulation according to claim 8, wherein the functional structural element A in formula (I) is a unit having phosphorescent properties.

10. The formulation according to claim 8 wherein the functional structural element A in formula (I) is a unit which contains at least one heavy atom having an atomic number of greater than 36.

11. The formulation according to claim 1, wherein the functional structural element A in formula (I) is a unit which improves the transfer from the singlet state to the triplet state of light-emitting compounds.

12. The formulation according to claim 1, wherein the weight ratio of structural element A to structural element B in formula (I) is in the range from 2:1 to 1:20.

13. A functional compound of the general formula (I)

wherein
A is a functional structural element which has electron-injection and/or electron-transport properties, and the functional structural element which has electron-injection and/or electron-transport properties is selected from the group consisting of triazine derivatives and ketone derivatives,
B is a solubility-promoting structural element and
k is an integer in the range from 1 to 20,
wherein
the molecular weight of the functional compound is at least 800 g/mol and
the solubility-promoting structural element B conforms to the formula (L-I)

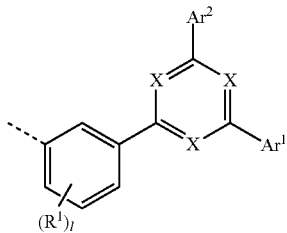

where
$Ar^1$ and $Ar^2$ are each, independently of one another, an aryl or heteroaryl group, which may be substituted by one or more radicals R of any desired type,
X is in each case, independently of one another, N or $CR^2$,
$R^1$ and $R^2$ are each, independently of one another, hydrogen, a straight-chain alkyl, alkoxy or thioalkoxy group having 1 to 40 C atoms or a branched or cyclic alkyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—X', in which X' represents a halogen atom), a formyl group (—C(=O)—H), an isocyano group, an isocyanate group, a thiocyanate group or a thioisocyanate group, a hydroxyl group, a nitro group, a CF$_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$ and/or $R^2$ optionally form a mono- or polycyclic, aliphatic or aromatic ring system with one another and/or with the ring to which the group $R^1$ is bonded; and
l is 0, 1, 2, 3 or 4;
where the dashed bond indicates the bond to the functional structural element A;
with the exception of compounds of the general formula (A-I)

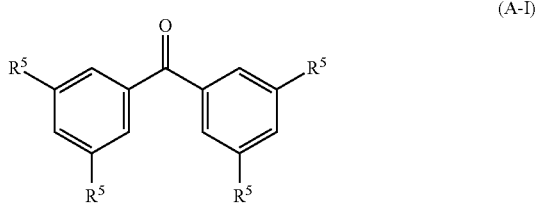

where the following applies to the symbols used:
$R^5$ is on each occurrence, identically or differently, hydrogen or an aromatic or heteroaromatic ring system having 5 to 60 aromatic ring atoms, which may be substituted by one or more radicals $R^6$, or an N(Ar)$_2$, Si(Ar)$_3$, C(=O)Ar, OAr, ArSO, ArSO$_2$, P(Ar)$_2$, P(O)(Ar)$_2$ or B(Ar)$_2$ group,
$R^6$ is on each occurrence, identically or differently, H, D, F, Cl, Br, I, CHO, N(Ar)$_2$, C(=O)Ar, P(=O)(Ar)$_2$, S(=O)Ar, S(=O)$_2$Ar, $CR^7$=$CR^7$Ar, CN, NO$_2$, Si(R$^8$)$_3$, B(OR$^8$)$_2$, B(R$^8$)$_2$, B(N(R$^8$)$_2$)$_2$, OSO$_2$R$^8$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals R$^8$, where one or more non-adjacent CH$_2$ groups are optionally replaced by R$^8$C=CR$^8$, C≡C, Si(R$^8$)$_2$, Ge(R$^8$)$_2$, Sn(R$^8$)$_2$, C=O, C=S, C=Se, C=NR$^8$, P(=O)(R$^8$), SO, SO$_2$, NR$^8$, O, S or CONR$^8$ and where one or more H atoms are optionally replaced by F, Cl, Br, I, CN or NO$_2$, or an aromatic or heteroaromatic ring system having 5 to 60 aromatic ring atoms, which may in each case be substituted by one or more radicals R$^8$, or an aryloxy or heteroaryloxy group having 5 to 60 aromatic ring atoms, which may be substituted by one or more radicals R$^8$, or a combination of these systems;
$R^7$ is on each occurrence, identically or differently, H, D, F or a linear alkyl group having 1 to 20 C atoms or a branched or cyclic alkyl group having 3 to 20 C atoms; a plurality of radicals $R^7$ here may form a ring system with one another;
$R^8$ is on each occurrence, identically or differently, H, D or an aliphatic, aromatic and/or heteroaromatic hydrocarbon radical having 1 to 20 C atoms, in which, in addition, H atoms are optionally replaced by F; and
Ar is on each occurrence, identically or differently, an aromatic or heteroaromatic ring system having 5 to 30 aromatic ring atoms, which may be substituted by one or more non-aromatic radicals R$^6$; two radicals Ar here which are bonded to the same nitrogen, phosphorus or boron atom may also be linked to one another by a single bond or a bridge selected from B(R$^8$), C(R$^8$)$_2$, Si(R$^8$)$_2$, C=O, C=NR$^8$, C=C(R$^8$)$_2$, O, S, S=O, SO$_2$, N(R$^8$), P(R$^8$) and P(=O)R$^8$.

14. The compound according to claim 13, wherein the molecular weight is at least 900 g/mol.

15. The compound according to claim 13, wherein the index k in formula (I) is at least 3.

16. An electronic device containing the compound according to claim 13.

17. The electronic device according to claim 16, wherein the organic compound is present in the device as hole-transport, hole-injection, emitter, electron-transport, electron-injection, charge-blocking and/or charge-generation layer.

18. The electronic device according to claim 16, wherein the electronic device is an organic electroluminescent device (OLED), a polymeric electroluminescent device (PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser).

19. A process for the production of an electronic device which comprises applying the formulation according to claim 1 to a substrate and subsequently dried.

20. The formulation comprising at least one solvent and at least one functional compound of the general formula (I)

(I)

where
A is a functional structural element which has electron-injection and/or electron-transport properties and the functional structural element which has electron-injection and/or electron-transport properties is selected from the group consisting of triazine derivatives and ketone derivatives,
B is a solubility-promoting structural element and
k is an integer in the range from 1 to 20,
wherein
the solubility-promoting structural element B conforms to the general formula (L-I)

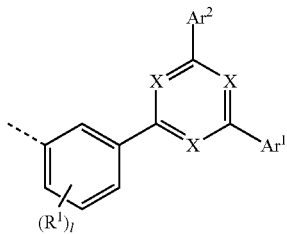
(L-I)

where
$Ar^1$ and $Ar^2$ are each, independently of one another, an aryl or heteroaryl group, which may be substituted by one or more radicals R,
X is in each case, independently of one another, N or $CR^2$,
$R^1$ and $R^2$ are each, independently of one another, hydrogen, a straight-chain alkyl, alkoxy or thioalkoxy group having 1 to 40 C atoms or a branched or cyclic alkyl, alkoxy or thioalkoxy group having 3 to 40 C atoms or a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—X', in which X' represents a halogen atom), a formyl group (—C(=O)—H), an isocyano group, an isocyanate group, a thiocyanate group or a thioisocyanate group, a hydroxyl group, a nitro group, a CF$_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$ and/or $R^2$ may form a mono- or polycyclic, aliphatic or aromatic ring system with one another and/or with the ring to which the group $R^1$ is bonded; and
l is 0, 1, 2, 3 or 4;
where the dashed bond indicates the bond to the functional structural element A
and the molecular weight of the functional compound of the general formula (I) is at least 800 g/mol.

* * * * *